(12) United States Patent
Lyman et al.

(10) Patent No.: US 11,066,359 B2
(45) Date of Patent: Jul. 20, 2021

(54) BIODEGRADABLE SURFACTANTS AND RELATED COMPOSITIONS, METHODS AND SYSTEMS

(71) Applicant: LAWRENCE LIVERMORE NATIONAL SECURITY, LLC, Livermore, CA (US)

(72) Inventors: Mathew Gerald Lyman, Brentwood, CA (US); Lawrence Dugan, Modesto, CA (US); Roald N. Leif, San Ramon, CA (US); Bonnee Rubinfeld, Danville, CA (US); Brian E. Souza, Livermore, CA (US); Carlos A. Valdez, San Ramon, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

(21) Appl. No.: 16/484,817

(22) PCT Filed: Feb. 8, 2018

(86) PCT No.: PCT/US2018/017496
§ 371 (c)(1),
(2) Date: Aug. 8, 2019

(87) PCT Pub. No.: WO2018/148465
PCT Pub. Date: Aug. 16, 2018

(65) Prior Publication Data
US 2019/0359562 A1 Nov. 28, 2019

Related U.S. Application Data

(60) Provisional application No. 62/457,719, filed on Feb. 10, 2017.

(51) Int. Cl.
*C07C 305/06* (2006.01)
*C07C 69/675* (2006.01)
*C07C 69/708* (2006.01)

(52) U.S. Cl.
CPC .......... *C07C 305/06* (2013.01); *C07C 69/675* (2013.01); *C07C 69/708* (2013.01)

(58) Field of Classification Search
CPC .... C07C 69/675; C07C 69/708; C07C 305/06
See application file for complete search history.

(56) References Cited

FOREIGN PATENT DOCUMENTS

| JP | H0995468 A | 4/1997 |
| KR | 20000037948 A | 7/2000 |
| WO | 2017/184884 A1 | 10/2017 |
| WO | 2018/148465 A1 | 8/2018 |

OTHER PUBLICATIONS

Abbott E.P. et al., "Overcoming recalcitrant transformation and gene manipulation in Pucciniomycotina yeasts." *Applied Microbiology and Biotechnology*,2013. 97(2): p. 719-729.
Bandaranayake A.D. et al., "Recent advances in mammalian protein production." *FEBS letters*,2014. 588(2): p. 253-260.
Bao Z. et al., "Homology-integrated CRISPR-Cas (HI-CRISPR) system for one-step multigene disruption in *Saccharomyces cerevisiae*" *ACS Synthetic Biology*,2014. 4(5): p. 585-594.
Bentley R. et al., "Gas chromatography of sugars and other polyhydroxy compounds." *Biochem Biophys Res Commun*,1963. 11: p. 14-8.
Bi P. et al., "The recent progress of solvent sublation." *Journal of Chromatography A*,2010. 1217(16): p. 2716-2725.
Brenton A.G. et al., "Accurate mass measurement: terminology and treatment of data." *J Am Soc Mass Spectrom*,2010. 21(11): p. 1821-35.
Cajka T. et al., "Multiplatform Mass Spectrometry-Based Approach Identifies Extracellular Glycolipids of the Yeast *Rhodotorula babjevae* UCDFST 04-877" *Journal of Natural Products*,2016, vol. 79, pp. 2580-2589.
Chang L. et al., "Separation of four flavonol glycosides from Solanum rostratum Dunal using aqueous two-phase flotation followed by preparative high-performance liquid chromatography." *Journal of Separation Science*,2017. 40(3): p. 804-812.
Davies J., "A quantitative kinetic theory of emulsion type, I. Physical chemistry of the emulsifying agent." *Proc. 2nd Intern. Congr. Surface Activity, Butterworths Scientific Publication*, London,1957: p. 426-438.
Galdieri L. et al., "Protein acetylation and acetyl coenzyme a metabolism in budding yeast." *Eukaryot Cell*,2014. 13(12)L p. 1472-83.
Garay L.A. et al., "Discovery of synthesis and secretion of polyol esters of fatty acids by four basidiomycetous yeast species in the order *Sporidiobolales.*" *Journal of Industrial Microbiology & Biotechnology*,2017. 44(6): p. 923-936.
Guo X. et al., "Calculation of hydrophile-lipophile balance for polyethoxylated surfactants by group contribution method." *Journal of Colloid and Interface Science*,2006. 298(1): p. 441-450.
Ibrahim N.M. et al., "Determination of alkylphenol ethoxylate non-ionic surfactants in trade effluents by sublation and high-performance liquid chromatography." *Analyst*,1996. 121(2): p. 239-242.

(Continued)

*Primary Examiner* — Alicia L Otton
(74) *Attorney, Agent, or Firm* — Steinfl + Bruno LLP

(57) ABSTRACT

Biodegradable surfactants are described, in which an amphiphilic heteroatom containing hydrocarbon optionally comprising at least one counterion (Z), and related compositions, methods and systems. Biodegradable surfactant described herein has an aHLB value in accordance with equation (1): aHLB=20*Gh/(Gh−Gt) (1) wherein Gh is the Group Number of a hydrophilic head portion of the biodegradable surfactant optionally comprising the at least one counterion (Z), and Gt is the Group Number of a hydrophobic tail portion of the biodegradable surfactant. A biodegradable surfactant in the sense of the disclosure can be tuned to a set hydrophilic-lipophilic balance (aHLB) by selectively modifying at least one tuning moiety of the biodegradable surfactants to provide tuned biodegradable surfactants having an increase or decrease in their adjusted hydrophilic-lipophilic balance (aHLB).

16 Claims, 33 Drawing Sheets
Specification includes a Sequence Listing.

(56) References Cited

OTHER PUBLICATIONS

International Preliminary Report on Patentability for International Application No. PCT/US2018/017496 filed on Feb. 8, 2018 on behalf of Lawrence Livermore National Laboratory dated Aug. 13, 2019 8 pages.
International Search Report for International Application No. PCT/US2018/017496filed on Feb. 8, 2018 on behalf of Lawrence Livermore National LABORATORY dated Jun. 8, 2018 4 pages.
Jarvis D.L., "Developing baculovirus-insect cell expression systems for humanized recombinant glycoprotein production." *Virology*,2003. 310(1): p. 1-7.
Kong et al., "Functional identification of glutamate cysteine ligase and glutathione synthetase in the marine yeast *Rhodosporidium diobovatum.*" *The Science of Nature*,2018. 105(4): p. 1-9.
Kurdistani S.K. et al., "Histone acetylation and deacetylation in yeast." *Nat Rev Mol Cell Biol*,2003. 4(4): p. 276-84.
Liu Y. et al., "Characterization of glyceraldehyde-3-phosphate dehydrogenase gene RtGPDI and development of genetic transformation method by dominant selection in oleaginous yeast *Rhodosporidum toruloides.*" *Applied Microbiology and Biotechnology*,2013. 97(2): p. 719-729.
Lyman M. et al., "Rhodotorula taiwanensis MD1149 produces hypoacetylated PEFA compounds with increased surface activity compared to Rhodotorula babjevae MD1169" *PLoS ONE*(13) https://doi.org/10.1371/journal.pone.0190373, 2018: p. 1-17.
Nunez A. et al., "LC/MS analysis and lipase modification of the sophorolipids produced by Rhodotorula bogoriensis" *Biotechnol Lett*,2004. 26(13): p. 1087-93.
Pasquali R.C. et al., "Some considerations about the hydrophilic-lipophilic balance system." *International Journal of Pharmaceutics*,2008. 356(1-2): p. 44-51.
Ribeiro I.A. et al., "Design of selective production of sophorolipids by Rhodotorula bogoriensis through nutritional requirements." *J Mol Recognit*,2012. 25(11): p. 630-40.
Rosano G.L. et al., "Recombinant protein expression in *Escherichia coli*: advances and challenges" *Frontiers in Microbiology*,2014. 5: p. 172.
Saerens K.M. et al., "One-step production of unacetylated sophorolipids by an acetyltransferase negative Candida bombicola." *Biotechnol Bioeng*,2011. 108(12): p. 2923-31.
Salis A. et al., "Novel mannitol based non-ionic surfactants from biocatalysis" *Journal of Molecular Catalysis B: Enzymatic*,2004, vol. 27, p. 139-146.
Santander J. et al., "Mechanisms of intrinsic resistance to antimicrobial peptides of Edwardsiella ictaluri and its influence on fish gut inflammation and virulence." *Microbiology*,2013. 159(Pt 7): p. 1471-86.
Satpute S.K. et al., "Methods for investigating biosurfactants and bioemulsifiers: a review" *Crit Rev Biotechnol*,2010. 30(2): p. 127-44.
Scarlett M. et al., "Determination of dissolved nonylphenol ethoxylate surfactants in waste waters by gas stripping and isocratic high-performance liquid chromatography." *Water Research*,1994. 28(10): p. 2109-2116.
Show P.L. et al., "Recovery of lipase derived from Burkholderia cenocepacia ST8 using sustainable aqueous two-phase flotation composed of recycling hydrophilic organic solvent and inorganic salt." *Separation and Purification Technology*,2013. 110: p. 112-118.
Stork J. et al., "Analysis of Surfactants Using the Agilent 500 Ion Trap LC/MS" *Agilent Technologies*,Feb. 2011. 4 pages.
Tulloch A. et al., "A new hydroxy fatty acid sophoroside from Candida bogoriensis" *Can. J. Chem*,1968. 46(3): p. 345-348.
Tulloch A. et al., "Extracellular Glycolipids of *Rhodotorula* Species" *Canadian Journal of Chemistry*,1964. 42: p. 830-835.
Uzoigwe C. et al., "Bioemulsifiers are not biosurfactants and require different screening approaches" Front Microbiol, Apr. 2015, 6: 245.
Van Bogaert I.N. et al., "Knocking out the MFE-2 gene of Candida bombicola leads to improved medium-chain sophorolipids production." *FEMS yeast research*,2009. 9(4): p. 610-617.
Varvaresou A. et al., "Biosurfactants in cosmetics and biopharmaceuticals." *Lett Appl Microbiol*, 2015. 61(3): p. 214-23.
Wilhelmy L., "Ueber die Abhangigkeit der Capillaritats-Constanten des Alkohols von Substanz und Gestalt des benetzten festen Korpers [On the dependence of capillarity constants of alcohols from the substance and shape of the wetted solid bodies]" *Ann. Phys.*,1863. 195: p. 177-217.
Written Opinion for International Application No. PCT/US2018/017496 filed on Feb. 8, 2018 on behalf of Lawrence Livermore National Laboratory dated Jun. 8, 2018 7 pages.
Zhang S. et al., "Engineering Rhodosporidium toruloides for increased lipid production" *Biotechnology and bioengineering*,2016. 113(5): p. 1056-1066.
Zhang S. et al., "Metabolic engineering of the oleaginous yeast *Rhodosporidium toruloides* IFO0880 for lipid overproduction during high-density fermentation." *Applied Microbiology and Biotechnology*,2016. 100(21): p. 9393-9405.
Zhang X. et al., "Enzymatic production and functional characterization of D-sorbitol monoesters with various fatty acids" *Catalysis Communication*, 2015, vol. 72, p. 138-141.

| Compound | Formula | Exact Mass | Ion Species | Exact Ion Mass m/z | Measured Ion Mass m/z | Mass Accuracy (ppm) |
|---|---|---|---|---|---|---|
| C22:0 SL | C$_{34}$H$_{64}$O$_{13}$ | 680.4347 | [M+H]$^+$ | 681.4420 | 681.4418 | 0.25866 |
| | | | [M+NH$_4$]$^+$ | 698.4685 | 698.4688 | -0.40709 |
| | | | [M+Na]$^+$ | 703.4239 | 703.4243 | -0.56141 |
| C22:0-6" Ac SL | C$_{36}$H$_{66}$O$_{14}$ | 722.4453 | [M+H]$^+$ | 723.4525 | 723.4519 | 0.93571 |
| | | | [M+NH$_4$]$^+$ | 740.4791 | 740.4798 | -0.93710 |
| | | | [M+Na]$^+$ | 745.4345 | 745.4349 | -0.52876 |
| C22:0-6' Ac SL | C$_{36}$H$_{66}$O$_{14}$ | 722.4453 | [M+H]$^+$ | 723.4525 | 723.4528 | -0.31006 |
| | | | [M+NH$_4$]$^+$ | 740.4791 | 740.4790 | 0.17026 |
| | | | [M+Na]$^+$ | 745.4345 | 745.4347 | -0.25192 |
| C22:0-6',6" Ac SL | C$_{38}$H$_{68}$O$_{15}$ | 764.4558 | [M+H]$^+$ | 765.4631 | 765.4624 | 0.88429 |
| | | | [M+NH$_4$]$^+$ | 782.4896 | 782.4899 | -0.36235 |
| | | | [M+Na]$^+$ | 787.4450 | 787.4457 | -0.89214 |

*FIG. 1C*

| Compounds | Formula | Exact Mass | Ion Species | Exact Ion Mass m/z | Measured Ion Mass m/z | Mass Accuracy (ppm) | DBE |
|---|---|---|---|---|---|---|---|
| Mannitol, 0 Acetyl, 3-hydroxy C18 | C₂₄H₄₈O₈ | 464.3349 | [M+H]⁺ | 465.3422 | ND | --- | 1 |
| | | | [M+NH₄]⁺ | 482.3687 | 482.3686 | 0.28490 | |
| | | | [M+Na]⁺ | 487.3241 | 487.1241 | 0.03877 | |
| Mannitol, 1 Acetyl, 3-hydroxy C18 | C₂₆H₅₀O₉ | 506.3455 | [M+H]⁺ | 507.3528 | 507.3530 | -0.44239 | 4 |
| | | | [M+NH₄]⁺ | 524.3793 | 524.3794 | -0.15207 | |
| | | | [M+Na]⁺ | 529.3347 | 529.3348 | -0.16194 | |
| Mannitol, 2 Acetyl, 3-hydroxy C18 | C₂₈H₅₂O₁₀ | 548.3560 | [M+H]⁺ | 549.3633 | 549.3633 | -0.04377 | 3 |
| | | | [M+NH₄]⁺ | 566.3899 | 566.3899 | -0.14042 | |
| | | | [M+Na]⁺ | 571.3453 | 571.3455 | -0.51428 | |
| Mannitol, 3 Acetyl, C18 (1 double bond) | C₃₀H₅₂O₁₀ | 572.3560 | [M+H]⁺ | 573.3633 | 573.3634 | -0.21665 | 5 |
| | | | [M+NH₄]⁺ | 590.3899 | ND | --- | |
| | | | [M+Na]⁺ | 595.3453 | ND | --- | |
| Mannitol, 3 Acetyl, 3-hydroxy C18 | C₃₀H₅₄O₁₁ | 590.3666 | [M+H]⁺ | 591.3739 | 591.3741 | -0.37943 | 4 |
| | | | [M+NH₄]⁺ | 608.4004 | 608.4005 | -0.13043 | |
| | | | [M+Na]⁺ | 613.3558 | 613.3557 | 0.19748 | |
| Mannitol, 3 Acetyl, 3-methoxy C18 | C₃₁H₅₆O₁₁ | 604.3823 | [M+H]⁺ | 605.3895 | ND | --- | 4 |
| | | | [M+NH₄]⁺ | 622.4161 | 622.4160 | 0.30351 | |
| | | | [M+Na]⁺ | 627.3715 | 627.3714 | 0.19524 | |
| Mannitol, 4 Acetyl, 3-hydroxy C18 | C₃₂H₅₆O₁₂ | 632.3772 | [M+H]⁺ | 633.3845 | 633.3846 | -0.19609 | 5 |
| | | | [M+NH₄]⁺ | 650.4110 | 650.4113 | -0.43803 | |
| | | | [M+Na]⁺ | 655.3664 | 655.3667 | -0.44394 | |

FIG. 5

| Compounds | Formula | Exact Mass | Ion Species | Exact Ion Mass m/z | Measured Ion Mass m/z | Mass Accuracy (ppm) | DBE |
|---|---|---|---|---|---|---|---|
| Arabitol, 0 Acetyl, 3-hydroxy C18 | C₂₃H₄₆O₇ | 434.3244 | [M+H]⁺ | 435.3316 | ND | --- | 1 |
| | | | [M+NH₄]⁺ | 452.3582 | ND | --- | |
| | | | [M+Na]⁺ | 457.3136 | 457.3137 | -0.18860 | |
| Arabitol, 1 Acetyl, 3-hydroxy C18 | C₂₅H₄₈O₈ | 476.3349 | [M+H]⁺ | 477.3422 | ND | --- | 2 |
| | | | [M+NH₄]⁺ | 494.3687 | 494.3688 | -0.16183 | |
| | | | [M+Na]⁺ | 499.3241 | 499.3241 | 0.02978 | |
| Arabitol, 2 Acetyl, 3-hydroxy C18 | C₂₇H₅₀O₉ | 518.3455 | [M+H]⁺ | 519.3528 | 519.3529 | -0.33922 | 3 |
| | | | [M+NH₄]⁺ | 536.3793 | 536.3795 | -0.34147 | |
| | | | [M+Na]⁺ | 541.3347 | 541.3349 | -0.35112 | |
| Arabitol, 3 Acetyl, C18 (1 double bond) | C₂₉H₅₂O₉ | 542.3455 | [M+H]⁺ | 543.3528 | 543.3527 | 0.14013 | 4 |
| | | | [M+NH₄]⁺ | 560.3793 | ND | --- | |
| | | | [M+Na]⁺ | 565.3347 | ND | --- | |
| Arabitol, 3 Acetyl, 3-hydroxy C18 | C₂₉H₅₄O₁₀ | 560.3560 | [M+H]⁺ | 561.3633 | 561.3635 | -0.39975 | 4 |
| | | | [M+NH₄]⁺ | 578.3899 | 578.3896 | 0.39796 | |
| | | | [M+Na]⁺ | 583.3453 | 583.3450 | 0.38904 | |
| Arabitol, 3 Acetyl, 2-methoxy C18 | C₃₀H₅₆O₁₀ | 574.3717 | [M+H]⁺ | 575.3790 | ND | --- | 4 |
| | | | [M+NH₄]⁺ | 592.4055 | 592.4055 | 0.07004 | |
| | | | [M+Na]⁺ | 597.3810 | 597.3810 | -0.14276 | |
| Arabitol, 4 Acetyl, 3-hydroxy C18 | C₃₁H₅₆O₁₁ | 602.3666 | [M+H]⁺ | 603.3739 | ND | --- | 4 |
| | | | [M+NH₄]⁺ | 620.4004 | 620.4005 | -0.17782 | |
| | | | [M+Na]⁺ | 625.3558 | 625.3561 | -0.46815 | |

FIG. 8

Potential acetylation sites
Positions $R_1$-$R_5$ = H or Ac
Potential combinations:
$_nC_r = n!/r!(n-r)!$
10 combinations for
3 acetyl groups on 5 sites
4 combinations for
3 acetyl groups on 4 sites
 (VIIb)
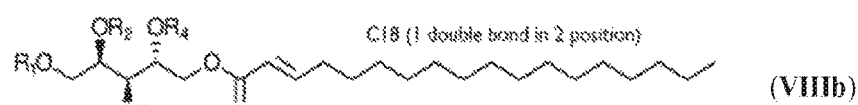 (VIIIb)
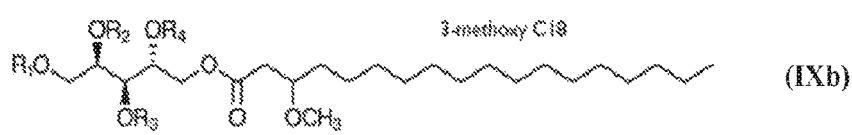 (IXb)
FIG. 10

| Compounds | Formula | Exact Mass | Ion Species | Exact Ion Mass m/z | Measured Ion Mass m/z | Mass Accuracy (ppm) | DBE |
|---|---|---|---|---|---|---|---|
| Mannitol, 0-Acetyl, 2-hydroxy C16 | C24H46O9 | 454.3036 | [M+H]+ | 455.3109 | ND | --- | 1 |
|  |  |  | [M+Na]+ | 454.2574 | ND | --- |  |
|  |  |  |  | 459.2988 | 459.2988 | -0.18794 |  |
| Mannitol, 1-Acetyl, 2-hydroxy C16 | C23H44O10 | 478.3142 | [M+H]+ | 478.3215 | ND | --- | 2 |
|  |  |  | [M+Na-L]+ | 496.3480 | 496.3484 | -0.78818 |  |
|  |  |  | [M+Na]+ | 501.3034 | 501.3033 | 0.24670 |  |
| Mannitol, 2-Acetyl, 3-hydroxy C16 | C28H50O10 | 530.3247 | [M+H]+ | 531.3320 | 531.3317 | 0.53044 | 3 |
|  |  |  | [M+Na-L]+ | 538.3586 | 538.3585 | 0.04420 |  |
|  |  |  | [M+Na]+ | 542.3140 | 542.3139 | 0.02459 |  |
| Mannitol, 3-Acetyl, C16 (1 double bond) | C29H52O9 | 544.3247 | [M+H]+ | 545.3320 | 545.3319 | 0.13962 | 5 |
|  |  |  | [M+Na-L]+ | 562.3586 | ND | --- |  |
|  |  |  | [M+Na]+ | 567.3140 | ND | --- |  |
| Mannitol, 3-Acetyl, 3-hydroxy C18 | C30H56O10 | 562.3353 | [M+H]+ | 563.3426 | 563.3427 | 0.22051 | 4 |
|  |  |  | [M+Na-L]+ | 580.3691 | 580.3694 | -0.45318 |  |
|  |  |  | [M+Na]+ | 585.3245 | 585.3244 | 0.67931 |  |
| Mannitol, 2-Acetyl, 3-strawberry C18 | C32H50O10 | 578.3510 | [M+H]+ | 577.3582 | ND | --- | 4 |
|  |  |  | [M+Na-L]+ | 594.3848 | ND | --- |  |
|  |  |  | [M+Na]+ | 599.3402 | 599.3400 | 0.37824 |  |
| Mannitol, 6-Acetyl, 3-hydroxy C18 | C32H56O11 | 604.3459 | [M+H]+ | 605.3532 | 605.3536 | 0.18510 | 5 |
|  |  |  | [M+Na-L]+ | 622.3797 | 622.3801 | -0.62181 |  |
|  |  |  | [M+Na]+ | 627.3351 | 627.3355 | 0.63359 |  |

FIG. 11

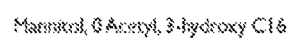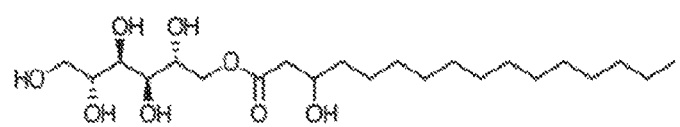
FIG. 12

| Compounds | Formula | Exact Mass | Ion Species | Exact Ion Mass m/z | Measured Ion Mass m/z | Mass Accuracy (ppm) | DBE |
|---|---|---|---|---|---|---|---|
| C16 compounds | | | | | | | |
| Arabitol, 0 Acetyl, 1-hydroxy C16 | C21H42O7 | 406.2931 | [M+H]+ | 407.3003 | ND | --- | 1 |
| | | | [M+NH4]+ | 424.3269 | ND | --- | |
| | | | [M+Na]+ | 429.2823 | 429.2823 | 0.0430 | |
| Arabitol, 1 Acetyl, 3-hydroxy C16 | C23H44O8 | 448.3036 | [M+H]+ | 449.3109 | ND | --- | 3 |
| | | | [M+NH4]+ | 466.3374 | 466.3375 | -0.17176 | |
| | | | [M+Na]+ | 471.2928 | 471.2924 | 0.48628 | |
| Arabitol, 3 Acetyl, 3-hydroxy C16 | C25H46O9 | 490.3142 | [M+H]+ | 491.3215 | ND | --- | 3 |
| | | | [M+NH4]+ | 508.3480 | 508.3478 | 0.41481 | |
| | | | [M+Na]+ | 513.3034 | 513.3033 | 0.37054 | |
| Arabitol, 3 Acetyl, C16 (1 double bond) | C25H46O8 | 514.3142 | [M+H]+ | 515.3215 | 515.3215 | -0.04868 | 5 |
| | | | [M+NH4]+ | 532.3480 | ND | --- | |
| | | | [M+Na]+ | 537.3034 | ND | --- | |
| Arabitol, 3 Acetyl, 3-hydroxy C16 | C27H48O10 | 532.3247 | [M+H]+ | 533.3320 | ND | --- | 4 |
| | | | [M+NH4]+ | 550.3586 | 550.3583 | 0.41882 | |
| | | | [M+Na]+ | 555.3139 | 555.3142 | 0.52975 | |
| Arabitol, 3 Acetyl, 3-methoxy C16 | C28H52O10 | 548.3404 | [M+H]+ | 549.3477 | ND | --- | 4 |
| | | | [M+NH4]+ | 564.3742 | 564.3747 | -0.87308 | |
| | | | [M+Na]+ | 569.3296 | 569.3295 | 0.21598 | |

FIG. 14

Potential acetylation sites
Positions $R_1$-$R_6$ = H or Ac
Potential combinations:
$_nC_r = n! / r! (n-r)!$
10 combinations for
3 acetyl groups on 5 sites
4 combinations for
3 acetyl groups on 4 sites
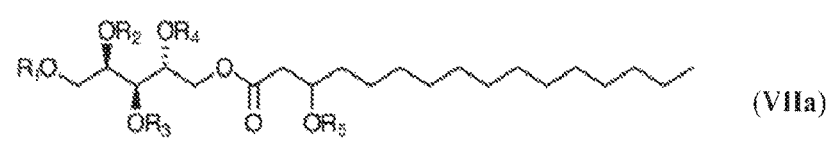
(VIIa)
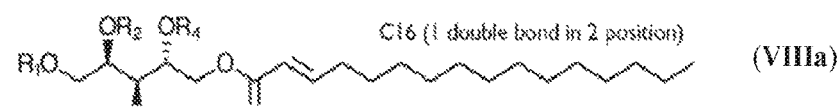
C16 (1 double bond in 2 position) (VIIIa)
3-methoxy C16 (IXa)
FIG. 16

| Compounds | Formula | Exact Mass | Ion Species | Exact Ion Mass m/z | Measured Ion Mass m/z | Mass Accuracy (ppm) | DBE |
|---|---|---|---|---|---|---|---|
| C18 fatty Acid series | | | | | | | |
| Mannitol, 2 Acetyl, 3-hydroxy C18 | C₂₈H₅₂O₁₀ | 548.3560 | [M+H]⁺ | 549.3633 | 549.3628 | -0.95358 | |
| | | | [M+NH₄]⁺ | 566.3899 | 566.3901 | -0.50515 | 3 |
| | | | [M+Na]⁺ | 571.3453 | 571.3456 | -0.69663 | |
| Mannitol, 3 Acetyl, 3-hydroxy C18 | C₃₀H₅₄O₁₁ | 590.3666 | [M+H]⁺ | 591.3739 | ND | ---- | |
| | | | [M+NH₄]⁺ | 608.4004 | 608.4006 | -0.29981 | 4 |
| | | | [M+Na]⁺ | 613.3558 | 613.3558 | 0.03049 | |
| Mannitol, 4 Acetyl, 3-hydroxy C18 | C₃₂H₅₆O₁₂ | 632.3772 | [M+H]⁺ | 633.3845 | ND | ---- | |
| | | | [M+NH₄]⁺ | 650.4110 | 650.4111 | -0.12176 | 5 |
| | | | [M+Na]⁺ | 655.3664 | 655.3669 | -0.76220 | |
| Mannitol, 5 Acetyl, C18 (1 double bond) | C₃₄H₅₆O₁₂ | 656.3772 | [M+H]⁺ | 657.3845 | 657.3844 | 0.11579 | |
| | | | [M+NH₄]⁺ | 674.4110 | ND | ---- | 7 |
| | | | [M+Na]⁺ | 679.3664 | ND | ---- | |
| Mannitol, 5 Acetyl, 3-hydroxy C18 | C₃₄H₅₈O₁₃ | 674.3877 | [M+H]⁺ | 675.3950 | ND | ---- | |
| | | | [M+NH₄]⁺ | 692.4216 | 692.4216 | -0.35903 | 6 |
| | | | [M+Na]⁺ | 697.3770 | 697.3775 | -0.88301 | |
| Mannitol, 5 Acetyl, 3-methoxy C18 | C₃₅H₆₀O₁₃ | 688.4034 | [M+H]⁺ | 689.4107 | ND | ---- | |
| | | | [M+NH₄]⁺ | 706.4372 | 706.4373 | -0.11185 | 6 |
| | | | [M+Na]⁺ | 711.3926 | 711.3923 | 0.46194 | |
| Mannitol, 6 Acetyl, 3-hydroxy C18 | C₃₆H₆₀O₁₄ | 716.3983 | [M+H]⁺ | 717.4056 | ND | ---- | |
| | | | [M+NH₄]⁺ | 734.4321 | 734.4318 | 0.45087 | 7 |
| | | | [M+Na]⁺ | 739.3875 | 739.3880 | 0.72306 | |
| C16 fatty Acid series | | | | | | | |
| Mannitol, 2 Acetyl, 3-hydroxy C16 | C₂₆H₄₈O₁₀ | 520.3247 | [M+H]⁺ | 521.3320 | ND | ---- | |
| | | | [M+NH₄]⁺ | 538.3586 | 538.3585 | 0.04420 | 3 |
| | | | [M+Na]⁺ | 543.3140 | 543.3141 | -0.34978 | |
| Mannitol, 3 Acetyl, 3-hydroxy C16 | C₂₈H₅₀O₁₁ | 562.3353 | [M+H]⁺ | 563.3426 | ND | ---- | |
| | | | [M+NH₄]⁺ | 580.3691 | 580.3689 | 0.39656 | 4 |
| | | | [M+Na]⁺ | 585.3245 | 585.3247 | -0.32365 | |
| Mannitol, 4 Acetyl, 3-hydroxy C16 | C₃₀H₅₂O₁₂ | 604.3459 | [M+H]⁺ | 605.3532 | ND | ---- | |
| | | | [M+NH₄]⁺ | 622.3797 | 622.3797 | 0.03806 | 5 |
| | | | [M+Na]⁺ | 627.3351 | 627.3354 | -0.46662 | |
| Mannitol, 5 Acetyl, C16 (1 double bond) | C₃₂H₅₂O₁₂ | 628.3459 | [M+H]⁺ | 629.3532 | 629.3534 | -0.35649 | |
| | | | [M+NH₄]⁺ | 646.3797 | ND | ---- | 7 |
| | | | [M+Na]⁺ | 651.3351 | ND | ---- | |
| Mannitol, 5 Acetyl, 3-hydroxy C16 | C₃₂H₅₄O₁₃ | 646.3564 | [M+H]⁺ | 647.3637 | ND | ---- | |
| | | | [M+NH₄]⁺ | 664.3903 | 664.3908 | -0.89270 | 6 |
| | | | [M+Na]⁺ | 669.3457 | 669.3457 | -0.12686 | |
| Mannitol, 5 Acetyl, 3-methoxy C16 | C₃₃H₅₆O₁₃ | 660.3721 | [M+H]⁺ | 661.3794 | ND | ---- | |
| | | | [M+NH₄]⁺ | 678.4059 | ND | ---- | 6 |
| | | | [M+Na]⁺ | 683.3613 | 683.3610 | 0.48155 | |
| Mannitol, 6 Acetyl, 3-hydroxy C16 | C₃₄H₅₆O₁₄ | 688.367 | [M+H]⁺ | 689.3743 | ND | ---- | |
| | | | [M+NH₄]⁺ | 706.4008 | 706.4010 | -0.25713 | 7 |
| | | | [M+Na]⁺ | 711.3562 | 711.3565 | -0.40967 | |

FIG. 19

| Compounds | Formula | Exact Mass | Ion Species | Exact Ion Mass m/z | Measured Ion Mass m/z | Mass Accuracy (ppm) | DBE |
|---|---|---|---|---|---|---|---|
| C18 Fatty Acid Series | | | | | | | |
| Arabitol, 2 Acetyl, 3-hydroxy C18 | C27H50O9 | 518.3455 | [M+H]+ | 519.3528 | ND | --- | 3 |
| | | | [M+NH4]+ | 536.3793 | 536.3789 | 0.81606 | |
| | | | [M+Na]+ | 541.3347 | 541.3347 | 0.03473 | |
| Arabitol, 3 Acetyl, 3-hydroxy C18 | C29H52O10 | 560.3560 | [M+H]+ | 561.3633 | ND | --- | 4 |
| | | | [M+NH4]+ | 578.3899 | 578.3895 | 0.57642 | |
| | | | [M+Na]+ | 583.3453 | 583.3449 | 0.56750 | |
| Arabitol, 4 Acetyl, C18 (1 double bond) | C31H54O10 | 584.356 | [M+H]+ | 585.3633 | 585.3635 | -0.38333 | 6 |
| | | | [M+NH4]+ | 602.3899 | ND | --- | |
| | | | [M+Na]+ | 607.3453 | ND | --- | |
| Arabitol, 4 Acetyl, 3-hydroxy C18 | C31H54O11 | 602.3666 | [M+H]+ | 603.3739 | ND | --- | 5 |
| | | | [M+NH4]+ | 620.4004 | 620.4004 | 0.03818 | |
| | | | [M+Na]+ | 625.3558 | 625.3563 | -0.80018 | |
| Arabitol, 4 Acetyl, 3-methoxy C18 | C32H56O11 | 616.3822 | [M+H]+ | 617.3895 | ND | --- | 5 |
| | | | [M+NH4]+ | 634.4161 | 634.4158 | 0.04850 | |
| | | | [M+Na]+ | 639.3715 | 639.3718 | -0.4573 | |
| Arabitol, 5 Acetyl, 3-hydroxy C18 | C33H56O12 | 644.3772 | [M+H]+ | 645.3845 | ND | --- | 6 |
| | | | [M+NH4]+ | 662.4110 | 662.4112 | -0.27468 | |
| | | | [M+Na]+ | 667.3664 | 667.3666 | -0.28244 | |
| C16 Fatty Acid Series | | | | | | | |
| Arabitol, 2 Acetyl, 3-hydroxy C16 | C25H46O9 | 490.3142 | [M+H]+ | 491.3215 | ND | --- | 3 |
| | | | [M+NH4]+ | 508.3480 | ND | --- | |
| | | | [M+Na]+ | 513.3034 | 513.3033 | 0.24066 | |
| Arabitol, 3 Acetyl, 3-hydroxy C16 | C27H48O10 | 532.3247 | [M+H]+ | 533.3320 | ND | --- | 4 |
| | | | [M+NH4]+ | 550.3586 | 550.3582 | 0.60677 | |
| | | | [M+Na]+ | 555.3140 | 555.3139 | 0.03381 | |
| Arabitol, 4 Acetyl, C16 (1 double bond) | C29H50O10 | 556.3247 | [M+H]+ | 557.3320 | 557.3320 | 0.04314 | 6 |
| | | | [M+NH4]+ | 574.3586 | ND | --- | |
| | | | [M+Na]+ | 579.3140 | ND | --- | |
| Arabitol, 4 Acetyl, 3-hydroxy C16 | C29H50O11 | 574.3353 | [M+H]+ | 575.3426 | ND | --- | 5 |
| | | | [M+NH4]+ | 592.3691 | 592.3695 | -0.65641 | |
| | | | [M+Na]+ | 597.3245 | 597.3248 | -0.49100 | |
| Arabitol, 4 Acetyl, 3-methoxy C16 | C30H52O11 | 588.3510 | [M+H]+ | 589.3583 | ND | --- | 5 |
| | | | [M+NH4]+ | 606.3848 | 606.3847 | 0.32906 | |
| | | | [M+Na]+ | 611.3402 | 611.3401 | 0.20058 | |
| Arabitol, 5 Acetyl, 3-hydroxy C16 | C31H52O12 | 616.3459 | [M+H]+ | 617.3532 | ND | --- | 6 |
| | | | [M+NH4]+ | 634.3797 | 634.3795 | 0.36181 | |
| | | | [M+Na]+ | 639.3351 | 639.3355 | -0.61978 | |

FIG. 20

| aHLB Values | Property | Examples of Selected Surfactant |
|---|---|---|
| <10 | Oil soluble | |
| >10 | Water Soluble | |
| 4-8 | Antifoaming agent | TERGITOL 15-S-3 |
| 7-11 | Water-in-oil emulsifier | TERGITOL 15-S-5 |
| 12-16 | Oil-in-water emulsifier | TERGITOL 15-S-7, 15-S-9, 15-S-12, 15-S-15 |
| 11-14 | Wetting agent | TERGITOL 15-S-7, 15-S-9 |
| 12-15 | Detergent | TERGITOL 15-S-7, 15-S-9, 15-S-12 |
| 16-20 | Stabilizer | TERGITOL 15-S-20, 15-S-30, 15-S-40 |

BIODEGRADABLE SURFACTANTS AND RELATED COMPOSITIONS, METHODS AND SYSTEMS

CROSS REFERENCE TO RELATED APPLICATIONS

The present application is the national stage of the international patent application No. PCT/US2018/017496 filed on Feb. 8, 2018 which in turn claims priority to U.S. Provisional Application No. 62/457,719, entitled "Biodegradable Surfactants and Related Compositions, Methods and Systems" filed on Feb. 10, 2017, the content of each of which is incorporated herein by reference in their entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

The present disclosure relates to biodegradable surfactants, particularly tunable biodegradable surfactants, and related compositions, methods, and systems.

BACKGROUND

Over the last few decades, there has been a constant drive towards environmentally friendly, biodegradable products including surfactants. The increasing purchasing power of the global consumers is the main driver of the surfactant industry.

Despite the efforts made to develop new technology, development of environmentally friendly biosurfactants is still challenging with particular reference to surfactants used in the personal care products, home care products, and industrial and institutional cleaner sectors, as well as in the food industry, textile industry, and oil industry.

SUMMARY

Provided herein are biodegradable surfactants, and related compositions, methods and systems, which in several embodiments can be tuned to a desired adjusted hydrophilic-lipophilic balance.

In particular provided herein is a biodegradable surfactant comprising
an amphiphilic heteroatom containing hydrocarbon comprising an hydrophilic head portion optionally comprising at least one counterion (Z) and a hydrophobic tail portion;
wherein the biodegradable surfactant has an aHLB value in accordance with equation (1):

$$aHLB = 20 * G_h/(G_h - G_t) \quad (1)$$

wherein $G_h$ is the Group Number of the head portion of the biodegradable surfactant, and $G_t$ is the Group Number of the tail portion of the biodegradable surfactant.

In particular, according to a first aspect, a biodegradable surfactant is described, the biodegradable surfactant comprises the amphiphilic heteroatom containing hydrocarbon of Formula (X) and optionally at least one counter ion Z:

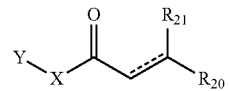

Formula (X)

wherein
⋯⋯ represents a single or double bond when R21 is H, and a single bond when R21 is other than H;
X is selected from one of O, NH, or NCH$_3$;
Y is selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups, optionally substituted with 1-6 tuning moieties independently selected from sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy;
R20 is a C11-C21 linear or branched alkyl, alkenyl, or alkynyl group;
R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and
wherein Z is a counterion selected to maintain an electric neutrality of the biodegradable surfactant, and can be selected from the group consisting of proton, ammonium, C1-C4 tetraalkyl ammonium, sodium (I), potassium (I), cesium (I), magnesium (II), calcium (II), zinc (II), inorganic sulfate (SO$_4^{2-}$), inorganic phosphate (PO$_4^{3-}$), tetrafluoroborate, hexafluorophospate, p-toluenesulfonate, benzenesulfonate, nitrate, trifluoroacetate, fluoride, chloride, bromide, and iodide or any combinations thereof.

According to a second aspect, a tunable biodegradable surfactant is described, the tunable biodegradable surfactant comprises an amphiphilic heteroatom containing hydrocarbon of Formula (XX) and optionally at least one counter ion Z:

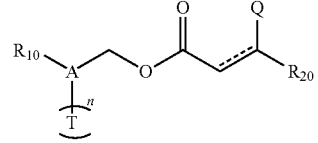

Formula (XX)

wherein
⋯⋯ represents a single or double bond when Q is H, and a single bond when Q is other than H;
n is 1-6;
A is a node moiety selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups,
T is a tuning moiety each independently selected from OH, or NH$_2$;
Q is selected from H, OH, or NH$_2$;
R10 is H, or C1-C2 alkyl group;
R20 is a C11-C21 linear or branched alkyl, alkenyl, or alkynyl group; and wherein Z is a counterion selected to maintain an electric neutrality of the biodegradable surfactant, and can be selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

In some embodiments, a tunable biodegradable surfactant is described, the tunable biodegradable surfactant comprises an amphiphilic heteroatom containing hydrocarbon of Formula (XXI) and optionally at least one counter ion Z:

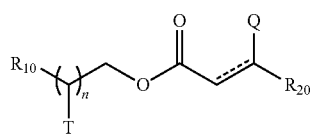

Formula (XXI)

wherein
- - - - - represents a single or double bond when Q is H, and a single bond when Q is other than H;
n is 1-6,
T is a tuning moiety each independently selected from OH, or $NH_2$;
Q is selected from H, OH, or $NH_2$;
R10 is H, or C1-C2 alkyl group; and
R20 is a C11-C21 linear or branched alkyl, alkenyl, or alkynyl group; and
wherein Z is a counterion selected to maintain an electric neutrality of the biodegradable surfactant, and can be selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

According to a third aspect, a method of providing a tunable biodegradable surfactant is described. The method comprises causing expression in a medium of an amphiphilic heteroatom containing hydrocarbon comprising an hydrophilic head portion and an hydrophobic tail portion, the expression performed by a cell configured to produce said amphiphilic heteroatom containing hydrocarbon in the cell, thus providing an expressed tunable biodegradable surfactant. The method can further comprise isolating the expressed tunable biodegradable surfactant from the medium thus providing the tunable biodegradable surfactant. In some embodiments, the cell configured to produce the amphiphilic heteroatom containing hydrocarbon is a cell genetically engineered to inactivate, the expression of at least one enzyme responsible for transformation of a tuning moiety of the amphiphilic hydrocarbon. In some embodiments the at least one enzyme comprises one or more enzymes capable of performing acetylation, deacetylation, hydroxylation, dihydroxylation, phosphorylation, sulfation and any other reactions identifiable to a person of skill in the art of tunable surfactant compounds. In some embodiments, inactivation of the enzyme can be performed by deleting, modifying, altering, silencing, inhibiting, or inactivating in any other manner known to a person skilled in the art. In some embodiments the expressed tunable surfactant is modified to have a desired hydrophilic-lipophilic balance according to methods herein described. In some embodiments the expressed tunable biodegradable surfactant is modified to have a desired hydrophilic-lipophilic balance according to methods herein described.

According to a fourth aspect, a method is described to provide a tunable biodegradable surfactant compound according to the present disclosure. The method comprises performing a coupling reaction between a hydrophilic compound and a hydrophobic compound, the hydrophilic compound configured to provide a hydrophilic portion of the tunable biodegradable surfactant and the hydrophobic compound configured to provide a hydrophobic portion of the tunable biodegradable surfactant. In the method, the hydrophilic compound presents a hydroxy or amine group and the hydrophobic compound presents a carboxyl group and the coupling reaction is performed for a time and under condition to allow formation of a covalent bond between the hydroxyl or amine group of the hydrophilic compound and the carboxyl group of the hydrophobic compound. In some embodiments the tunable biodegradable surfactant so obtained, is further modified to have a desired hydrophilic-lipophilic balance according to methods herein described.

According to a fifth aspect, a tuned biodegradable surfactant is described, the tuned biodegradable surfactant comprises an amphiphilic substituted hydrocarbon of Formula (XXII) and optionally at least one counter ion Z:

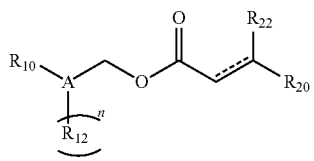

Formula (XXII)

wherein
- - - - - represents a single or double bond when R22 is H, and a single bond when R22 is other than H;
n is 1-6;
A is a node moiety selected from a C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups;
wherein the R22 and each of R12 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy;
R10 is H, or C1-C2 alkyl group; and
R20 is a C11-C21 linear or branched alkyl, alkenyl, or alkynyl group; and
wherein Z is a counterion selected to maintain an electric neutrality of the biodegradable surfactant, and can be selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluorborate, hexafluorophospate, p-toluenesulfonate, benzenesulfonate, nitrate, trifluoroacetate, fluoride, chloride, bromide, and iodide or any combinations thereof.

In some embodiments, the tuned biodegradable surfactant comprises an amphiphilic substituted hydrocarbon of Formula (XXIII) and optionally at least one counter ion Z:

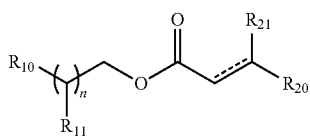

Formula (XXIII)

wherein

----- represents a single or double bond when R21 is H, and a single bond when R21 is other than H;

n is 1-6;

wherein the R21 and each of R11 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy;

R10 is H, or C1-C2 alkyl group;

R20 is a C11-C21 linear or branched alkyl, alkenyl, or alkynyl group; and wherein Z is a counterion selected to maintain an electric neutrality of the biodegradable surfactant, and can be selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluorborate, hexafluorophospate, p-toluenesulfonate, benzenesulfonate, nitrate, trifluoroacetate, fluoride, chloride, bromide, and iodide or any combinations thereof.

According to a sixth aspect, a method of controlling the hydrophilic-hydrophobic balance of a biodegradable surfactant is described. The method comprises providing a tunable biodegradable surfactant having a first aHLB, the tunable biodegradable surfactant comprising at least one tuning moiety. The method further comprises modifying the at least one tuning moiety to obtain a tuned biodegradable surfactant, wherein the tuned biodegradable moiety is selected to provide a tuned biodegradable surfactant having a second aHLB different from the first aHLB.

In some embodiments, the at least one tunable moiety is comprised in a head portion of a tunable biodegradable surfactant compound. Accordingly, the Group Number Gt of the tunable biodegradable surfactant compound is the same as the Group Number Gt of the tuned biodegradable surfactant compound.

According to a seventh aspect, a composition is described, the composition comprising a biodegradable surfactant of the disclosure together with at least one additive and/or at least one carrier.

According to an eighth aspect, a system to control the hydrophilic-hydrophobic balance of a biodegradable surfactant is described. The system comprises one or more biodegradable surfactants herein described presenting one or more tunable moieties, and one or more reagents capable of modifying one or more tunable moiety of the one or more biodegradable surfactants.

According to a ninth aspect, a method of separating a target organic compound from a substrate is described. The method comprises contacting a biodegradable surfactant herein described with a substrate comprising the target organic compound selected from a volatile organic compound, a halogenated volatile organic compound and a polyaromatic hydrocarbon. The method further comprises agitating the substrate comprising the target organic compound and the biodegradable surfactant for a time and under condition allowing formation of a mixture of at least two phases, thus separating at least in part the target organic compound from the substrate.

Biodegradable surfactants and related compositions methods and systems herein described, can be used in connection with various applications wherein controlled hydrophilic-hydrophobic balance of a surfactant is desired. For example, biodegradable surfactants and related compositions, methods and systems herein described can be used to provide surfactants with controlled wetting property, cleaning property, emulsifying/de-emulsifying property, dispersant property, and micellization property in various applications in several fields including petroleum, cosmetics, pharmaceutical, detergents, paint, and food industries and in additional fields identifiable by a skilled person upon reading of the present disclosure.

The details of one or more embodiments of the disclosure are set forth in the accompanying drawings and the description below. Other features, objects, and advantages will be apparent from the description and the drawings.

BRIEF DESCRIPTION OF DRAWINGS

The accompanying drawings, which are incorporated into and constitute a part of this specification, illustrate one or more embodiments of the present disclosure and, together with the detailed description and the examples, serve to explain the principles and implementations of the present disclosure.

In FIG. 3, biosurfactant compounds were purified using solid phase extraction (reversed phase), and eluted from the column using 100% methanol as detected by LC-MS analysis. The graph shows exemplary abundance of purified compounds in SPE as a function of retention time. In FIG. 4, the organic solvent was subsequently evaporated, and the dried material was digested with methanolic HCl, derivatized (silylated), and analyzed by gas chromatography-mass spectrometry. The graph shows abundance of compounds as a function of retention time. GC-MS analysis revealed that the biosurfactant mixture was composed of glycolipids containing the sugar alcohols mannitol and arabitol (TMS derivatives), as well six main fatty acid constituents: 3-hydroxystearic acid (C18:0), 3-hydroxypalmitic acid (C16:0), 3-methoxystearic acid (C18:0), 3-methoxypalmitic acid (C16:0), octadecenoic acid (C18:1, double bond in 2 position), and hexadecenoic acid (C16:1, double bond in 2 position). Mannitol and 3-hydroxystearic acid (C18:0) were notably the most abundant constituents in the mixture. The less abundant constituents are shown in detail in the inset graph. The mass spectra and retention times were confirmed through a comparison with authentic standards.

FIGS. 5-7 show that mannitol 3-hydroxy C18 compounds exist as an acetylation series. The Table in FIG. 5 shows exemplary results of high-resolution mass spectrometry that confirmed non-acetylated and acetylated mannitol 3-hydroxy C18 congeners in the spent liquid medium, with compounds containing three acetyl groups being the most abundant in the mixture. The 3-methoxy and unsaturated fatty acid versions of these compounds were also detected. It is noteworthy that the calculated formulae also match the double bond equivalents (DBE) for the proposed structures (shown in FIG. 6 and FIG. 7). In FIG. 7, the potential acetylation sites ("R") are highlighted on the different mannitol C18 congeners, as well as the potential number of structural combinations that exist for 3 acetyl groups—the most abundant type of mannitol 3-hydroxy C18. The factorial equation $_nC_r=n!/r!(n-r)!$ was used to calculate the number of potential acetylation combinations, with "n" representing the potential number of acetylation sites and "r" representing the number of acetyl groups.

FIGS. 8-10 show that arabitol 3-hydroxy C18 exists as an acetylation series. The Table in FIG. 8 shows exemplary results of high-resolution mass spectrometry that confirmed non-acetylated and acetylated arabitol 3-hydroxy C18 congeners in the spent liquid medium, with compounds containing three acetyl groups being the most abundant in the mixture. The 3-methoxy and unsaturated fatty acid versions of these compounds were also detected. The calculated formulae also match the double bond equivalents (DBE) for the proposed structures (shown in FIG. 9 and FIG. 10). In FIG. 10, the potential acetylation sites ("R") are highlighted on the different arabitol C18 congeners, as well as the potential number of structural combinations that exist for 3 acetyl groups—the most abundant type of arabitol 3-hydroxy C18. The factorial equation $_nC_r=n!/r!(n-r)!$ was used to calculate the number of potential acetylation combinations, with "n" representing the potential number of acetylation sites and "r" representing the number of acetyl groups.

FIGS. 11-13 show that mannitol 3-hydroxy C16 exists as an acetylation series. The Table in FIG. 11 shows exemplary results of high-resolution mass spectrometry that confirmed non-acetylated and acetylated mannitol 3-hydroxy C16 congeners in the spent liquid medium, with compounds containing three acetyl groups being the most abundant in the mixture. The 3-methoxy and unsaturated fatty acid versions of these compounds were also detected. The calculated formulae also match the double bond equivalents (DBE) for the proposed structures (shown in FIG. 12 and FIG. 13). In FIG. 13, the potential acetylation sites ("R") are highlighted on the different mannitol C16 congeners, as well as the potential number of structural combinations that exist for 3 acetyl groups. The factorial equation $_nC_r=n!/r!(n-r)!$ was used to calculate the number of potential acetylation combinations, with "n" representing the potential number of acetylation sites and "r" representing the number of acetyl groups.

FIGS. 14-16 show that arabitol 3-hydroxy C16 exists as an acetylation series. The Table in FIG. 14 shows exemplary results of high-resolution mass spectrometry that confirmed non-acetylated and acetylated arabitol 3-hydroxy C16 congeners in the spent liquid medium, with compounds containing three acetyl groups being the most abundant in the mixture. The 3-methoxy and unsaturated fatty acid versions of these compounds were also detected. The calculated formulae also match the double bond equivalents (DBE) for the proposed structures (shown in FIG. 15 and FIG. 16). In FIG. 16, the potential acetylation sites ("R") are highlighted on the different arabitol C16 congeners, as well as the potential number of structural combinations that exist for 3 acetyl groups. The factorial equation $_nC_r=n!/r!(n-r)!$ was used to calculate the number of potential acetylation combinations, with "n" representing the potential number of acetylation sites and "r" representing the number of acetyl groups.

In FIG. 17, *R. babjevae* biosurfactants were purified using solid phase extraction (reversed phase), and eluted from the column using 100% methanol as detected by LC-MS analysis. The graph shows exemplary abundance of compounds as a function of elution time. *R. babjevae* compounds are illustrated in the light gray LC-MS total ion chromatogram, and are overlayed with the LC-MS total ion chromatogram from *R. taiwanensis* (black trace). *R. babjevae* biosurfactants are markedly more hydrophobic as demonstrated by their longer retention time on the C18 column (i.e. shift to the right, arrow). In FIG. 18, the organic solvent from the *R. babjevae* eluate was subsequently evaporated, and the dried material was digested with methanolic HCl, derivatized (silylated), and analyzed by gas chromatography-mass spectrometry. The graph shows exemplary abundance of compounds as a function of elution time. Interestingly, the GC-MS analysis revealed that the biosurfactant mixture was composed of the same sugar alcohol and fatty acid constituents as *R. taiwanensis*, but at different ratios. The GC-MS total ion chromatograms (between the two samples) were normalized for mannitol concentration, and the ratios of the other constituents were relative to it.

FIG. 19 shows that mannitol fatty acid ester compounds produced by *R. babjevae* are hyper-acetylated. The Table in FIG. 19 shows exemplary results of high-resolution mass spectrometry that confirmed highly-acetylated mannitol congeners in the spent liquid medium, with compounds containing five acetyl groups being the most abundant in the mixture. The 3-methoxy and unsaturated fatty acid versions of these compounds were also detected.

FIG. 20 shows that arabitol fatty acid ester compounds produced by *R. babjevae* are hyper-acetylated. The Table in FIG. 20 shows exemplary results of high-resolution mass spectrometry that confirmed highly-acetylated arabitol congeners in the spent liquid medium, with compounds containing five acetyl groups being the most abundant in the mixture. The 3-methoxy and unsaturated fatty acid versions of these compounds were also detected.

DETAILED DESCRIPTION

Figure 1A:
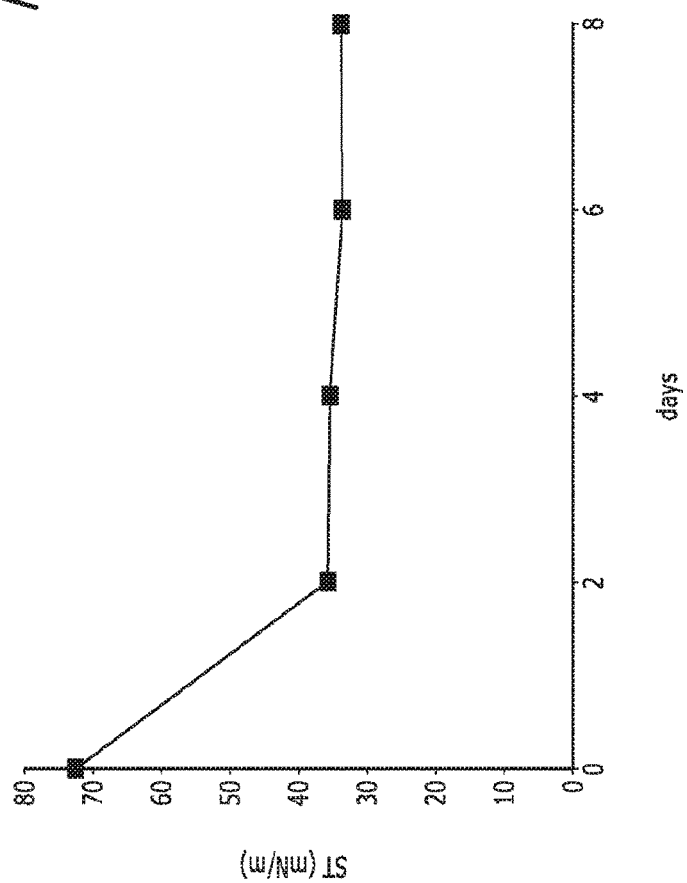
FIG. 1A shows a graph of exemplary growth medium surface tension (ST, in mN/m) measured over the time period shown for *R. bogoriensis*, which produced known sophorolipids that markedly reduced the surface tension of the culture medium.

Provided herein are biodegradable surfactants, and related compositions, methods and systems. In particular, the biodegradable surfactants are eco-friendly, e.g., can be degraded by microbes when released into the environment, and tunable, i.e. can be tuned for desired hydrophilic and hydrophobic properties. [1]

The term "surfactant" as used herein indicates compounds that lower the surface tension (or interfacial tension) between two liquids, between a liquid and a solid or between a liquid and a gas. Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group can extend out of the bulk water phase, into the air or into the oil phase, while the water-soluble head group remains in the water phase as will be understood by a skilled person. Surfactants can be used as detergents, wetting agents, emulsifiers, foaming agents, and dispersants and other applications identifiable by a skilled person. In particular surfactants can be surface active agents, which lower the surface tension between two liquids or a liquid and a gas. They can increase the solubility of organic compounds in water and increase the penetration of the solution onto a medium. Hence, surfactants act as an emulsifying agents and wetting agents. Surfactants are used in major world markets such as petroleum, cosmetics, pharmaceutical, detergents, paint, and food industries (Reis R S P, G. J.; Pereira, A. G.; Freire, D. M. G. 2013. Biosurfactants: Production and Applications. In Rosenkranz RCaF (ed), Biodegradation—Life of Science. InTech.). The applications of surfactants are determined based on their particular properties such as wetting property, cleaning property, emulsifying/de-emulsifying property, dispersant property, and micellization property.

Surfactants can be classified in cationic, anionic, zwitterionic and non-ionic surfactant based on the charge generated when dissolved in a solvent. Cationic surfactants generate positively charged ion when dissolved in any solvent. Examples of cationic surfactants comprise quaternary ammonium salts and others identifiable by a skilled person. Anionic surfactants generate negatively charged ion when dissolved in any solvent. Examples of anionic surfactants comprise alkyl sulfonates and others identifiable by a skilled person. Non-ionic surfactants do not ionize when dissolved in any solvent, hence, not ideal for hard water uses. Examples of non-ionic surfactants comprise alkyl ethoxylates and others identifiable by a skilled person. Amphoteric surfactants generate both positive and negative ions when dissolved in any solvent depending on the pH of the medium. Examples of amphoteric surfactants comprise betaines and others identifiable by a skilled person.

Surfactants can be manufactured from petroleum feed stock: ethylene, benzene, kerosene and n-paraffines are examples of primary feed stocks. Surfactants can also be manufactured from plant oils, and comprise biodegradable, environment friendly products; coconut oil and palm oil are examples of main feed stocks.

Surfactants are characterized based on their hydrophilic and hydrophobic properties which are indicated by a value of adjusted hydrophilic-lipophilic balance (aHLB) as will be understood by a skilled person. The more hydrophobic a molecule is, the lower the aHLB value. The more hydrophilic a molecule is, the higher the aHLB value it has. The general utility of surfactants is determined by their aHLB. The aHLB scale ranges from 0-20; surfactants that score >10 are more hydrophilic, and mediate oil-in-water emulsions (e.g. detergents and solubilizers), while those that score <10 are hydrophobic and mediate water-in-oil emulsions (e.g. wetting agents). This solubility property is an indicator of a surfactant's utility within an industrial process. Accordingly, for example antifoaming agents score 2-3, water/oil emulsifying agents score 3-6, wetting agents score 7-9, oil/water emulsifying agents score 8-16, detergents score 13-15, and solubilizing agents score 15-20.

In general, surfactants can be categorized in biodegradable surfactants (or biosurfactant, or green surfactants) and petroleum-based surfactants. Surfactants that are renewable and biodegradable in nature are known as green surfactants. On the other hand, surfactants produced from petroleum sources are not generally biodegradable and originate from non-renewable sources. Biodegradable surfactants are biodegradable and can be derived from organic and biological sources.

The term "biodegradable surfactant" refers to a type of surfactants that is degradable to at least two smaller fragments by bacteria, fungi as well as enzymes or other biological agents that are naturally present in a biological environment. A biodegradable surfactant can be derived from a biological source, or synthesized by chemical synthesis or by semisynthesis. A semisynthesis is a type of chemical synthesis that uses at least in part compounds isolated from biological sources (e.g. plant material or bacterial or cell cultures) other than petroleum or crude oil as starting materials. In particular, biodegradable surfactants can be produced by a variety of microorganisms, namely bacteria, yeast, and fungi [2, 3], by means of chemical synthesis or semisynthesis.

A biodegradable surfactant herein described comprises an amphiphilic heteroatom containing hydrocarbon (herein also indicated as biodegradable surfactant molecule) which comprises an hydrophilic head portion optionally comprising at least one counterion, and an hydrophobic tail portion;

The term "optionally" means that the described circumstance may or may not occur, so that the description includes instances where the circumstance occurs and instances where it does not. For example, the phrase "optionally comprising at least one counterion" means that a tunable moiety or a tuned moiety, may or may not be a charged group of atoms, the description includes structures wherein the tunable moiety or the tuned moiety may be present as polar and neutral group without Z or the tunable moiety or the tuned moiety may be present as a charged group with counterion Z to maintain electric neutrality.

Accordingly a biodegradable surfactant herein described comprises a biodegradable surfactant head portion formed by the hydrophilic head portion of the amphiphilic heteroatom containing hydrocarbon and optionally a counterion, and a biodegradable surfactant tail portion formed by the hydrophobic tail portion amphiphilic heteroatom containing hydrocarbon. In particular the head portion of a biodegradable surfactant as used herein refers to a contiguous terminal section of the substituted amphiphilic hydrocarbon that covers a maximum number of hydrophilic functional groups with positive Group Numbers, optionally including one or more counterions. Typically the head portion comprises a linear or cyclic C1-C20 hydrocarbon substituted with a C1-C15 hydrophilic group comprising a heteroatom such as O, N or combinations thereof. The tail portion of a biodegradable surfactant refers to contiguous terminal section of the substituted amphiphilic hydrocarbon that covers the maximum number of hydrophobic groups of atoms with negative Group Numbers. Typically, the tail portion comprises C1 to C30 hydrocarbons including quaternary C, tertiary CH, secondary $CH_2$, and primary $CH_3$, the valence of each of which can be satisfied, for example, by a covalent bond to another carbon atom. Typically the tail portion does not include heteroatoms or includes no more than four heteroatoms.

The term "heteroatom" as used herein indicates an atom other than carbon or hydrogen which is covalently bonded to a carbon atom as will be understood by a skilled person. In particular heteroatoms in the sense of the disclosure comprises an atom selected from the group consisting of boron, nitrogen, oxygen, silicon, sulfur, selenium, phosphorus, chlorine, bromine, and iodine, wherein the heteroatom is covalently bonded to a carbon atom of the amphiphilic hydrocarbon forming part of the surfactant.

The term "counterion" or "counter ion" as used in the present disclosure refers to a positive or negative ion of such charge character that an electric neutrality of the biodegradable surfactant is maintained.

The biodegradable surfactants herein described have hydrophilic and hydrophobic property as will be understood by a skilled person and can be measured using a Group number of the group of atoms moiety and/or molecules.

As used herein, the term "Group Number" indicates a designation by which the propensity of a given surfactant to show more hydrophilic or hydrophobic character. Thus, the group number describes the nature of the surfactant and it is an inclusive property of the ionic character of such (e.g. counterions involved) and can be used to indicate the relative hydrophilicity and lipophilicity of various chemical structural elements of a surfactant (including counterions associated with hydrophilic groups). The Group Number for a certain chemical moiety within a compound can be calculated based on a measured HLB value of the compound according to equation $$HLB = \Sigma(\text{hydrophilic group numbers}) + \Sigma(\text{lipophilic group numbers}) + 7 \quad (2)$$

wherein HLB indicates a Hydrophilic Lipophilic Balance of the compounds measurable through detection of a coalescence rate of the compound according to methods identifiable by a skilled person (see e.g. [4] [5] [6]) and wherein the lipophilic group can be CH, CH2, and/or CH3, and the hydrophilic group numbers represent the summation of the group numbers for the hydrophilic moieties in the amphiphilic compound.

An exemplary list of Group Numbers for a group of atoms including at least one counterion in the case of a charged group is shown in Table 1. (Davies J T (1957), supra) [4] [5] [6], wherein if the hydrophilic group in Table 1, is mentioned in connection with a chemical environment (e.g., free or sorbitan ring) the value of the Group Number is verified experimentally as described herein by measurement of HLB and using equation (2).

As illustrated in Table 1, the group of atoms associated with a Group Number is meant to be charge neutral and may include at least one counter ion Z wherein Z is selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluorborate, hexafluorophospate, p-toluenesulfonate, benzenesulfonate, nitrate, trifluoroacetate, fluoride, chloride, bromide, and iodide or any combinations thereof.

TABLE 1

Group Numbers of exemplary hydrophilic, lipophilic and derived groups[4]

| | Group Number |
|---|---|
| Hydrophilic groups | |
| —$SO_4^-Na^+$ | 38.7 |
| —$COO^-K^+$ | 21.1 |
| —$COO^-Na^+$ | 19.1 |
| N (tertiary amine) | 9.4 |
| Ester (sorbitan ring) | 6.8 |
| Ester (free) | 2.4 |
| —COOH | 2.1 |
| Hydroxyl (free) | 1.9 |
| —O— | 1.3 |
| Hydroxyl (sorbitan ring) | 0.5 |
| Lipophilic groups | |
| —CH— | |
| —$CH_2$— | |
| $CH_3$— | −0.475 |
| =CH— | |
| Derived groups | |
| —(CH2—CH2—O)— | +0.33 |
| —(CH2—CH2—CH2—O)— | −0.15 |

Based on the indications of Table 1 a hydrophilic group has a positive value of Group Number which is proportional to the hydrophilicity of the functional group. For example, sodium sulfate has a Group Number of 38.7 which is larger than that of hydroxyl group of 1.9. In contrast, a methyl group as a hydrophobic group has a Group Number of −0.475 which is more hydrophobic than trimethyleneoxy group which has a Group Number of −0.15, namely, less negative than that of methyl group.

It is further observed from Table 1 that in the case of the presence of a counter ion, the nature of counterion would affect the associated Group Number. For example, —$CO_2H$, —$CO_2Na$ and —$CO_2K$ each has a Group Number of 2.1, 19.1 and 21.1 respectively depending on the nature of counter ions $H^+$, $Na^+$, and $K^+$. A skilled person will be able to identify for a certain substituted amphiphilic hydrocarbon a counterion that provides a desired aHLB by methods and techniques identifiable by the skilled person.

In some embodiments, the Group Number of one or more moieties can be determined based on a detected HLB value of the compound comprising the moiety.

In some embodiments, wherein the Group Number of a moiety within a compound has already been determined, the Group Number of the moiety can be used to calculate the HLB value of the compound which can optionally be also confirmed experimentally (see e.g. techniques described in [4] [5] [6]). In particular in some embodiments, the HLB value of a compound can be experimentally detected and then the Group Number of hydrophilic moiety calculated based on equation (2) using the determined HLB value. Exemplary determination of HLB and Group Numbers are illustrated in the example section (see Example 15 and 16).

In biodegradable surfactants herein described, the hydrocarbon forming the biodegradable molecule is amphiphilic and therefore has both hydrophilic and hydrophobic parts. The term "hydrophobicity" refers to a physical property of a molecule or a group of atoms of the molecule to be unattractive to water as indicated by the related Group Number. In particular as used herein, a group of atoms including a tuning moiety, a tunable moiety, and a tuned moiety, is defined as being hydrophobic when the group of atoms has a Group Number less than zero. As used herein, the term hydrophobic and lipophilic are used interchangeably. For example, lipophilic groups —CH—, —CH2-, —CH3 and =CH— as listed in Table I all have Group Number of −0.475.

The term "hydrophilicity" refers to a physical property of a molecule or a group of atoms of the molecule to be attractive to water as can be indicated by the related Group Number. In particular. as used herein, a group of atoms including a tuning moiety, a tunable moiety, and a tuned moiety, is defined as being hydrophilic when the group of atoms has a Group Number greater than zero. For example, the hydrophilic groups as listed in Table I have Group Numbers between 0.5 and 38.7 for hydroxyl (sorbitan ring) and —$SO_4^-Na^+$ respectively.

The hydrophilicity or hydrophobicity of the head portion and tail portion each represents a summation of the hydrophilicity or hydrophobicity of all the constituting groups of atoms of the head portion and the tail portion respectively and optionally at least one counter ion of such charge character to maintain an electric neutrality of the biodegradable surfactant. A hydrophilic head portion refers to a greater than zero summation of the Group Numbers of all the constituting groups of atoms of the head portion. A hydrophobic tail portion refers to a less than zero summation of the Group Numbers of all the constituting groups of atoms of the tail portion.

The hydrophilic and hydrophobic properties can be experimentally determined as will be known by a person skilled in the art with knowledge of the disclosure as described herein. The terms lipophilic and hydrophobic are used interchangeably throughout the current disclosure.

The aHLB of a biodegradable surfactant can be calculated from equation (1) based on the chemical groups of the molecule:

$$aHLB = 20 * G_h/(G_h - G_t) \quad (1)$$

wherein $G_h$ is the Group Number of the head portion which has a positive value, and $G_t$ is the Group Number of the tail portion which has a negative value. As used herein, a Group Number (G) of a group of atoms is defined as a proportion of free energy of transfer of the group of atoms from water to a hydrocarbon liquid which can be calculated with methods described by Davies J T (1957) [4] and other methods identifiable by a skilled person upon reading of the present disclosure. Consequently, aHLB is a measure of relative hydrophilicity of a biodegradable surfactant head portion relative to that of the biodegradable surfactant as a whole.

Figures 27A, 27B:
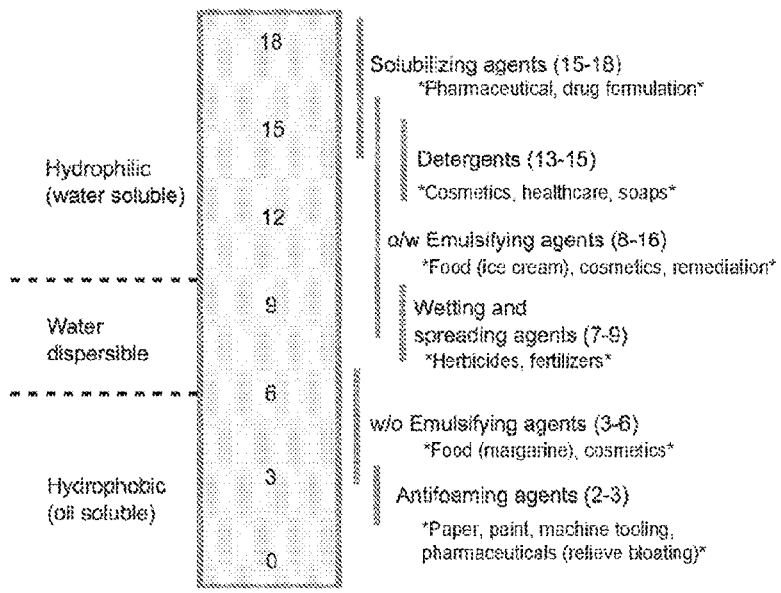
FIG. 27(A) shows a diagram illustrating examples of applications of surfactants based on their corresponding adjusted hydrophilic-lipophilic balance (aHLB) score.
FIG. 27(B) shows a table illustrating examples of applications of surfactants based on their corresponding adjusted hydrophilic-lipophilic balance (aHLB) score, wherein the TERGITOL™ 15-S series surfactants structure including TERGITOL™ 15-S-3, TERGITOL™ 15-S-5, TERGITOL™ 15-S-7, TERGITOL™ 15-S-9, TERGITOL™ 15-S-12, TERGITOL™ 15-S-20, TERGITOL™ 15-S-30, and TERGITOL™ 15-S-40 were available from the Dow Chemical Company having a general structural formula of $C_{12-14}H_{25-29}O[CH_2CH_2O]_xH$ (see website https://dowac.custhelp.com/app/answers/detail/a_id/1464/~/tergitol-15-s-series-surfactants-structure at the time of filing of the present disclosure).
Figure 27C:
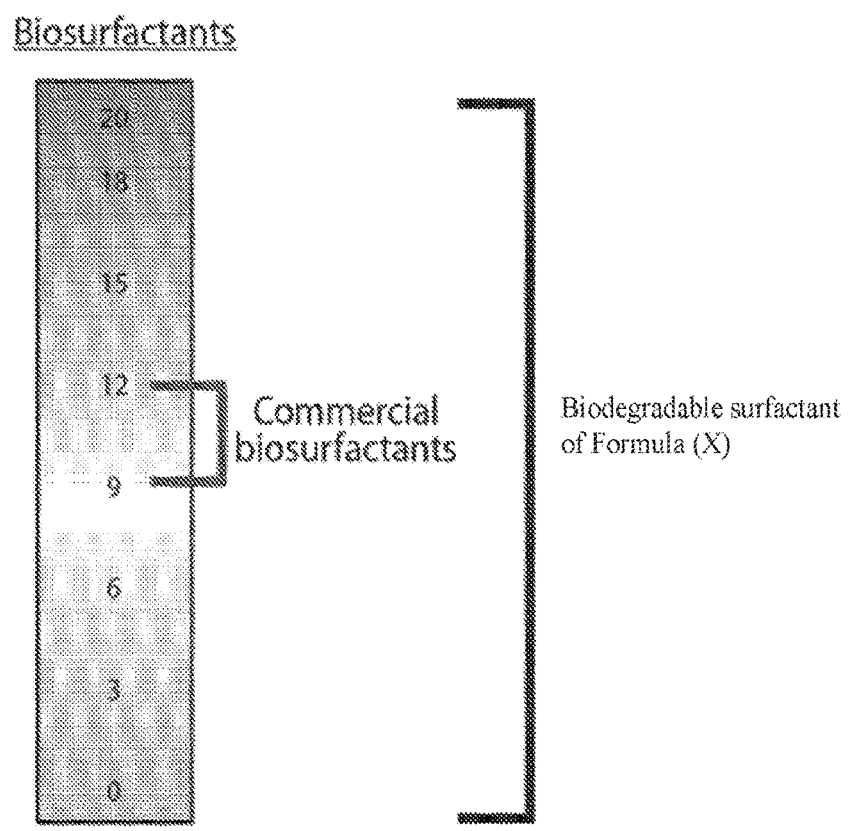
FIG. 27C shows a diagram illustrating a range of 0-20 of adjusted hydrophilic-lipophilic balance (aHLB) score for a biodegradable surfactant represented by Formula (X) as compared to 9-12 of adjusted hydrophilic-lipophilic balance (aHLB) score for commercial biosurfactants.
Figure 28:
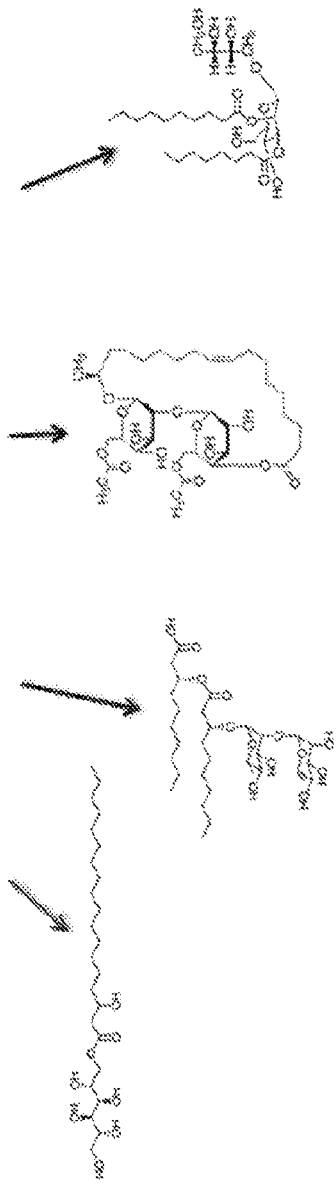
FIG. 28 shows a summary of characteristics and structural diagrams of the biosurfactant of the present disclosure compared to other selected biosurfactants in industrial use.

In particular as used herein, a hydrophilic biodegradable surfactant refers to a biodegradable surfactant that has an aHLB value of 10 or more. Thus a hydrophilic biodegradable surfactant would have a $G_h$ the Group Number of a head portion of the biodegradable surfactant, equal to or greater than the absolute value of $G_t$ the Group Number of a tail portion of the biodegradable surfactant according to equation (1). Correspondingly, a hydrophobic biodegradable surfactant refers to a biodegradable surfactant that has an aHLB value less than 10. Thus a hydrophobic biodegradable surfactant would have a $G_h$ the Group Number of a head portion of the biodegradable surfactant, less than the absolute value of $G_t$ the Group Number of a tail portion of the biodegradable surfactant according to equation (1). Exemplary applications for biodegradable surfactants as described herein can be on their corresponding adjusted hydrophilic-lipophilic balance (aHLB) score as shown in FIG. 27(A).

In some embodiments, the substituted amphiphilic hydrocarbon of a biodegradable surfactant as described herein comprises at least one amide and/or ester bond and can undergo amide bond or ester bond hydrolysis to provide the fatty acid along with the carbohydrate (e.g. mannitol) as the other degradation product. The fatty acid can be absorbed into an environment and broken down by organisms by at least one biological process (e.g. oxidation and citric acid cycle) to produce carbon-based building blocks for the reuse. Likewise, the carbohydrate moiety may be broken down through glycolysis and the smaller carbon building blocks reused for constructing macromolecules.

In some embodiments, a biodegradable surfactant described herein comprises an amphiphilic substituted hydrocarbon of Formula (X), and optionally at least one counter ion Z:

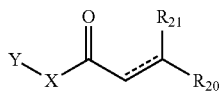

Fomula (X)

wherein

------- represents a single or double bond when R21 is H, and a single bond when R21 is other than H;

X is selected from one of O, NH, or NCH3;

Y is selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups, optionally substituted with 1-6 tuning moieties independently selected from sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy;

R20 is a C11-C21 linear or branched alkyl, alkenyl, or alkynyl group; and

R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy;

and wherein Z is selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

The term "alkyl" as used herein refers to a linear, branched, or cyclic saturated hydrocarbon group typically although not necessarily containing 1 to about 30 carbon atoms. A lower alky group as used herein refers to an alkyl group having 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. The term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

As used herein, an alkenyl group denotes an aliphatic hydrocarbon group containing at least one carbon-carbon double bond.

As used herein, an alkynyl group denotes an aliphatic hydrocarbon group containing at least one carbon-carbon triple bond.

As used herein, an aliphatic hydrocarbon refers to a non-aromatic hydrocarbon comprising carbon and hydrogen atoms.

In embodiments wherein R21 of Formula (X) is other than hydrogen, the head portion of Formula (X) is represented by Formula ($X_h$) and the tail portion is represented by Formula ($X_t$):

Formula ($X_h$)

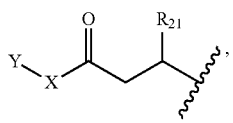

Formula ($X_t$)

In embodiments wherein R21 in Formula (X) is a hydrogen, the head portion of Formula (X) is represented by Formula ($X_{h'}$):

Formula ($X_{h'}$)

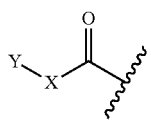

and the tail portion is represented by Formula ($X_{h'}$):

Formula ($X_{t'}$)

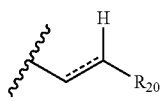

In some exemplary embodiments herein described, the aHLB of the biodegradable surfactant of Formula (X) can be calculated using equation (1), in which the Gh is the Group Number of Formula ($X_h$) and Gt is the Group Number of Formula ($X_t$). In other exemplary embodiments herein described, the aHLB of the biodegradable surfactant of Formula (X) can be calculated using equation (1), in which the Gh is the Group Number of Formula ($X_{h'}$) and Gt is the Group Number of Formula ($X_{t'}$).

Figure 25:
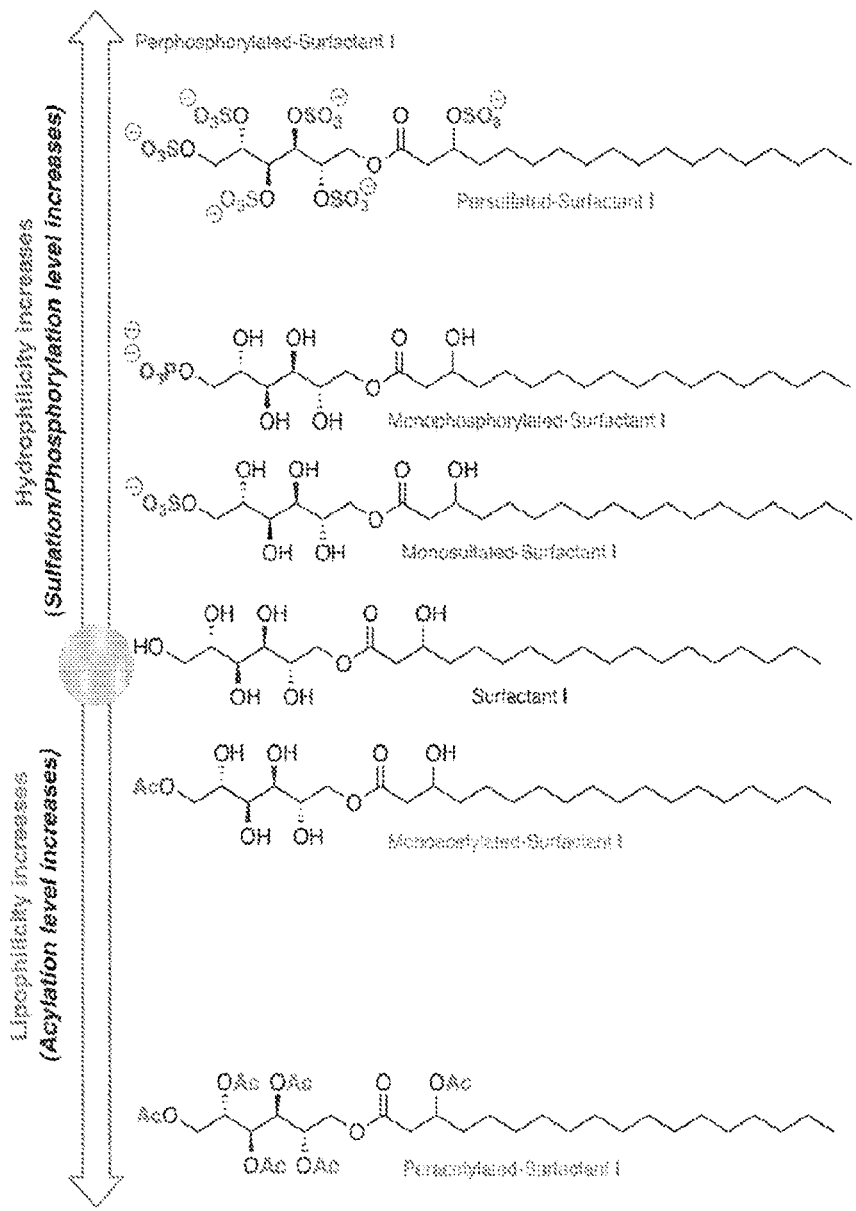
FIG. 25 shows a diagram of the effect of the degree of acetylation, sulfation or phosphorylation on surfactant I on its hydrophilicity/lipophilicity profile. Thus, incremental addition of acetyl groups would enhance the lipophilicity of surfactant I, while incremental addition of either sulfate or phosphate groups will result in its enhanced hydrophilicity. Here, 'Ac' represents an acetyl group, '$OSO_3^-$' represents a sulfate group, and '$OPO_3^{2-}$' represents a phosphoate group, wherein the anionic can have any of the counterions as described herein, including proton, ammonium, C-C4 tetraalkyl ammonium, sodium (I), potassium (I), cesium (I), magnesium (II), calcium (II), zinc (II), or any combinations thereof.
Figure 26:
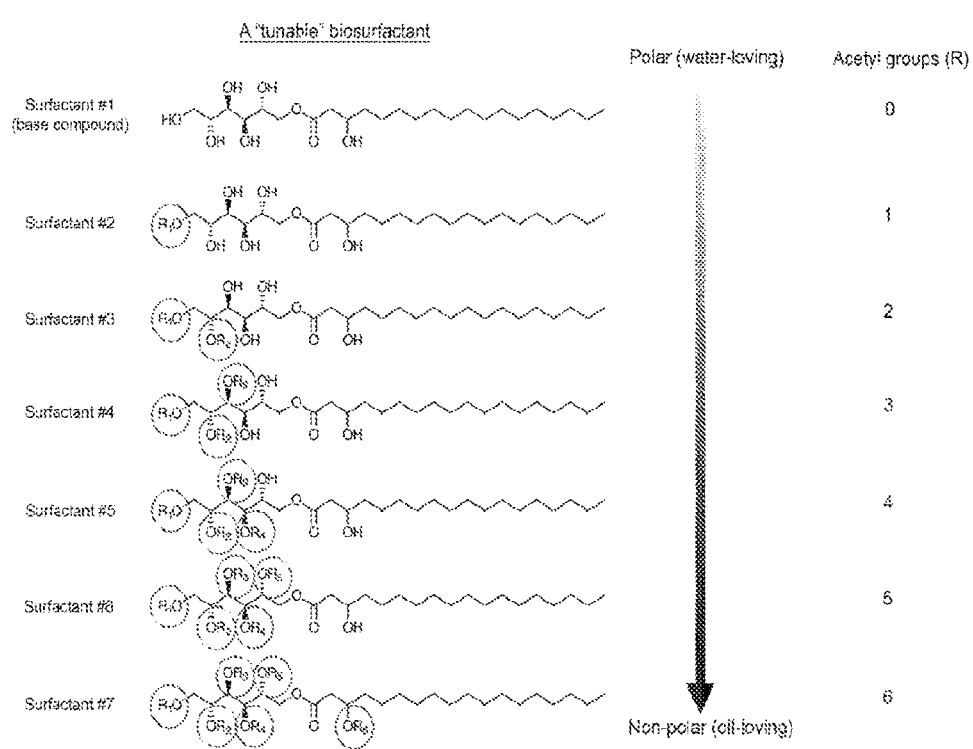
FIG. 26 shows in further detail the effect of incremental acetylation of a tunable surfactant as shown in FIG. 25. Shown is a diagram of an example of tunable surfactant, showing an unacetylated base compound (surfactant #1) and surfactant #2 to #7, comprising from 1 to 6 acetyl groups respectively, with increasing lipophilicity with addition of acetyl groups, 'tuning' the base compound from polar (water loving) to non-polar (oil loving). As shown herein, R represents acetyl groups, which are substituted for the hydrogen on the —OH groups on the head group and/or the carbon chain tail.

In some embodiments, a tunable biodegradable surfactant, can be "tuned" to cover the entire aHLB scale from 0-20 through modification of the head portion or the tail portion of the surfactant to achieve a $G_h$ number or a $G_t$ number associated with a desired aHLB value thus controlling the hydrophilic-hydrophobic balance of the biodegradable surfactant. As an example, FIG. 25 shows base surfactant I can be adjusted to persulfate surfactant I to have increased hydrophilicity on one hand. The same base surfactant I can be peracetylated on the other hand to have decreased hydrophilicity.

In some embodiments, a production process for a biodegradable surfactant can be "on-demand"; and the same base material or a tunable biodegradable surfactant will be utilized to make the "tuned" biosurfactant variants. For example, if there is a large request for biosurfactants with an aHLB of about 3 and about 13, a same base compound can be used with different modification pathways and tailored to the quantities requested.

In an exemplary embodiment, the biodegradable surfactant having Formula (X) can be Surfactant I represented as Formula (III) and also shown in FIG. 25.

Formula (III)

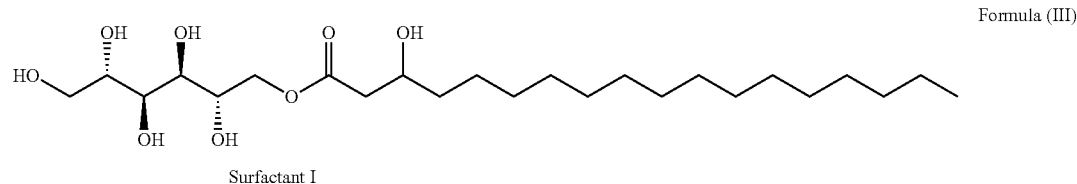 [SMILES: CCCCCCCCCCCCCCCC(O)CC(=O)OC[C@H](O)[C@H](O)[C@@H](O)[C@@H](O)CO]

Surfactant I

The aHLB value of Surfactant I of Formula (III) can be calculated based on the Group Number of Table 1.

The head portion of Surfactant I of Formula (III) has a Group Number $G_h$ of 10 (6*1.9+2.4−8*0.475) resulting from 6 hydroxyl groups (1.9), 8 CH or CH2 groups (−0.475), and one ester group (2.4).

Formula (III$_h$)

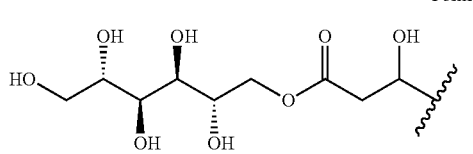

The tail portion for Surfactant I as represented by Formula (III$_t$) has a Group Number $G_t$ of −7.125 (−0.475*15) which results from 15 methylene group or methyl groups each having a group value of −0.475.

Formula (III$_t$)

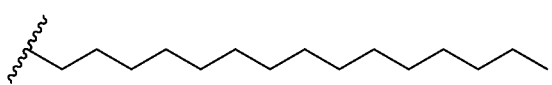

Therefore, according to equation (1), the aHLB for Surfactant I is 11.68 (20*10/(10+7.125)).

In some embodiments, a biodegradable surfactant has an aHLB value in a range selected from 0-20, preferably 10-20.

In some embodiments, the biodegradable surfactant herein described comprises one or more amphiphilic substituted hydrocarbons having a C16 fatty carboxyl group represented by general Formulas (IVa) to (IXa) as shown below.

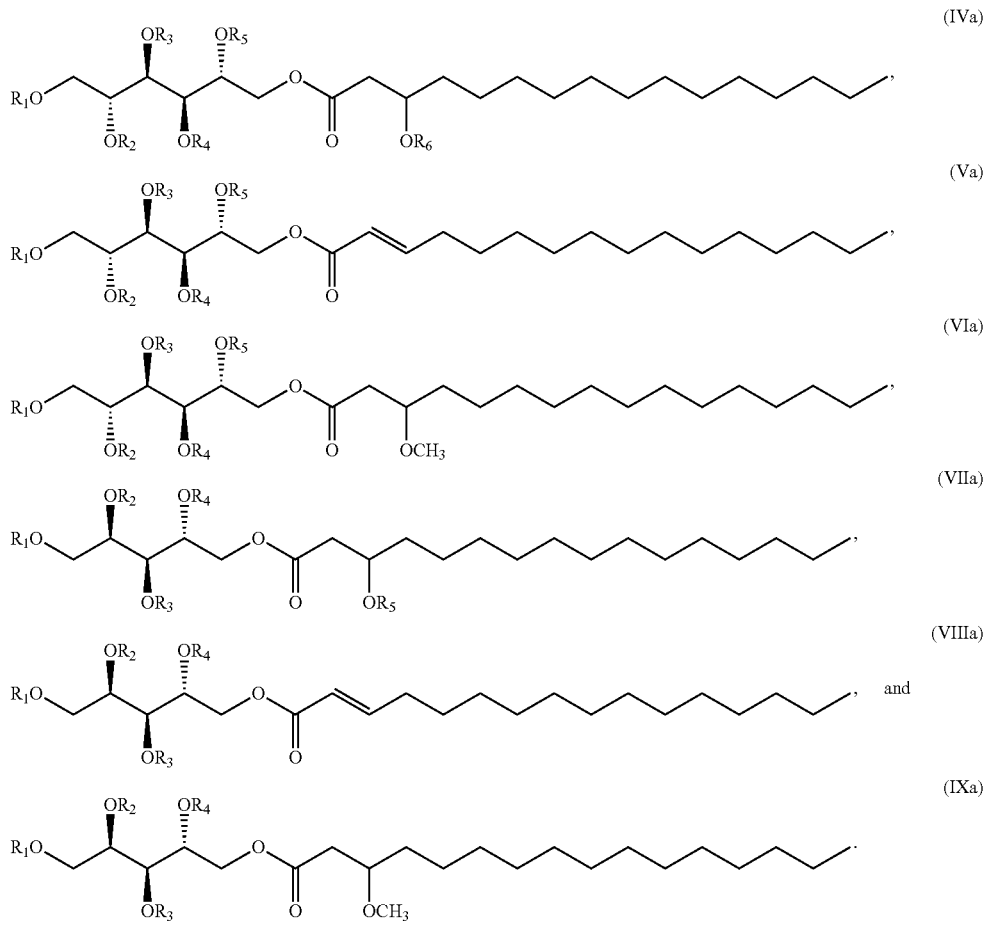
wherein OR1 to OR6 are independently selected from sulfate, phosphate, hydroxyl, acetyloxy, or C1-C2 alkoxy.
In some embodiments, the biodegradable surfactant herein described comprises one or more amphiphilic substituted hydrocarbons having a C18 fatty carboxyl group represented by general Formulas (IVb) to (IXb) as shown below.
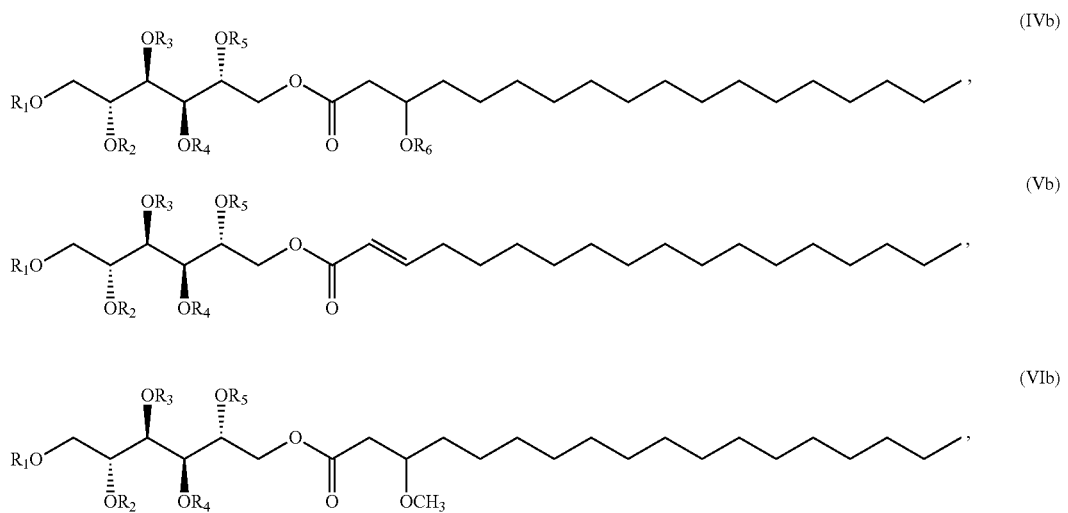

-continued

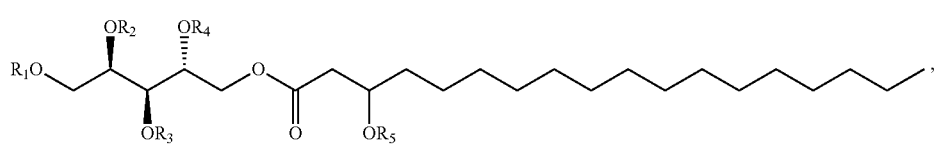
(VIIb)

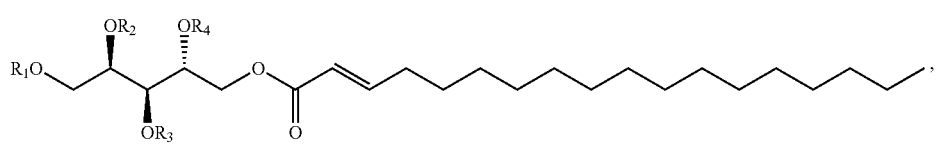
(VIIIb), and

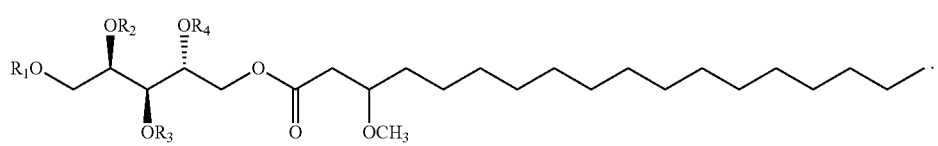
(IXb)

wherein OR1 to OR6 are independently selected from sulfate, phosphate, hydroxyl, acetyloxy, or C1-C2 alkoxy.

In some embodiments, the biodegradable surfactant herein described comprises one or more an amphiphilic substituted hydrocarbons of Formulas (XI) to (XVIII) shown below.

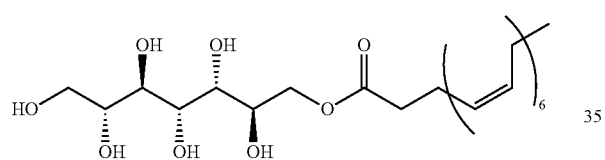

Formula (XI)

In particular Formula (XI) illustrates an exemplary neutral biodegradable surfactant that comprises an alkenyl group derived from alkenyl aliphatic fatty acid, namely, docosahexaenoic acid (DHA). The biodegradable surfactant having Formula (XI) can be produced by esterification of volemitol and docosahexaenoic acid (DHA).

Other neutral biodegradable surfactants can also be synthesized by esterification of a fatty acid selected from Myristic acid ($CH_3(CH_2)_{12}COOH$), Palmitic acid ($CH_3(CH_2)_{14}COOH$), Stearic acid ($CH_3(CH_2)_{16}COOH$) Arachidic acid ($CH_3(CH_2)_{18}COOH$), Behenic acid ($CH_3(CH_2)_{20}COOH$), Lignoceric acid ($CH_3(CH_2)_{22}COOH$) and 3-hydroxy octadecanoic acid, Myristoleic acid (CH3(CH2)3 CH=CH(CH2)7COOH), Palmitoleic acid ($CH_3(CH_2)_5CH=CH(CH_2)_7COOH$), Sapienic acid ($CH_3(CH_2)_8CH=CH(CH_2)_4COOH$), Oleic acid ($CH_3(CH_2)_7CH=CH(CH_2)_7COOH$), Elaidic acid ($CH_3(CH_2)_7CH=CH(CH_2)_7COOH$), Vaccenic acid ($CH_3(CH_2)_5CH=CH(CH_2)_9COOH$), Linoleic acid ($CH_3(CH_2)_4CH=CHCH_2CH=CH(CH_2)_7COOH$), Linoelaidic acid ($CH_3(CH_2)_4CH=CHCH_2CH=CH(CH_2)_7COOH$), α-Linolenic acid ($CH_3CH_2CH=CHCH_2CH=CHCH_2CH=CH(CH_2)_7COOH$), Arachidonic acid ($CH_3(CH_2)_4CH=CHCH_2CH=CHCH_2CH=CHCH_2CH=CH(CH_2)_3COOH$), Eicosapentaenoic acid ($CH_3CH_2CH=CHCH_2CH=CHCH_2CH=CHCH_2CH=CHCH_2CH=CH(CH_2)_3COOH$), Erucic acid ($CH_3(CH_2)_7CH=CH(CH_2)_{11}COOH$), and Docosahexaenoic acid ($CH_3CH_2CH=CHCH_2CH=CHCH_2CH=CHCH_2CH=CHCH_2CH=CHCH_2CH=CH$ ($CH_2)_2COOH$) with a polyol selected from Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Galactitol (6-carbon), Fucitol (6-carbon), Iditol (6-carbon), Inositol (6-carbon; a cyclic sugar alcohol), Volemitol (7-carbon) and $HOCH_2 (CHOH)_p CH_2OH$ wherein p is 0-5.

In some embodiments, the biodegradable surfactants herein described comprise a zwitterionic biodegradable surfactant represented by Formula (XII):

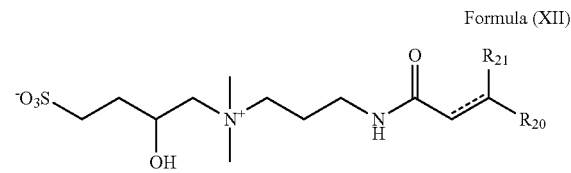

Formula (XII)

wherein

- - - - - represents a single or double bond when R21 is H, and a single bond when R21 is other than H;

R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and R20 is a C11-C21 linear or branched alkyl, alkenyl, or alkynyl group.

In some embodiments, the biodegradable surfactants herein described comprise the biodegradable surfactant represented by Formula (XIII) and optionally at least one counter ion Z:

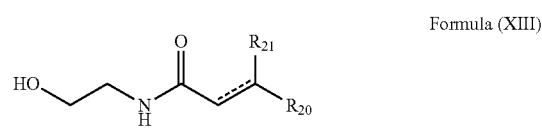

Formula (XIII)

wherein

- - - - - represents a single or double bond when R21 is H, and a single bond when R21 is other than H;

R21 is selected from sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy;

R20 is a C11-C21 linear or branched alkyl, alkenyl, or alkynyl group and wherein Z is selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

In some embodiments, the biodegradable surfactants herein described comprise the biodegradable surfactant represented by Formula (XIV) in which the polyol unit of the head portion is extended by an oligo ethylene oxide of 1-5 repeat units.

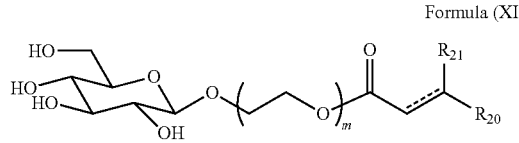

Formula (XIV)

wherein m=1-6;

------: represents a single or double bond when R21 is H, and a single bond when R21 is other than H;

R21 is selected from sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and R20 is a C11-C21 linear or branched alkyl, alkenyl, or alkynyl group.

In some embodiments, the biodegradable surfactants herein described comprise the amphiphilic substituted hydrocarbon of Formula (XV) and optionally at least one counter ion Z:

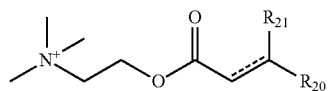

Formula (XV)

wherein

------: represents a single or double bond when R21 is H, and a single bond when R21 is other than H;

R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy;

R20 is a C11-C21 linear or branched alkyl, alkenyl, or alkynyl group; and wherein Z is selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

In some embodiments, the biodegradable surfactants herein described comprise one or more amphiphilic substituted hydrocarbons of Formula (XVI), Formula (XVII) or Formula (XVIII):

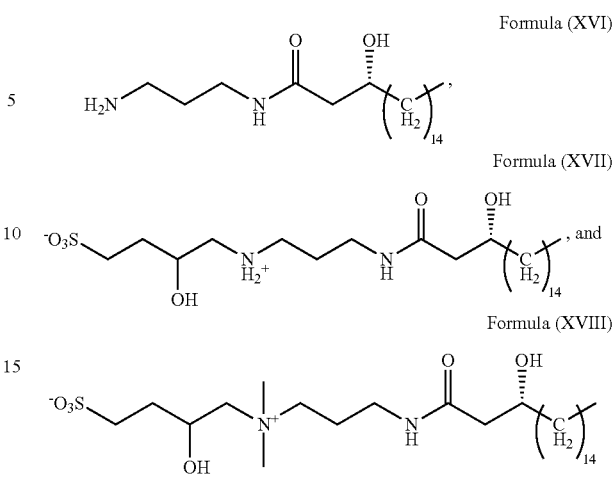

The biodegradable surfactant of Formula (XVI) is illustrative of a cationic biodegradable surfactant which is at least 50% positively charged when the amine becomes protonated in neutral or acidic aqueous medium. The biodegradable surfactants of Formula (XVII) and Formula (XVIII) are illustrative of a zwitterionic biodegradable surfactants which comprise at least one zwitterion in the head portion of the zwitterionic biodegradable surfactants.

In some embodiments, the biodegradable surfactants herein described comprise mannitol and arabitol esters of 3-hydroxy fatty acid, 3-methoxy fatty acid, and fatty acids with a single double bond; chain lengths are mainly C16 and C18 or their derivatives. As used herein, a derivative is a chemically modified compound which retains at least 50% by atom of the structure of the original compound.

In some embodiments herein described, the biodegradable surfactants are also tunable, i.e. can be tuned to achieve a desired adjusted hydrophilic-lipophilic balance (i.e. aHLB). As used herein, the term "tunable" refers to the amenability of a compound to undergo chemical modification by five or less chemical steps of reactions to achieve a specified increase or decrease of aHBL value of the modified biobased surfactant.

A given surfactant typically has an associated aHLB value and cannot change in its properties due to the structure. Conventional solutions to produce surfactants with various aHLB values have been to synthesize and discover a large number of surfactants that will fit in each category, resulting in a wide variety of structures with limited options to "tune" them for a desired application. The heterogeneity of the produced surfactants makes it difficult to fine-tune them, or use the same surfactant for a variety of applications within the aHLB scale.

Due to increasing concerns about environmental issues and generation of harmful by-products of chemicals (Frost and Sullivan Market Report, 2014, "Advances in Surfactants"), biodegradable surfactants have gained popularity due to their "green factor", i.e. their ability to be biodegradable—metabolized naturally by organisms in the environment—and biocompatible—less toxic to the ecosystem, especially in marine environments [7]. Previous work has been conducted on four biosurfactant species: surfactin, rhamnolipids, sophorolipids, and mannosylerythritol lipids (produced by *Bacillus, Pseudomonas, Candida,* and *Pseudozyma* species, respectively) [8]. Although these biosurfactants have shown utility in specific applications, there is a need to identify new classes compounds that fill gaps within the biosurfactant aHLB scale, thereby opening new avenues of biosurfactant application within industry [8, 9].

Thus, in some embodiments herein described, the biodegradable surfactants can be tuned for a wide range of industrial applications that demand specific hydrophobicity or hydrophilicity properties that span the aHLB score range. In particular, the tunable biodegradable surfactants can be used in place of non-biodegradable surfactants such as many of those produced from petrochemicals that can create potential threats to the environment. The tunable biodegradable surfactants also contrast with the small number of currently available biosurfactants that have a "fixed" limited aHLB range of 9-12.

In particular, biodegradable surfactants herein described can be tuned by modifying tuning moieties of a biodegradable surfactant herein described to provide tuned moiety in the biodegradable surfactant. A "tuning moiety" or "tunable moiety" of a tunable biodegradable surfactant as used herein refers to a group of covalently bonded atoms on the tunable biodegradable surfactant that can be modified to provide another group of atoms or functional group or tuned moiety. Therefore, the term "tuned moiety" refers to a replacement group of atoms or functional group chemically derived from a "tunable moiety". In several embodiments the tuning moieties and tuned moieties of the biodegradable surfactant herein described can be the hydrophilic or a hydrophobic group comprising at least one heteroatom of a biodegradable surfactant herein described. The tuning moiety of the tunable biodegradable surfactant and the tuned moiety of the tuned biodegradable surfactant may have different aHLB values. Therefore, the replacement of a tuning moiety with a tuned moiety can result in a decrease or increase of the aHLB value of the biodegradable surfactant depending on at least in part the Group Number difference between the tuning moiety and the tuned moiety (see Table 1 for Group Numbers of various functional groups). For example, T of Formula (XX) is a tuning moiety. Q of Formula (XX) can be a tuning moiety when it is an OH or a $NH_2$.

The tuning moiety can be charged with at least one counterion Z as described herein, polar and neutral, which includes, for example, hydroxyl, acetyloxy, C1-C2 alkoxy groups. In general, a charged tuning moiety confers a greater hydrophilicity than a polar tuning moiety. For an anionic tuning moiety, the stronger the corresponding acid of the anionic tuning moiety, the more hydrophilic it will be. For example, an organic sulfate group with a sodium counterion will be more hydrophilic than a carboxylate group with a sodium counterion, which in turn is more hydrophilic than a carboxylic acid group. Cationic tuning moiety includes protonated amine, protonated C1-C2 alkyl amine, protonated C1-C2 dialkyl amineC1-C2 trialkyl ammonium, pyridinium, with at least one counterion Z. In general, the more hydrocarbons on the cationic tuning moiety, the less hydrophilic as it would be as will be understood by a skilled person.

In biodegradable surfactant herein described, tuning moiety can be linked by one or more node moieties. As used herein, the term "node moiety" refers to a chemical structure unit in a head portion of a biodegradable surfactant that directly links by a covalent bond to each of the at least one tuning moiety and is further connected to a H or an alkyl group and a methylene group.

In some embodiments, the node moiety can be C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups.

The term "heterocyclic" refers to an aromatic or aliphatic cyclic group in which at least one carbon atom of the cyclic group is replaced with a heteroatom. As used herein, a heteroalkyl is a C2-C30 alkyl group wherein at least one of the carbon atom is replaced by a heteroatom.

As used herein, a heteroaryl is an aryl group wherein at least one of the carbon atom is replaced by a heteroatom the terms "heteroaryl" and "heteroaromatic" respectively refer to "aryl" and "aromatic" groups in which at least one carbon atom of the "aryl" and "aromatic" groups is replaced with a heteroatom. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, and tetrazolyl groups.

As used herein, a heterocycloalkyl is cycloalkyl group wherein at least one of the carbon atom is replaced by a heteroatom.

M some embodiments, a biodegradable surfactant herein described can be a tunable biodegradable surfactant. In some of those embodiments, the tunable biodegradable surfactant represented by Formula (XX) and optionally at least one counter ion Z:

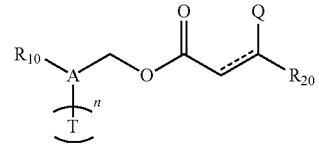

Formula (XX)

wherein

- - - - - represents a single or double bond when Q is H, and a single bond when Q is other than H;

n is 1-6;

A is a node moiety selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups, T is a tuning moiety each independently selected from OH, or $NH_2$;

Q is selected from H, OH, or $NH_2$;

R10 is H, or C1-C2 alkyl group;

R20 is a C11-C21 linear or branched alkyl, alkenyl, or alkynyl group; and

Z is selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

As shown in Formula (XX), the node moiety A is linked to n number of T tuning moieties by a covalent bond. It is to be appreciated that each of the n number of T tuning moieties are independently selected from OH or $NH_2$.

In some embodiments, a head portion of tunable biodegradable surfactants represented by Formulas (X), Formula (XX), and Formulas (XXI), is derived from a polyol having a hydroxymethyl group. The derivation can be esterification of the hydroxymethyl group of the polyol or amination of the hydroxylmethyl group of the polyol followed by an amidation.

As used herein, a "polyol" indicates an organic moiety that contains at least two hydroxyl groups. Exemplary polyols include Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Galactitol (6-carbon), Fucitol (6-carbon), Iditol (6-carbon), Inositol (6-carbon; a cyclic sugar alcohol), Volemitol (7-carbon).

In some embodiments, a polyol is represented by a general formula $HOCH_2(CHOH)_pCH_2OH$ wherein p is 0-5.

In some embodiments, a tail portion of tunable biodegradable surfactants represented by Formulas (X), Formula (XX), Formulas (XXI), Formulas (XXII), and Formula (XXIII) is derived from a fatty acid. The derivation can be an esterification or amidation of the carboxyl group of the fatty acid with a corresponding hydroxyl or amino group respectively bearing a head portion of the tunable biodegradable surfactants.

As used herein, a fatty acid is a C14-C24 aliphatic linear or branched alkyl, alkenyl, or alkynyl carboxylic acid, optionally substituted with one hydroxyl group. Exemplary alkyl fatty acid includes Myristic acid ($CH_3(CH_2)_{12}COOH$), Palmitic acid ($CH_3(CH_2)_{14}COOH$), Stearic acid ($CH_3(CH_2)_{16}COOH$) Arachidic acid ($CH_3(CH_2)_{18}COOH$), Behenic acid ($CH_3(CH_2)_{20}COOH$), Lignoceric acid ($CH_3(CH_2)_{22}COOH$), and 3-hydroxy octadecanoic acid. Exemplary alkenyl fatty acid includes Myristoleic acid ($CH3(CH2)3CH=CH(CH2)7COOH$), Palmitoleic acid ($CH_3(CH_2)_5CH=CH(CH_2)_7COOH$), Sapienic acid ($CH_3(CH_2)_8CH=CH(CH_2)_4COOH$), Oleic acid ($CH_3(CH_2)_7CH=CH(CH_2)_7COOH$), Elaidic acid ($CH_3(CH_2)_7CH=CH(CH_2)_7COOH$), Vaccenic acid ($CH_3(CH_2)_5CH=CH(CH_2)_9COOH$), Linoleic acid ($CH_3(CH_2)_4CH=CHCH_2CH=CH(CH_2)_7COOH$), Linoelaidic acid ($CH_3(CH_2)_4CH=CHCH_2CH=CH(CH_2)_7COOH$), α-Linolenic acid ($CH_3CH_2CH=CHCH_2CH=CHCH_2CH=CH(CH_2)_7COOH$), Arachidonic acid ($CH_3(CH_2)_4CH=CHCH_2CH=CHCH_2CH=CHCH_2CH=CH(CH_2)_3COOH$), Eicosapentaenoic acid ($CH_3CH_2CH=CHCH_2CH=CHCH_2CH=CHCH_2CH=CHCH_2CH=CH(CH_2)_3COOH$), Erucic acid ($CH_3(CH_2)_7CH=CH(CH_2)_{11}COOH$), and Docosahexaenoic acid ($CH_3CH_2CH=CHCH_2CH=CHCH_2CH=CHCH_2CH=CHCH_2CH=CHCH_2CH=CH(CH_2)_2COOH$).

In some embodiments, the tunable biodegradable surfactant herein described is represented Formula (XXI) and optionally at least one counter ion Z:

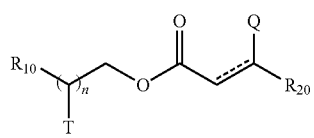

Formula (XXI)

wherein
----- represents a single or double bond when R21 is H, and a single bond when R21 is other than H;

n is 1-6,
T is a tuning moiety each independently selected from OH, or $NH_2$,
Q is a selected from H, OH, or $NH_2$;
R10 is H, or C1-C2 alkyl group; and
R20 is a C11-C21 linear or branched alkyl, alkenyl, or alkynyl group.

A tunable biodegradable surfactant compound herein described can be provided with methods herein described as will be understood by a skilled person.

In some embodiments, the method of providing a tunable biodegradable surfactant compound can comprise isolating the tunable surfactant compound from a cell expressing an amphiphilic heteroatom containing hydrocarbon herein described.

The term cell indicates the basic structural, functional, and biological unit of all known living organisms. Cells consist of cytoplasm enclosed within a membrane, which contains many biomolecules such as proteins and nucleic acids. Cell can be prokaryotic and eukaryotic cells wherein the term "prokaryotic" refers to a cell which contains and includes a single chromosome that is in direct contact with the cytoplasm with no nucleus or other organelles in the cell. In particular in prokaryotic cells the nuclear region in the cytoplasm is called the nucleoid. Most prokaryotes are the smallest of all organisms ranging from 0.5 to 2.0 µm in diameter. Prokaryotic cells comprise Bacteria and Archaea. The term "eukaryotic" refers to a cell that contains a nucleus and other cell organelles in the cell. The main distinguishing feature of eukaryotes as compared to prokaryotes is compartmentalization: the presence of membrane-bound organelles (compartments) in which specific metabolic activities take place. Eukaryotic cells comprise cells from plants, animals, fungi, slime moulds, protozoa, and algae.

Cells in the sense of the disclosure that can natively produce the amphiphilic heteroatom containing hydrocarbon can be identified by measuring the surface tension of the medium in which the cells are grown. Biosurfactants are "surface active", and therefore lower the surface tension at the air-water or water-oil interface. This simple measurement can be performed using a tensiometer. Cells that lower the surface tension of the surrounding liquid can be selected as surfactant producers. More detailed analyses of the surfactant structure and mass would subsequently be performed using High Resolution Liquid Chromatography-Electrospray Ionization-Mass Spectrometry (LC-ESI-MS) and additional techniques identifiable by a skilled person upon reading of the present disclosure.

Additional cells can be genetically engineered to provide a recombinant pathway for the biosynthesis of an amphiphilic heteroatom containing hydrocarbon in the sense of the disclosure with methods and procedures identifiable by a skilled person.

A pathway in the sense of the disclosure is a series of interactions among molecules in a cell that leads to production of a certain product or a change in the cell. Some of the most common biological pathways are involved in metabolism, the regulation of gene expression and the transmission of signals. A pathway typically comprises two or more enzymatically controlled chemical reactions by which a substrate is converted into a product. A biosynthetic pathway in the sense of the disclosure is a series of two or more enzymatically controlled chemical reactions resulting in the production of a product and in particular of an amphiphilic heteroatom containing hydrocarbon in the sense of the disclosure.

Exemplary hydrocarbons and pathways for the related production in cells are described in Example 19. Additional hydrocarbons and pathways are identifiable upon reading of the present disclosure.

In some embodiment, a biodegradable surfactant can be provided biosynthetically by genetically engineering a cell expressing the biodegradable surfactant in a cell to activate one or more enzymes forming a biosynthetic pathway for the production of an amphiphilic heteroatom containing hydrocarbon in the sense of the disclosure.

The terms "activate" or "activation" in a cell as used herein with reference to a biologically active molecule, such as an enzyme, indicates any modification in the genome and/or proteome of a cell that increases the biological activity of the biologically active molecule in the cell. Exemplary activations include but are not limited to modifications that results in the conversion of the enzyme from a biologically inactive form to a biologically active form and from a biologically active form to a biologically more active form, and modifications that result in the expression of the enzyme in a cell wherein the enzyme was previously not expressed. For example, activation of a target enzyme can be performed by expressing a native or heterologous polynucleotide encoding for the target enzyme in the cell, by expressing a native or heterologous polynucleotide encoding for the target enzyme or for a different enzyme involved in the pathway for the synthesis of the target enzyme in the cell, by expressing a native or heterologous molecule that enhances the expression of the enzyme in the cell.

Activation of one or more enzymes in a pathway can be performed by direct or indirect reaction of the molecular components involved in the pathway. Examples of a direct activation of a molecular component comprise in a pathway the production of an alternate sigma factor that drives the expression of a gene controlled by the alternate sigma factor promoter, or the production of a small ribonucleic acid that increases expression of a riboregulatory-controlled RNS. Specific examples of this include the activity of sigma28 and sigma54. Examples of indirect activation of a molecular component comprise the production of an activating protein which when in tandem with a small molecule (e.g. 3OC12HSL) or possibly an additional molecular component of the pathway, causes the increase of expression of a gene, or the production of a protein that regulates an intermediate protein that increases the expression of a target gene, where two cascades of repression in effect cause activation.

Methods for genetic modifications of a cell to activate one or more enzyme in a cell can include modification of the cell by transfer of the genes using a recombinant plasmid, a recombinant non-viral vector, or a recombinant viral vector, encoding such gene expression construct and additional methods identifiable by a skilled person.

The genetic modifications described above can be achieved using various techniques identifiable by a skilled person including using gene expression constructs that direct expression or overexpression of enzymes involved in the lipid biosynthesis pathway, including suitable promoter, enhancer, and other elements required for overexpression in bacteria that would be recognized to perform this function by those of ordinary skill in the art. For example, promoters can be constitutively active or inducible. RNA can be isolated from a cell, and cDNA produced by reverse transcription using standard techniques and commercial kits. Alternatively, genomic DNA can be purified from the cell, and cDNA or genomic DNA encoding one or more key enzymes in the lipid biosynthesis pathway of Rhodotorula isolated, following methods known to those skilled in the art. PCR-based amplification of the gene of interest can be performed using appropriately designed primer pairs (e.g. using PrimerDesign or other programs known to those skilled in the art). An encoded tag can be incorporated into the primer design (e.g. encoding a His-tag designed to be fused to the N- or C-terminus of the recombinant enzyme) to facilitate protein purification (e.g. using commercially-available His-tagged protein purification columns/kits), as described below. PCR-based amplification can be followed by ligation (e.g. using T4 DNA ligase) of the amplicon into an appropriate expression cassette in a plasmid suitable for propagation in bacteria or other cells, such as transformation-competent *E. coli*, followed by growth of transformed cell cultures, purification of the plasmid for confirmation of the cloned pyocyanin demethylase by DNA sequence analysis, among other methods known to those skilled in the art.

Cloned recombinant genes can be expressed using cell-based methods, or cell-free methods, following standard techniques and using commercially available kits. Cell-based methods for expression of recombinant enzymes can include expression in prokaryotic or eukaryotic cell cultures, such as *E. coli* or other bacterial cells, yeast strains, insect cells, or mammalian cells, among others known to those skilled in the art.

Exemplary cells capable of providing a biodegradable surfactant in the sense of the disclosure comprise yeasts such as native a *Rhodotorula* yeast strain, *Saccharomyces cerevisiae, Escherichia coli*, insect cells, or mammalian cell lines which can be native or genetically modified to provide recombinant expression of the biosurfactant biosynthetic pathway in accordance with the indications of the instant disclosure. In particular exemplary cells in which the surfactant biosynthetic pathway can be expressed recombinantly include *Saccharomyces cerevisiae* (yeast), *Escherichia coli* (bacteria), baculovirus-insect cell systems, or mammalian cell lines (e.g. CHO, HEK 293, PER.C6, and CAP/CAP-T).

In some embodiments, a method herein described to provide a biodegradable surfactant of the disclosure comprises causing expression in a medium of an amphiphilic heteroatom containing hydrocarbon comprising an hydrophilic head portion and an hydrophobic tail portion, the expression performed by a cell configured to include a pathway resulting in the production of said amphiphilic heteroatom containing hydrocarbon in the cell, thus providing an expressed tunable biodegradable surfactant. The method can further comprise isolating the expressed tunable biodegradable surfactant from the medium thus providing the tunable biodegradable surfactant.

Metabolic engineering and synthetic biology strategies can be employed for the production of hydrocarbon in a cell. In particular, metabolic engineering methods can be used to activate hydrocarbon biosynthetic pathways which generally involve enzyme-catalyzed reactions by activating or deactivating compounds involved in such pathways. As a person skilled in the art will understand upon reading of the present disclosure, genetic circuits may also be designed to form a metabolic pathway for the production of desired hydrocarbon in a cell. The designed metabolic pathway may comprise a sequence of chemical and/or enzymatic reactions catalyzed by enzymes in which a product of one enzyme acts as the substrate for the next and consequently leading to the production of a hydrocarbon of interest pathways can be molecular components such as substrates or metabolites of the biosynthetic pathways, minerals, or other cofactors required by the enzymes of a biosynthetic pathway to function properly. In some embodiments, small molecules that are not present in the cellular environment but important for the biosynthetic pathway of hydrocarbons such as inducers or substrates or components that form the input or intermediate of the pathway can be introduced by genetic engineering. Metabolic intermediates can also be introduced to the systems as will be understood by a person skilled in the art.

Hydrocarbons produced by cells can be extracted using methods identifiable to a person skilled in the art. For example, to extract hydrocarbons, organic solvent such as dichloromethane can be added to pelleted dried cells producing hydrocarbons, and then placed in a sonicator bath for a certain time period then centrifuged to pellet any remaining material. The supernatant containing hydrocarbons can be then transferred for storage.

In some embodiment, a biodegradable surfactant can be provided biosynthetically by genetically engineering the cell expressing the biodegradable surfactant to inactivate an enzyme involved in a chemical transformation of the amphiphilic heteroatom containing hydrocarbon in the cell.

The terms "inactivate" or "inactivation" as used herein with reference to a biologically active molecule, such as an enzyme or an electron carrier molecule, indicates any modification in the genome and/or proteome of a microorganism that prevents or reduces the biological activity of the biologically active molecule in the cell. Exemplary inactivations include but are not limited to modifications that results in the conversion of the enzyme from a biologically active form to a biologically inactive form and from a biologically active form to a biologically less or reduced active form, and any modifications that result in a total or partial deletion of the biologically active molecule. For example, inactivation of an enzyme can be performed by deleting or mutating the a native or heterologous polynucleotide encoding for the enzyme in the microorganism, by deleting or mutating a native or heterologous polynucleotide encoding for the enzyme or for a different enzyme involved in the pathway for the synthesis of the target enzyme in the cell, by activating a further a native or heterologous molecule that inhibits the expression of the enzyme in the cell.

Inactivation mutants can be produced using approaches such as frameshift mutations, open-reading frame deletions, insertion of stop codons, and others known to those skilled in the art. In general, these methods can use homology directed repair or homologous recombination to replace a functional version of the gene in the yeast with a deletion cassette. The term "deletion cassette" means a polynucleotide comprising a non-functional version of the gene, or a DNA sequence encoding another gene or polynucleotide sequence, with or without an encoded selectable marker such as an antibiotic resistance gene or auxotrophic selection marker, to replace all or part of the open reading frame of an endogenous gene. Homologous recombination recognition sequences in the deletion cassette can be designed based on homology to sequences flanking all or part of the sequence encoding the gene of interest to be knocked out, to enable targeted deletion or otherwise inactivation of all or part of the endogenous gene. Plasmids encoding deletion cassettes can be cloned using methods known to those skilled in the art, typically using PCR-based amplification of all or part of the endogenous gene, with a mutation, such as a frameshift, or a deletion introduced into the gene using techniques known in the art, including but not limited to using methods such as endonuclease deletion of one or more nucleotides in the encoded gene to result in a non-functional gene, or insertion of one or more polynucleotide sequences within the gene, such as a stop codon or one or more sequences encoding selectable markers, for example. Deletion cassette-containing plasmids can be cloned and propagated in cultures of transformation competent cells, such as bacteria, for example E. coli DH5alpha, and positive transformant clones containing the deletion cassette can be detected in presence of appropriate selection antibiotics, with resistance to the antibiotic conferred by a gene encoded in the plasmid. Positive clones can be picked by growing on selection media plates in presence of appropriate antibiotic and thereafter propagated in liquid culture media, following isolation of the plasmid from the bacterial culture and confirmation of the cloned plasmid, using analytical restriction endonuclease digests, gel electrophoresis, and DNA sequencing, among other methods known to those skilled in the art.

A linearized deletion cassette can be produced for example by PCR amplification from a plasmid using appropriately designed primers, to produce a linearized DNA fragment capable of mediating homologous recombination. Alternatively, a linearized homologous recombination fragment can be produced by linearization using restriction endonucleases, among other methods known to skilled persons. In particular, single-cutting restriction endonucleases can be used for cassette linearization, where a "single-cutting restriction endonuclease" is an enzyme that cuts a polynucleotide at one site based on a single recognition sequence site within the polynucleotide. Linearized deletion cassettes can be introduced into yeast using transformation protocols known to those skilled in the art, such as heat shock, or electroporation, among others. A deletion cassette comprising a gene encoding a selectable marker, for example an antibiotic resistance gene selection marker, can be used to confirm insertion of the deletion cassette into the genome, by selecting transformants grown in media in presence of an appropriate antibiotic for which the gene confers resistance. Alternatively, auxotrophic selection markers can be used where the yeast has an inability to synthesize a particular organic compound required for its growth, and the selection marker supplies the compound. Exemplary auxotrophic selection markers comprise those encoding amino acids. Transformant yeast colonies can be isolated from selection media plates, cultures grown and analyzed for presence of the deletion cassette by PCR and gel electrophoresis, among other techniques known to those skilled in the art. DNA sequencing can be performed to confirm homologous recombination of the deletion cassette into the site of the targeted endogenous gene using appropriately designed sequencing primers, such as those designed to bind to sequences internal to and/or flanking the inserted deletion cassette and amplify a portion of the polynucleotide inserted into the genome.

In particular, in some embodiments the cell can be engineered with one or more deletions of one or enzymes responsible for acetylation of one or more base compounds, in order to produce only the unacetylated base compound according to methods identifiable by a skilled person upon reading of the present disclosure.

In particular, in some embodiments, the cell can be genetically engineered to inactivate, (and in particular to delete, modify, alter, silence, or inhibit) one or more enzymes responsible for transforming the amphiphilic heteroatom containing hydrocarbon by acetylation, deacetylation, hydroxylation, dihydroxylation, phosphorylation, or sulfation, of the tunable surfactant compound, among other modifications known to those skilled in the art.

An exemplary enzyme is provided by a sugar acetyltransferases and an exemplary inactivation/deletion of the acetyltransferase genes in the yeast are described in details in Example 21. A skilled person will be able to identify additional enzymes responsible for transforming the amphiphilic heteroatom containing hydrocarbon by acetylation, deacetylation, hydroxylation, dihydroxylation, phosphorylation, or sulfation as well as procedures for the related inactivation upon reading of the present disclosure.

The enzymes responsible for acetylation of the amphiphilic heteroatom containing hydrocarbon as described herein can be identified by analyzing homology of gene or protein sequences of yeast strains capable of producing biodegradable surfactants to gene or protein sequences encoding known acetyltransferase enzymes. For example, the genome of *R. taiwanensis* has been sequenced and therefore candidate acetyltransferases can be identified through homology with DNA, mRNA, or protein sequences with those of other known transacetylases or acetyltransferases in databases such as NCBI and others known to persons skilled in the art.

The terms "acetyltransferase" and "transacetylase" indicate a type of transferase enzyme that catalyzes the transfer of an acetyl group from one compound to another, such as peptides, proteins, and carbohydrates. Examples include histone acetyltransferases including CBP histone acetyltransferase, choline acetyltransferase, chloramphenicol acetyltransferase, serotonin N-acetyltransferase, NatA Acetyltransferase, NatB acetyltransferase, and others identifiable by those skilled in the art.

Homology can be determined using available sequence analysis algorithm programs including but not limited to CLUSTAL, ALIGN, GAP, BESTFIT, BLAST, FASTA, and TFASTA among others known to a skilled person. Sequences of DNA, mRNA, or protein having at least 80% sequence identity to known acetyltransferase sequences, in particular known yeast acetyltransferase sequences, can be considered homologous.

Homology can also be determined on the basis of protein structural similarity. Several publicly available online servers can be used to detect protein structure alignment and calculate percent structural similarity, such as FATCAT [16], SuperPose [17], iPBA [18], MAPSCI [19], and others known to a person skilled in the art. Proteins having at least 80% structural identity to known acetyltransferase protein structures, in particular known yeast acetyltransferase protein structures, can be considered homologous.

Homology of yeast genes can be analyzed with respect to known acetyltransferase enzymes, such as those expressed in budding yeast such as histone acetyltransferases (HATs)/lysine acetyltransferases (KATs) which use acetyl-CoA as a substrate to transfer acetyl groups to histones and non-histone proteins [10, 11], or carbohydrate transacetylase similar to the acetyltransferase in *Candida bombicola*, which mediates the acetylation of de novo synthesized sophorolipid biosurfactants [12], among others identifiable by a skilled person.

Following identification of an acetyltransferase gene by sequence analysis as described above, a yeast knockout strain (deletion mutant or inactivation mutant) can be produced. The terms "knockout strain", "inactivation mutant" or "deletion mutant" refer to organisms wherein a normal functional gene has been deleted or replaced by a defective gene or other polynucleotide sequence that is unable to produce the functional gene.

An acetyltransferase in *Candida bombicola* was identified as being responsible for acetylation of sophorolipid biosurfactants (see website https://www.ncbi.nlm.nih.gov/pubmed/21702032 at the time of filing of the present disclosure). The authors deleted the gene, thereby "knocking out" the acetyltransferase, and only producing unacetylated sophorolipids in this strain. The protein sequence of the Candida bombicola acetyltransferase (SEQ ID NO: 1) is:

MVVNSSKDPQNKGMTPRKEIDQEMVSWAKKNLKNTPGNENYEKMVSGVPY

NPYDPDLMFRALATSEKVREFNTIASESRTFESNHAAYIKKVEILKDTFG

QTKDIVWLTAPFSVDFGFNISVGEHFYANFNVCFLDSAPIIFGDEVIVGP

NTTFVTATHPISPEKRARRIVYALPIKVGNNVWIGANVTVLPGVTIGDGS

TIAAGAVVREDVPPRTVVGGVPARILKHIPEEDPDEAEGEELEFLLPVEM

NVNTANQKV.

A BLAST search of this protein sequence was conducted against all of the identified Rhodotorula taiwanensis MD1149 proteins in order to find homology with similar acetyltransferase enzymes in Rhodotorula. Two hits were identified SEQ ID NO: 2 and SEQ ID NO: 3): >BMF94_2857 hypothetical protein
(SEQ ID NO: 2)
MPEFVRASADELEAFKALSEREKMVKGLAYLAMDDQELARDRLKARTLCQ

HHPFIEWRDDLPISEFYGPDSRLQNLAELFQVSLERVRSIGIEPPLYVDY

GYNIEFRGDFYANFGAVFLDCAKISFGARTLLGPGVHVYCATHAVEVDER

VAGYERAYPVELGDDLWVGGGAKIIGPCKIGNNCTIAANAVVKGDFPDNV

VIGGIPARILKHLDPPQGPIDPEDRRLVVPLPSAKSAAKNDITM (SEQ ID NO: 2) and >BMF94_0387 hypothetical protein
(SEQ ID NO: 3)
MAEQTETPTWNGIDLVENRRRMERGELYTAFVPELTKERRVASQACAKYN

RVATEVTRREQVELFKKIVTTLPDLPPAKEDPDEDEAQLTAFPWAEPPFK

VDYCGRIFIGENSFMNFNFIVLNTCEVRIGSRCLFGPNVSLFAGTHPLDP

AIRNGTAGPENGGPITIGDDCWFGGNVTVLPHVTIGRGVTVGAGSVVTKS

VPAFAVVVGNPARIVRKIESEWANEHFAAHPEEQWEVPTTKT.

A Pfam Database Search of these two Rhodotorula proteins (which groups them into a type of protein family) identified both of them as "maltose acetyltransferases".

An NCBI Delta BLAST (Domain Enhanced LookupTime Accelerated BLAST) annotated the conserved domains of these hypothetical proteins as "sugar O-acetyltransferase similar to maltose O-acetyltransferase and galactoside O-acetyltransferase, which catalyze the CoA-dependent acetylation of the 6-hydroxyl group of their respective sugar substrates."

In some embodiments, the conserved functional domains of these Rhodotorula "hypothetical proteins" as sugar acetyltransferases can be primary knockout targets for generating a Rhodotorula strain that produces unacetylated biosurfactants.

Inactivation of candidate acetyltransferase genes and production of unacetylated surfactants from yeast strains can be performed following methods known in the art, for example those described in Saerens et al. (2011) [12], as detailed in Example 12. Other methods for targeted deletion of genes encoding acetyltransferase enzymes can be used, such as those using PCR-based gene deletion strategies as described in ref: Baudin et al., Nucl. Acids Res. 21, 3329-3330, 1993 and ref: Wach et al., Yeast 10, 1793-1808, 1994. A resulting engineered acetyltransferase deletion mutant yeast strain can be grown in appropriate media, as described in the Examples, and the resulting surfactants produced by a deletion mutant yeast strain can be purified from the cells or from the growth media using methods known in the art, such as solid phase extraction as detailed in the Examples. The purified surfactants can then be analyzed to confirm the production of unacetylated forms using methods such as LC-MS, among others known to those skilled in the art.

The production of a biosurfactant as disclosed herein can include any suitable metabolic engineering strategies for activating a pathway resulting in the biosurfactant of the disclosure and therefore increasing the yield of the biosurfactant product. Exemplary engineering strategies are as described in references [13] [14] [15].

Figure 2:
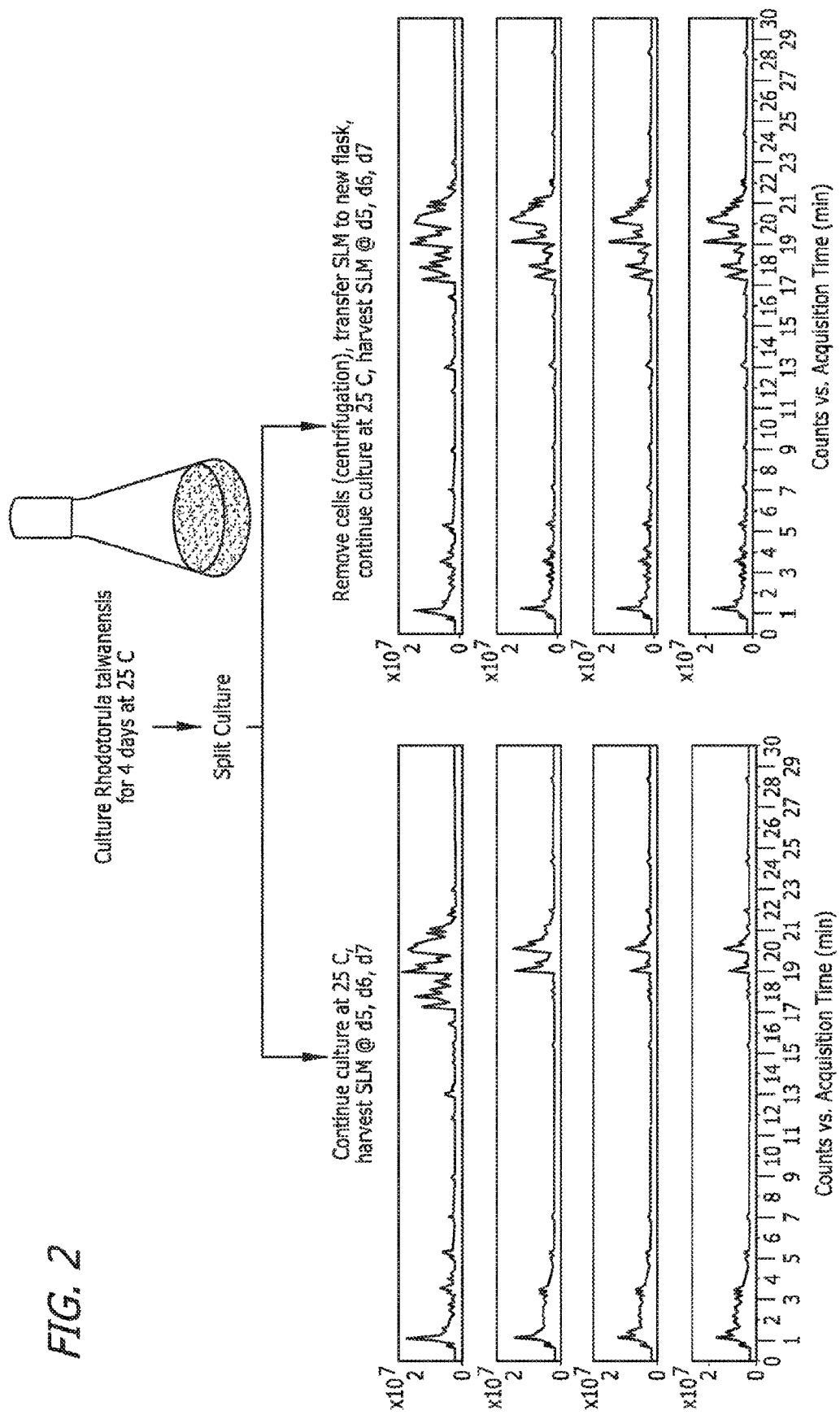
FIG. 2 shows that biosurfactants produced by *R. taiwanensis* are biodegradable. *R. taiwanensis* was cultured for four days (d4) at 25° C. (peak biosurfactant production). The culture was then split; half of the culture was allowed to continue shaking with cells (left chromatograms), while in the other half, cells were removed via centrifugation, and allowed to continue shaking (right chromatograms). The two flasks were monitored for an additional three days (d5, d6, d7) by harvesting spent liquid medium (SLM) and analyzing the SLM by LC-MS. In the presence of cells, the biosurfactants were degraded to 14% of their peak concentration; in the absence of cells, the biosurfactant concentration remained relatively unchanged.

In particular in some embodiments, the overall yield of the unacetylated surfactants—produced by the recombinant Rhodotorula strain—can be enhanced using methods known in the art, for example those described by Bogaert et al, 2009. [15] Fatty acid compounds, such as the biosurfactants produced by Rhodotorula, can be metabolized by yeast strains as a carbon source for cell growth and energy supply when glucose levels are low. This was observed for Rhodotorula biosurfactants as shown in FIG. 2. In order to maximize biosurfactant yield from the yeast, one could delete or suppress the multifunctional enzyme type 2 (MFE-2) gene from the Rhodotorula genome through genetic knockout techniques known to those skilled in the art; this gene encodes a peroxisome enzyme that is responsible for the second (hydratation) and third step (second dehydrogenation) in the beta-oxidation pathway that occurs in the peroxisome. A yeast strain deleted for MFE-2 would be unable to grow on fatty acids, only glucose (thereby protecting the biosurfactant yield in the growth medium).

The genetically knocked-out bacteria can be created by deleting or otherwise inactivating the selected genes according to techniques identifiable by a skilled person including by microdeletion, clean deletion via double recombination, recombineering insertional inactivation, CRISPRi, CRISPR-mediate recombination, transposon insertion, mutational inactivation, methylation and/or epigenetic inactivation as well as other techniques identifiable by a skilled person. Methods for creating the knock-out fragments are described in Bogaert 2009, which is incorporated herein by reference in its entity. In general, knocking out genes in conventional yeast such as S. cerevisiae can be done by constructing a linear fragment containing a marker flanked on each site by only 40 bp of the target gene and transform the yeast cells with this construct (Brachmann et al., 1998). For nonconventional yeasts, longer fragments of several hundreds or even more than 1000 bp will be used (Weslowski-Louvel et al., 1988). Disruption cassettes with differently sized flanking regions can be created for testing transformant efficiency. An exemplary knock out fragment is provided by the MFE-2 coding fragment (see Example 22).

In some embodiments, genes such as PEX10 which are required for peroxisome formation can be deleted to maximize biosurfactant yield.

In some exemplary embodiments, methods building PEX10 deletion plasmid are described in Zhang 2016, which is incorporated herein by reference in its entity. For example, the PEX10 deletion plasmid pGI2-ΔPEX10 can be built as follows. The nourseothricin resistance cassette is first PCR amplified from pGI2. Next, the upstream and downstream regions flanking the PEX10 gene (GenBank accession no KU886331), 1 kb in length, are PCR amplified from R. toruloides IFO0880 genomic DNA. These three DNA fragments are then ligated to pGI2 linearized with the restriction enzymes AscI and EcoRI by Gibson assembly, resulting in the plasmid pGI2-ΔPEX10 shown in FIG. 1c of Zhang 2016.

In some embodiments, overexpression of key enzymes in the lipid biosynthesis pathway of Rhodotorula can also dramatically impact biosurfactant yield. The enzymes involved in lipid biosynthesis include malic enzyme (ME), pyruvate carboxylase (PYC1), glycerol-3-P dehydrogenase (GPD), and stearoyl-CoA desaturatse (SCD) as described in Zhang et al, 2016. [13] [14].

Figure 1B:
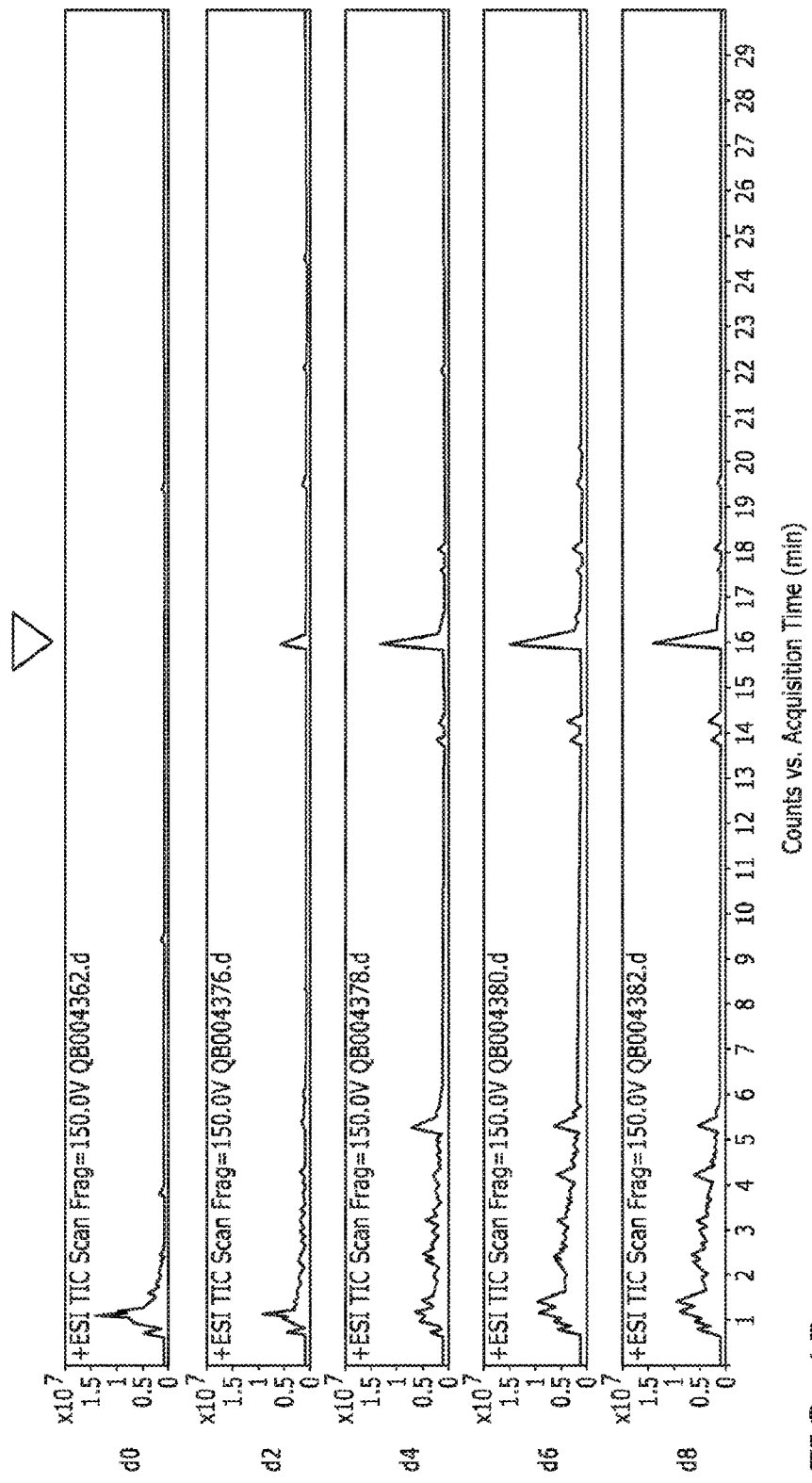
FIG. 1B shows the presence of these sophorolipid biosurfactants produced by *R. bogoriensis* on day 0 (d0), day 2 (d2), day 4 (d4), day 6 (d6), and day 8 (d8) was readily detected in the LC-MS total ion chromatograms (indicated by the triangle).

In some exemplary embodiments, methods for overexpression malic enzyme (ME) are described in Zhang 2016. Malic enzyme, when overexpressed by Rhodotorula, significantly increases lipid production. Malic enzyme generates NADPH, which is a known rate-limiting step during fatty acid synthesis in oleaginous red yeast. Increased expression of fatty acids, specifically 3-hydroxy fatty acids, may provide a boost in the key building block of polyol esters of fatty acids (PEFA) biosurfactants. For example, an expression plasmid for malic enzyme (pGI2-ME) can be constructed as follows. First, the native promoter for glyceraldehyde-3-phosphate dehydrogenase (GAPDH, GenBank accession no KU980962) and expressed gene along with its cognate terminator are PCR amplified from R. toruloides IFO0880 genomic DNA. Next, the plasmid pGI2 (Abbott et al. 2013) is linearized with the restriction enzymes AvrII and BamHI. The three DNA fragments are then ligated together using Gibson assembly (Gibson et al. 2009), yielding the plasmid pGI2-ME as shown in FIG. 1b of Zhang 2016.

In some embodiments, the ideal yeast strain would be deleted for the acetyltransferase responsible for biosurfactant acetylation, deleted for MFE-2 to block consumption of those biosurfactants when they are produced, and engineered to overexpress malic enzyme (or other lipid biosynthesis enzymes) to boost production of fatty acids that could be used by the yeast for surfactant synthesis.

In some embodiments, the ideal yeast strain would be deleted for the acetyltransferase responsible for biosurfactant acetylation, and deleted for MFE-2 to block consumption of those biosurfactants when they are produced.

In some embodiments, the method of providing a tunable biodegradable surfactant compound can be performed through chemical synthesis. In general, the tunable surfactant compound can be synthesized from a chemical reaction forming a covalent bond between a head portion and a tail portion, particularly an ester bond or an amide bond.

For example, a tunable surfactant compound can be synthesized by an esterification reaction of a tail portion comprising a carboxylic acid ($CO_2H$) with a head portion comprising a methylene hydroxyl group ($CH_2OH$).

Exemplary tunable surfactant compound can be synthesized by esterification of a fatty acid selected from Myristic acid ($CH_3(CH_2)_{12}COOH$), Palmitic acid ($CH_3(CH_2)_{14}COOH$), Stearic acid ($CH_3(CH_2)_{16}COOH$) Arachidic acid ($CH_3(CH_2)_{18}COOH$), Behenic acid ($CH_3(CH_2)_{20}COOH$), Lignoceric acid ($CH_3(CH_2)_{22}COOH$) and 3-hydroxy octadecanoic acid, Myristoleic acid ($CH3(CH2)3CH=CH(CH2)7COOH$), Palmitoleic acid ($CH_3(CH_2)_5CH=CH(CH_2)_7COOH$), Sapienic acid ($CH_3(CH_2)_8CH=CH(CH_2)_4COOH$), Oleic acid ($CH_3(CH_2)_7CH=CH(CH_2)_7COOH$), Elaidic acid ($CH_3(CH_2)_7CH=CH(CH_2)_7COOH$), Vaccenic acid ($CH_3(CH_2)_5CH=CH(CH_2)_9COOH$), Linoleic acid ($CH_3(CH_2)_4CH=CHCH_2CH=CH(CH_2)_7COOH$), Linoelaidic acid ($CH_3(CH_2)_4CH=CHCH_2CH=CH(CH_2)_7COOH$), α-Linolenic acid ($CH_3CH_2CH=CHCH_2CH=CHCH_2CH=CH(CH_2)_7COOH$), Arachidonic acid ($CH_3(CH_2)_4CH=CHCH_2CH=CHCH_2CH=CHCH_2$ CH=CH(CH$_2$)$_3$COOH), Eicosapentaenoic acid (CH$_3$CH$_2$CH=CHCH$_2$CH=CHCH$_2$CH=CHCH$_2$CH=CH(CH$_2$)$_3$COOH), Erucic acid (CH$_3$(CH$_2$)$_7$CH=CH(CH$_2$)$_{11}$COOH), and Docosahexaenoic acid (CH$_3$CH$_2$CH=CHCH$_2$CH=CHCH$_2$CH=CHCH$_2$CH=CHCH$_2$CH=CH(CH$_2$)$_2$COOH) with a polyol selected from Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Galactitol (6-carbon), Fucitol (6-carbon), Iditol (6-carbon), Inositol (6-carbon; a cyclic sugar alcohol), Volemitol (7-carbon) and HOCH$_2$ (CHOH)$_p$CH$_2$OH wherein p is 0-5.

In one exemplary embodiment, a tunable surfactant compound is synthesized by esterification of an alkenyl fatty acid with a polyol as shown in Scheme 1.

Scheme 1

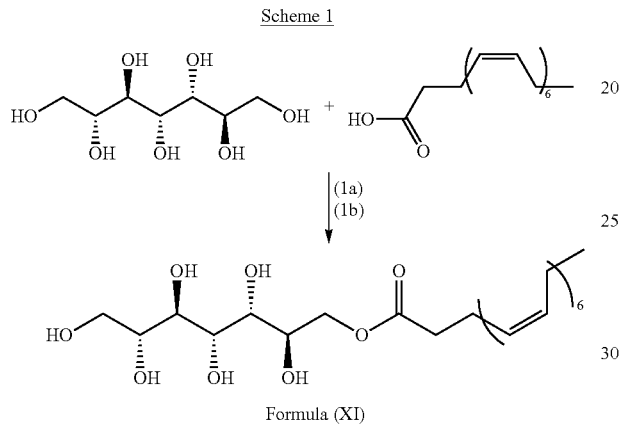

Formula (XI)

As shown in scheme 1, Volemitol (7-carbon) is coupled with Docosahexaenoic acid (DHA) to form a tunable biodegradable surfactant (XI). The reaction condition (1a) includes reacting Docosahexaenoic acid (DHA) with thionyl chloride (0.95 eq.) in dichloromethane to form Docosahexaenoyl chloride. In reaction condition (1b), docosahexaenoyl chloride is reacted with a suspension of Volemitol (7-carbon) in pyridine at ambient temperature to produce a tunable biodegradable surfactant of Formula (XI).

It is to be understood that reaction Scheme 1 is illustrative of reactions of other fatty acid and polyols to produce the corresponding tunable biodegradable surfactants as described herein.

In another exemplary embodiment, a tunable surfactant compound is synthesized by an amidation reaction of a tail portion comprising a carboxylic acid with a head portion comprising an amino group as shown in Scheme 2.

Scheme 2

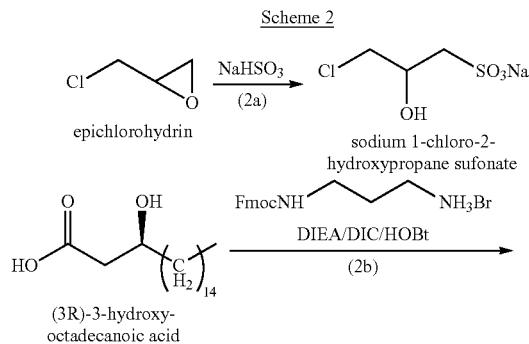

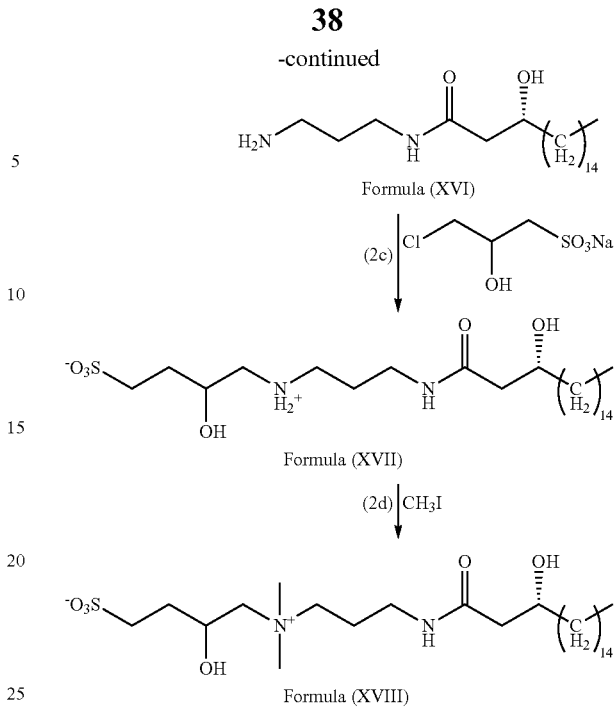

According to scheme 2, the step (2b) includes Fmoc (Fluorenylmethyloxycarbonyl) deprotection by piperidine in dichloromethane (DCM) or dimethylformamide (DMF).

According to a fourth aspect, a tuned biodegradable surfactant is described, the tuned biodegradable surfactant obtained by modifying the at least one tuning moiety of the tunable biodegradable surfactant herein described. The tunable biodegradable surfactant in this sense can also be referred to as a "base compound".

In some embodiments, a tuned biodegradable compound here described is represented by Formula (XXII) and optionally at least one counter ion Z:

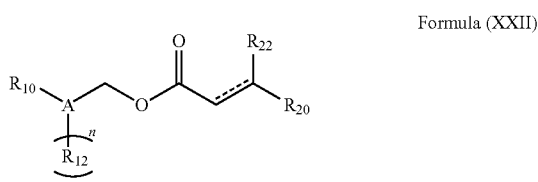

Formula (XXII)

wherein
------ represents a single or double bond when R21 is H, and a single bond when R21 is other than H;
n is 1-6;
A is a node moiety selected from a C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups;
wherein the R22 and each of R12 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy;
R10 is H, or C1-C2 alkyl group; and
R20 is a C11-C21 linear or branched alkyl, alkenyl, or alkynyl group.

In particular, in some embodiments, R22 can be an alkyl group that adds to the size and overall hydrophobicity of tail portion of the biodegradable surfactant. The tail portion of the biodegradable surfactant preferably can be a C16-C18 aliphatic moiety.

M some embodiments, R22 can be a C1-C6 substituted or unsubstituted linear or branched alkyl group. Exemplary embodiments of R22 includes methyl, ethyl, n-propyl, iso-propyl, n-butyl, isobutyl, or tert-butyl groups.

In some embodiments the nature of R12 is an OH group for the carbohydrate series and can be a NH₂ for the aminosugar series. As used herein, an aminosuger refers to a sugar moiety wherein at least one hydroxyl group of the sugar moiety is replaced with an amine group. In some embodiments aminosugar or its derivatives can contain at least one amino group. Preferably the amino group can be at the C2 position of a carbohydrate. Exemplary aminosugar includes but are not limited to glucosamine, galactosamine, fructosamine, and mannosamine.

In some embodiments, a tuned biodegradable compound herein described is represented by Formula (XXIII) and optionally at least one counter ion Z:

R10 is H, or C1-C2 alkyl group; and

R20 is a C11-C21 linear or branched alkyl, alkenyl, or alkynyl group.

In some embodiments, a tuned biodegradable surfactant has an aHLB value in a range selected from 15-20, wherein the tuned biodegradable surfactant is obtained by modifying a tunable biodegradable surfactant having aHLB value in a range selected from 5-10 or 10-15.

In some embodiments, the tunable moiety is comprised in head portion of a tunable biodegradable surfactant compound. Accordingly, the Group Number Gt of the tunable biodegradable surfactant compound is the same as the Group Number Gt of the tuned biodegradable surfactant compound.

In an exemplary embodiment, as shown in FIG. 25, Surfactant I of Formula (III) can be derivatized to a mono-sulfated-Surfactant (I) of Formula (III-1S) and further to a persulfated-Surfactant of Formula (III-6S), thus tuning the aHLB of Surfactant (I).

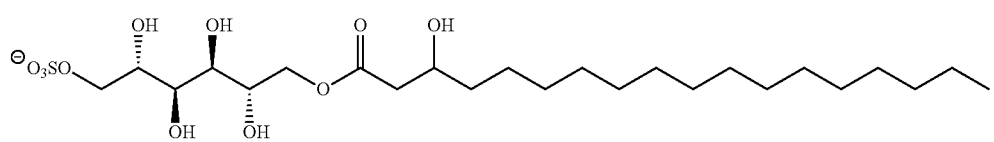

Monosulfated-Surfactant I

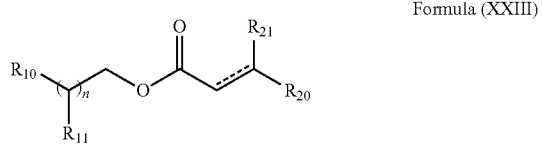

Formula (XXIII)

After tuning to monosulfated-Surfactant I of Formula (III-1S), the replacement of one tuning moieties (hydroxyl) with sodium sulfate, change to resulting aHLB to 16.69.

Further introduction of sulfate groups to a total of six of them for persulfated-Surfactant I of Formula (III-6S) further increase the resulting aHLB to 19.18, due to the dramatic increase of the hydrophilicity from that of sulfate (38.7) from hydroxyl (1.9).

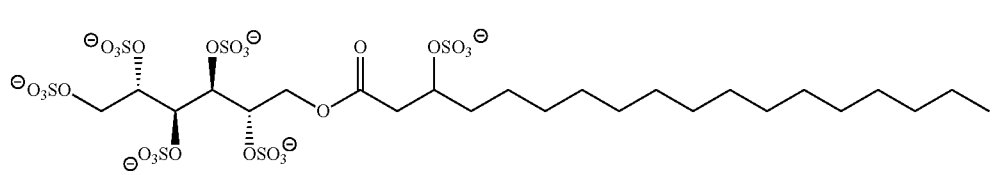

Persulfated-Surfactant I wherein

------ : represents a single or double bond when R21 is H, and a single bond when R21 is other than H;

n is 1-6;

wherein the R21 and each of R11 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy;

As the tail portion of the Formula (III), Formula (III-1S), Formula (III-6S) are the same, their corresponding Group Number Gt are also the same, being −7.125. Therefore, the tuning of the aHLB are a result of modification of tunable moiety OH to sodium sulfate group.

As illustrated by the replacement of one or six hydroxyl of Surfactant I, the aHLB changes from 11.69 to 16.69 and 19.18 for biodegradable surfactants of Formula (III), Formula (III-15) and Formula (III-6S) respectively.

According to a fifth aspect, a method of tuning a tunable biodegradable surfactant is described in which one or more tuning moieties of the tunable biodegradable surfactant are modified, resulting in a tuned biodegradable surfactant having a modified aHLB value. The methods allow for the same base molecule to be used as a biosurfactant, and modified to change the aHLB either through a chemical synthesis reaction or through the use of cloned and expressed recombinant enzymes such as acetyltransferases, sulfotransferases, and kinases.

In embodiments herein described, methods are described to control the hydrophilic-hydrophobic balance of a biodegradable surfactants herein described. In particular in some embodiments, a method of modifying a tunable biodegradable surfactant compound having a first aHLB to a tuned biodegradable surfactant compound having a second aHLB is described. The method comprises providing the tunable biodegradable surfactant having the first aHLB, the tunable biodegradable surfactant comprising at least one tunable moiety, modifying the at least one tunable moiety to at least one tuned moiety, and obtaining a tuned biodegradable surfactant having the second aHLB.

The method can further comprise providing a look-up table containing a list of Group Numbers each corresponding to a reference moiety, calculating a head-portion Group Number of the at least one tuned moiety, identifying the at least one tuned moiety having the head-portion Group Number from the look-up table, and converting the at least one tunable moiety of the tunable biodegradable surfactant into the at least one tuned moiety. An exemplary look-up table is shown in Table 1 in which each reference moiety corresponds to a Group Number. The calculation of the head-portion Group Number can be performed using Equation (1).

In some embodiments, the at least one tuned moiety comprises an anionic group and a cationic counter ion. Preferably the cationic counter ion is selected from the group comprising proton, ammonium, C-C4 tetraalkyl ammonium, sodium (I), potassium (I), cesium (I), magnesium (II), calcium (II), and zinc (II) or any combinations thereof.

In some embodiments, the at least one tuned moiety comprises a cationic group and an anionic counter ion. Preferably the anionic counter ion is selected from the group comprising inorganic sulfate ($SO_4^{2-}$), inorganic phosphate ($PO_4^{3-}$), tetrafluoroborate, hexafluorophospate, p-toluenesulfonate, benzenesulfonate, nitrate, trifluoroacetate, fluoride, chloride, bromide, and iodide or any combinations thereof.

It is to be understood by a person of skill in the art that the tuned moiety and the associated counter ion are in stoichiometric ratio to maintain an overall charge neutral of the biodegradable surfactants, including any tunable biodegradable surfactant and any tuned biodegradable surfactant.

In particular, the converting step comprises contacting the tunable biodegradable surfactant with at least one enzyme under conditions and for sufficient interval of time, thus providing a tuned biodegradable surfactant, wherein the at least one enzyme catalyzes the conversion of the at least one tunable moiety of the tunable biodegradable surfactant to the at least one tuned moiety of the tuned biodegradable surfactant. In particular, the tunable moiety can be a hydroxyl group and the tuned moiety can be an acetylate.

In some embodiments, the converting of at least one tunable moiety of the tunable biodegradable surfactant into at least one tuned moiety can be performed through chemical synthesis such as chemical acetylation, sulfation or phosphorylation.

In some of these embodiments, a tuned biodegradable surfactant compound of Formula (XXII) is chemically synthesized from a tunable biodegradable surfactant compound of Formula (XX) by at least one chemical reaction step, wherein n number of T tunable moieties and Q each independently selected from OH, or $NH_2$ are converted to R12 and R22 tuned groups independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy.

In some other embodiments, a tuned biodegradable surfactant compound of Formula (XXIII) is chemically synthesized from a tunable biodegradable surfactant compound of Formula (XXI) by at least one chemical reaction, wherein n number of T tunable moieties and Q each independently selected from OH, or $NH_2$ are converted to R12 and R22 tuned groups independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy.

Due to the particular structure of the tunable biodegradable surfactants described herein, one can "tune" the tunable biodegradable surfactants to be more hydrophilic or hydrophobic based on the number of acetylation groups on the base molecule. Less acetylation equates to more hydroxyl groups (which are polar, 'water loving') which scores higher on the aHLB scale (hydrophilic). More acetylation equates into capping of the hydroxyl groups (which are non-polar, 'oil loving') which scores lower on the aHLB scale (hydrophobic). Alternatively, addition of sulfate groups or phosphate groups can tune the tunable biodegradable surfactants to be more hydrophilic.

In some embodiments, converting at least one tunable moiety of the tunable biodegradable surfactant into at least one tuned moiety can be performed by employing one or more enzymatic process through the use of cloned, expressed enzymes such as acetyltransferases, sulfotransferases, and kinases, respectively, among other enzymes identifiable by those skilled in the art.

For example, following identification of the acetyltransferase(s) responsible for catalyzing the production of the acetylated polyol fatty acid esters in *Rhodotorula* or *Rhodosporidium* strains described herein as described in Example 12, the acetyltransferase enzyme(s) can be cloned into a suitable expression vector and expressed in a suitable expression system, such as a host cell, in vitro translation system or others known to those skilled in the art, following methods known to persons skilled in the art, such as those described in ref: A. Amid and N. Hassan, Recombinant Enzyme: Cloning and Expression. In Recombinant Enzymes—From Basic Science to Commercialization, A. Amid (ed.), 2015.

In addition to acetyltransferases, genes encoding enzymes capable of catalyzing other functional group modifications in biosurfactants can be cloned into expression vectors. Identification of genes, for example yeast genes, encoding enzymes capable of catalyzing modification of other functional groups in biosurfactants, such as sulfotransferases and kinases, for example, can be similarly performed by homology analysis of DNA, mRNA, or protein sequences of known enzyme gene sequences, available in NCBI and other databases known to those skilled in the art. Thereafter, polynucleotides encoding these enzymes can similarly be cloned into expression vectors for the purpose of catalyzing modification of biosurfactants to contain other functional groups, such as sulfates and phosphates.

In other embodiments, protein engineering methods can be used to provide new enzyme variants that are capable of catalyzing the modification of functional groups on biosurfactants described herein to produce biosurfactants with a modified aHLB. Methods known to those skilled in the art such as those based on rational design of modified enzymes and/or directed evolution techniques can be used to provide enzymes capable of modifying biosurfactants described herein. The term "rational design" means a process wherein detailed knowledge of the structure and function of a protein is used to make desired changes, employing site-directed mutagenesis and other methods known to those skilled in the art. The term "directed evolution" means a process wherein random mutagenesis is applied to a protein, and a selection regime is used to pick out variants that have the desired qualities, such as selecting for the capability to enzymatically modify functional groups of a biosurfactant. The advantage of directed evolution is that it requires no prior structural knowledge of a protein, nor is it necessary to be able to predict what effect a given mutation will have. Accordingly, the sequence and structure of known enzymes, such as acetyltransferases, sulfotransferases, or kinases, can be modified using protein engineering techniques to provide new enzyme variants with functional capacity to modify biosurfactants described herein to have a modified aHLB.

Polynucleotides encoding enzymes can be cloned using commercially available reagents from vendors such as Qiagen, Invitrogen, Applied Biosystems, Promega, and others, following standard molecular biology methods known in the art, such as those described in ref: Sambrook and Russell (2001). Synthetic DNA, genomic DNA or cDNA encoding acetyltransferases or other enzymes can be cloned into an expression vector. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences, as would be understood by a skilled person. Promoters can be constitutively active or inducible. RNA can be isolated from a cell, such as a yeast strain and cDNA produced by reverse transcription using standard techniques and commercial kits. Alternatively, genomic DNA can be purified from the cell, and cDNA or genomic DNA encoding one or more enzymes isolated, following methods known to those in the art. PCR-based amplification of the gene of interest can be performed using appropriately designed primer pairs (e.g. using PrimerDesign or other programs known to those skilled in the art). An encoded tag can be incorporated into the primer design (e.g. encoding a His-tag designed to be fused to the N- or C-terminus of the recombinant enzyme) to facilitate protein purification (e.g. using commercially-available His-tagged protein purification columns/kits) or for immobilization of the enzyme within a bioreactor, as described below. PCR-based amplification can be followed by ligation (e.g. using T4 DNA ligase) of the amplicon into an appropriate expression cassette in a plasmid suitable for propagation in bacteria or other cells, such as transformation-competent E. coli DH5alpha, followed by growth of transformed cell cultures, purification of the plasmid for confirmation of the cloned enzyme by DNA sequence analysis, among other methods known to those skilled in the art.

Cloned recombinant enzymes can be expressed using cell-based methods, or cell-free methods, following standard techniques and using commercially available kits. Cell-based methods for expression of recombinant enzymes can include expression in prokaryotic or eukaryotic cell cultures, such as E. coli or other bacterial cells, yeast strains, insect cells, or mammalian cells [16], among others known to those skilled in the art. Expression in yeast strains can be useful for ensuring appropriate post-translational modification of enzymes, and for secretory expression. Several yeast protein expression systems exist in organisms from the genera *Saccharomyces, Pichia, Kluyveromyces, Hansenula* and *Yarrowia*, that can be used for expression of recombinant enzymes. Yeast expression vectors that integrate into the host chromosome are most widely used because of their mitotic stability. Episomal expression vectors can also be used for some yeast systems. Expression vectors typically contain a strong yeast promoter/terminator and a yeast selectable marker cassette. Most yeast vectors can be propagated and amplified in E. coli to facilitate cloning and as such, also contain an E. coli replication origin and ampicillin selectable marker. Also, many yeast expression vectors include the ability to optionally clone a gene downstream of an efficient secretion leader (usually that of mating factor) that efficiently directs a recombinant protein to become secreted from the cell.

One yeast system that is commonly used for protein expression is *Kluyveromyces lactis*. For example, expression of recombinant enzyme(s) can be performed using commercially available reagents such as the K. lactis protein expression kit, K. lactis competent cells, and pKLAC expression vector (New England Biolabs), as described in Example 14, among others known to persons skilled in the art. The cloned expressed recombinant enzyme(s) can be affinity purified, for example using a commercially available hemagglutinin (HA) tag column or His-tag column purification kit, for cloned enzymes comprising an HA or His-tag sequence, respectively.

Recombinantly expressed enzymes can be incorporated into an enzymatic bioreactor where they can be used to catalyze functional group modification of compounds, such as biosurfactants. The term "bioreactor" means an apparatus in which a biological reaction or process is carried out, especially on an industrial scale, generally comprising a vessel or series of vessels that support a biologically active environment. Bioreactors used for enzymatic processes, such as acetylation, comprise those in which the enzymes are either free in solution, or in which enzymes are immobilized on a solid phase. The term "immobilization" refers to a technique of cell or particle attachment or entrapment, which can be applied to all types of biocatalysis including enzymes, cellular organelles, and cells. Immobilization is particularly useful for continuously operated processes, since the enzymes will not be removed with the reaction products. Immobilization of an enzyme can be performed by several means, such as physical (adsorption, entrapment, or encapsulation) or chemical (covalent binding). For example, chemical immobilization of an enzyme can be achieved using a tag attached to a recombinant enzyme, such as His-tag, which can bind to a solid phase, such as a physical support comprising chelated metal ions such as or $Ni^{2+}$ or $Fe^{3+}$, for example using commercially available kits such as EziG (EnginZyme), among other methods known to those skilled in the art. A recombinant enzyme (either free in solution or immobilized onto a solid phase), biodegradable surfactants and other necessary reagents, such as buffers containing chemicals required for modification of functional groups (e.g. buffers containing acetyl donor compounds, such as acetyl-CoA, for acetylation of surfactants) can be added to the bioreactor, and following incubation in the bioreactor under conditions and for a time appropriate for the enzymatic process to proceed until completion, identifiable by a skilled person, modified 'tuned' versions of the biosurfactant can be produced (e.g. acetylated surfactant compounds) that have a modified aHLB. The resulting 'tuned' biosurfactants can then be isolated from the bioreactor and purified, for example using solid-phase extraction methods described herein, among other methods known to those skilled in the art.

In some embodiments, a method of modifying a tunable biodegradable surfactant to result in a modified aHLB comprises a method in which cloned enzymes (such as acetyltransferases) are overexpressed within a cell, such as a yeast cell producing a biosurfactant as described herein, in order to generate modified 'tuned' versions of the biosurfactant. As described above, expression vectors for overexpression of an enzyme within a yeast can comprise plasmids, viral vectors, or non-viral vectors capable of transducing yeast known to those skilled in the art and can be integrating or non-integrating. Expression vectors can comprise suitable promoters, enhancers, post-transcriptional and post-translational elements for expression in yeast that are identifiable by those skilled in the art. Typically, yeast expression plasmids contain all the necessary components to allow shuttling between E. coli and yeast cells, to permit cloning methods using E. coli, as well as yeast-specific origin of replication (ORI) and a means of selection in yeast cells, in addition to the bacterial ORI and antibiotic selection markers. Yeast expression plasmids include but are not limited to yeast integrating plasmids (these plasmids lack an ORI and must be integrated directly into the host chromosome via homologous recombination), yeast replicating plasmids (containing an Autonomously Replicating Sequence (ARS) derived from the yeast chromosome and can replicate independently of the yeast chromosome; however, they tend to be unstable and may be lost during budding), yeast centromere plasmids (vectors that incorporate part of an ARS along with part of a centromere sequence (CEN); these vectors replicate as though they are small independent chromosomes and are thus typically found as a single copy; unlike the ARS vectors, CEN vectors are stable without integration), and yeast episomal plasmids (typically comprised of a fragment from the 2 micron circle (a natural yeast plasmid), allowing for 50+ copies to stably propagate per cell; the copy number of these vectors can also be controlled if specific regulatable elements are included), among others identifiable by a skilled person. Yeast can be transformed following methods known to those skilled in the art and positive transformants selected as described herein. The resulting genetically modified yeast overexpressing the enzyme(s) required for producing modified 'tuned' biosurfactants can then be grown in culture and the modified 'tuned' version of the biosurfactant comprising the enzymatically modified functional group(s) conferring a modified aHLB can be purified from the cells or growth media following methods outlined herein, among others known to those skilled in the art.

In accordance with the present disclosure, a composition is described comprising a biodegradable surfactant of the disclosure and at least one additive. As used herein, an additive refers to a chemical substance able to change pH value, ionic strength or ion concentration of a composition of biodegradable surfactant. In some embodiments, the total amount of the additive in the composition can be between 0.01% to 30% by weight based on the weight of the composition. In those embodiments the amount of surfactant can be between 99.9% to 70% by weight based on the weight of the composition.

In some embodiments, the composition can comprise one or more biodegradable surfactants herein described and in particular one or more biodegradable surfactants comprising an amphiphilic heteroatom containing hydrocarbon of Formula X-XVIII, XX-XXIII In some of these embodiments, the one or more biodegradable surfactants can have a amphiphlic heteroatom containing hydrocarbon of Formula X-XVIII, XX-XXIII and at least one additive, wherein the at least one additive can be between 0.01% to 30% by weight based on the weight of the composition, preferably in a total amount between 1% to 15% by weight based on the weight of the composition, and more preferably between 5% to 10% by weight based on the weight of the composition.

In some embodiments, the at least one additive is selected from and organic acid, inorganic acid, alkali hydroxide, alkaline earth hydroxide, alkali halide, alkaline halide, a metal chelating agent or a combination thereof. As used herein, alkali includes any one of atom or ion of lithium, sodium potassium, rubidium and cesium. As used herein, alkaline earth includes beryllium, magnesium, calcium, strontium and barium.

As used in the present disclosure, an organic acid is an organic compound that contains at least one ionizable hydrogen in water at pH 7. Exemplary organic acid as used herein includes but are not limited to formic acid, acetic acid, propionic acid, benzoic acid, lactic acid, chloroacetic acid, trifluoroacetic acid, methanesulfonic acid, fluoromethanesulfonic acid, trifluoroemthansulfonic acid, benzenesulfonic acid.

As used in the present disclosure, an inorganic acid is an inorganic compound that contains at least one ionizable hydrogen in water at pH 7. Exemplary inorganic acid as used herein includes but are not limited to hydrochloric acid, nitric acid, phosphoric acid, sulfuric acid, and boric acid.

In some embodiments, an anion of an ionized organic or inorganic acid is present as a counter ion for a cation group in a biodegradable surfactant.

In some embodiments, the at least one additive can be selected from and acetic acid, sulfuric acid, hydrochloric acid, sodium hydroxide, calcium hydroxide, EDTA or a combination thereof.

In some embodiments, the composition comprising a biodegradable surfactant herein described further comprise a carrier. As used herein, a carrier refers a liquid in which a biodegradable surfactant is able to dissolve in at least 1% by weight preferably at least 5% at room temperature. In particular in some embodiments the carrier can be selected from water, organic solvents, and combinations thereof. In some embodiments the total amount of the carrier being between about 0.01% and about 95% by weight based on the weight of the composition. In those embodiments, the amount of surfactant can be between 99.9% to 5% by weight based on the weight of the composition.

In some embodiments, the composition can comprise one or more biodegradable surfactants herein described and in particular one or more biodegradable surfactants comprising an amphiphilic heteroatom containing hydrocarbon of Formula X-XVIII, XX-XXIII In some of these embodiments, the one or more biodegradable surfactants can have an amphiphlic heteroatom containing hydrocarbon of Formula X-XVIII, XX-XXIII and at least one carrier, wherein the at least one carrier can be between 0.01% to 95% by weight based on the weight of the composition, preferably in a total amount between 50% to 90% by weight based on the weight of the composition.

In some embodiments, the organic solvent may be a polar aprotic organic solvent, a polar protic solvent. A polar aprotic solvent can be selected from the group comprising tetrahydrofuran (THF), ethyl acetate, acetone, dichloromethane, dimethylformamide (DMF), acetonitrile (MeCN), dimethyl sulfoxide (DMSO), nitromethane, propylene carbonate or any combination thereof. A polar protic organic solvent can be selected from the group comprising methanol, ethanol, n-propanol, isopropanol, n-butanol, formic acid, acetic acid or any combination thereof. In some embodiments, the organic solvent can be selected from C1-C4 alcohol, ethylene glycol, 1,2-propanediol or combination thereof.

In some embodiments, the composition comprising a biodegradable surfactant herein described can further comprise a carrier and an additive. In some of these embodiments one or more carrier can be comprised in an amount from 0.01% to 95% by weight based on the weight of the composition, the additive can be comprised in an amount from 0.01% to 30% by weight based on the weight of the composition and the biodegradable surfactant can be comprised in an amount from 99.8% to 5% by weight based on the weight of the composition. A skilled person will be able to understand the ratios of the components of a composition of the disclosure based on the intended application of the composition. Preferably the composition herein described can comprise an additive in an amount from 5% to 1% by weight based on the weight of the composition, a carrier in an amount from 90%% to 50% by weight based on the weight of the composition and a surfactant in an amount from 49% to 5% by weight based on the weight of the composition.

In some embodiments, the biodegradable surfactants and/or related compositions can be comprised in a system to control the hydrophilic-hydrophobic balance of a biodegradable surfactant. The system comprises one or more biodegradable surfactants herein described presenting one or more tunable moieties, and one or more reagents capable of modifying one or more tunable moiety of the one or more biodegradable surfactants. In composition and systems herein described the one or more biodegradable surfactants and the one or more additive, one or more carrier, and/or one or more reagents are chemically compatible.

As used herein, the term "chemically compatible" refers to the state of being chemically unreactive of a biodegradable surfactant to the agent when they are in contact. An agent is a chemical compound having a specific chemical or physical property. The specific chemical property, for example, including metal ion chelating property, or oxidation property.

In some embodiments, the one or more reagents can comprise an oxidant wherein the oxidant is selected to be reactive to the target organic compound. For example, the oxidant can be hydrogen peroxide.

In some embodiments, systems herein described can be provided in form of kit of parts.

Biodegradable surfactants, tunable biodegradable surfactants and related compositions and kits of parts herein described can be used in many industrial sections. Cationic and aphoteric biodegradable surfactants can be used in cosmetics industry. The main uses in the cosmetics industry are in soaps and shampoos (surfactants act as cleansing and foaming agents), conditioners (in conditioners, surfactants act as wetting agents and softening agents), toothpaste (surfactants act as foaming and cleaning agents in toothpastes), and moisturizers. The main uses in the oil and gas industry are as a de-emulsifying agent which modify the surface energy of oil and water to facilitate their separation, which in turn increases oil recovery (in oil extraction, oil remediation). In cleaning, anionic surfactants are used; the main sectors where surfactants are used in cleaning industry are in detergents (other than domestic detergents, surfactants are also used in hard surface cleaners, laundry washers, and dish washers; here they act as cleaning agents, dispersing agents, and foaming agents), and fabric softeners (cationic surfactants are used as fabric softeners; here they act as softening agents). In agriculture, cationic, anionic and amphoteric surfactants are used; the major uses in agriculture industry are in herbicides (surfactants increase the penetrability of herbicides; mainly non-ionic surfactants are used as herbicides), pesticides (surfactants are used in pesticides with the same functionality as in herbicides), and biocides (surfactants are used in biocodes to increase the wettability and penetration of the biocide). In the paint industry, mainly cationic, anionic and non-anionic surfactants are used; the primary uses of surfactants in the paint industry are in adhesives (the surfactant modifies the surface energy of the substrate to give better adhesion), anti-fog agents (the emulsifying property of surfactant is used to prevent fogging in paints), and printing inks (surfactant is used in printing ink as an additive to modify the surface energy of the substrate to provide better adhesion of ink). In the healthcare industry, surfactants are used in the medical industry (non-ionic and amphoteric surfactants are mainly used in the medical industry) and in drug manufacture (surfactants are used as emulsifying agents in the manufacture of drugs). In the food industry, surfactants are used as emulsifiers.

In some embodiments, a method of separating a target organic compound from a substrate is described, the method comprising contacting a biodegradable surfactant (e.g. within a related composition herein described) with the substrate comprising the target organic compound selected from volatile organic compound, halogenated volatile organic compound and polyaromatic hydrocarbon, agitating the mixture to form a mixture of at least two phases for a sufficient interval of time, thus separating the target organic compound from the substrate. In some cases, the substrate can be a soil contaminated with the target organic compound.

In some embodiments, the method of separating a target organic compound from a substrate further comprises adding an oxidant to the mixture after separating the target organic compound from the substrate such that the target organic compound is oxidized by at least 1%, preferably 50%, and more preferably 99%.

In some embodiments, a method for separating a biodegradable surfactant from aqueous solutions using solvent sublation is described. As used herein, solvent sublation, gas stripping, and aqueous two-phase system (ATPS) separation are interchangable. Solvent sublation as described herein is a kind of adsorptive bubble separation technique in which the biodegradable surfactant in aqueous phase are adsorbed on the bubble surfaces of an ascending gas stream and then collected in an organic layer placed on top of the aqueous phase. [17] [18] [19] [20] [21] [22].

In several embodiments, biodegradable surfactant herein described can be used as a dispersing agent, as a cleaning agent, as an emulsifying agent, as a foaming agent as a defoaming agent and/or as a wetting agent. In particular, as a dispersing agent, a surfactant can be added to a solid surface to reduce the surface energy of the solid so that the flow of a liquid on that surface can take place smoothly. As a cleaning agent, the surfactant molecule captures the oil or dirt molecule in the form of micellization in a solvent- or water-based medium. As an emulsifying agent, when surfactant is added to a mixture of two immiscible liquids, it reduces the surface energy of both the liquids and makes them miscible by forming an emulsion. Acting as a foaming agent, a surfactant increases colloidal stability and reduces the coalescence of bubbles, thereby increasing stability of foam formation. As a de-foaming agent, the surfactant increases the coalescence of bubbles by reducing the surface energy between the liquid and the bubble surface, thereby reducing foam stability. As a wetting agent, when a surfactant is added to a water repellant surface, it reduces the equilibrium and dynamic surface energy of the substrate, thereby increasing the water infiltration in the substrate.

Further details concerning the biodegradable surfactant, and related compositions methods and systems of the present disclosure will become more apparent hereinafter from the following detailed disclosure of examples by way of illustration only with reference to an experimental section.

EXAMPLES

The biodegradable surfactants and related composition, systems and methods herein disclosed are further illustrated in the following examples, which are provided by way of illustration and are not intended to be limiting.

In particular, the following examples illustrate exemplary methods and protocols for preparing biodegradable surfactants. A person skilled in the art will appreciate the applicability and the necessary modifications to adapt the features described in detail in the present section, to additional biodegradable surfactants and related methods and systems according to embodiments of the present disclosure. The following materials and methods were used.

Culturing of *Rhodotorula* and *Rhodosporidium* Strains.

*Rhodotorula bogoriensis* was obtained from the American Type Culture Collection (ATCC 18809); *R. taiwanensis* (MD1149) was obtained through M. J. Daly at the Uniformed Services University of the Health Sciences (USUHS); *Rhodosporidium babjevae* (EXF-513/MD1169) was acquired via M. J. Daly through the Ex Culture Collection of Extremophilic Fungi, a part of the Infrastructural Centre Mycosmo (MRICUL) at the Department of Biology, University of Ljubljana, Slovenia. All yeast strains were grown in yeast mold broth (YM, Difco #271120) overnight at 25° C. and diluted to 0.05 $OD_{600}$/mL in Hommel's minimal salts (HMS, per liter—3 g $(NH_4)_2SO_4$, 0.5 g NaCl, 0.7 g $MgSO_4$, 0.4 g $Ca(NO_3)_2$, 0.4 g $K_2HPO_4$, 2.5 g $KH_2PO_4$) supplemented with 0.6 g/L yeast extract (Difco #210929) and 50 g/L glucose. At the indicated time (2, 4, 6 and 8 days), $OD_{600}$ was assessed and 10 mL of culture were centrifuged twice at 5000*g to obtain spent liquid medium (SLM) for assays.

Surface Tension Measurements (Tensiometry).

The surface tension was measured by the Wilhelmy plate method [23]. This method utilized a roughened platinum plate at room temperature coupled to a Kruss K11 force tensiometer. The Kruss measurement parameters used were as default with the exception of the following: Max measure time—2000 s; # of values—200 and standard deviation—0.1 mN/m.

Solid Phase Extraction.

Biosurfactant compounds were purified from spent liquid medium using a 60 mL (10 g) Discovery C18 solid phase extraction tube (Supelco). The sorbent was conditioned with 50 mL of LC-MS grade methanol (Burdick and Jackson), followed by 50 mL of LC-MS grade water (Burdick and Jackson). Spent liquid medium was then added to the column (~40 mL), and allowed to flow through the column using gravity filtration (no vacuum). The column was then washed with an equal volume of water, followed by equal volumes of 20%, 40%, 60%, 80% and 100% methanol. Starting material, wash, and all eluates were then analyzed by LC-MS to determine in what fraction the compounds of interest eluted. The fraction of interest was then evaporated to dryness using a Savant SPD111V speedvac concentrator (Thermo Scientific) in preparation for composition analysis.

Glycosyl Composition and Fatty Acid Analysis.

Biosurfactant composition analysis was performed by combined gas chromatography/mass spectrometry (GC/MS) of the per-O-trimethylsilyl (TMS) derivatives of the monosaccharide methyl glycosides and fatty acid methyl esters produced from the sample by acidic methanolysis as described previously by Santander et al. (2013) *Microbiology* 159:1471[24]. Briefly, the samples (200-300 µg) were heated with methanolic HCl in a sealed screw-top glass test tube for 18 h at 80° C. After cooling and removal of the solvent under a stream of nitrogen, the samples were treated with a mixture of methanol, pyridine, and acetic anhydride for 30 min. The solvents were evaporated, and the samples were derivatized with Tri-Sil® (Pierce) at 80° C. for 30 min. GC/MS analysis of the TMS methyl glycosides was performed on an Agilent 7890A GC interfaced to a 5975C MSD, using an Supelco Equity-1 fused silica capillary column (30 m×0.25 mm ID). Fatty acid standards were purchased from Laradon.

High Resolution Liquid Chromatography-Electrospray Ionization-Mass Spectrometry (LC-ESI-MS).

Biosurfactants were detected in aqueous medium using an Agilent 6550 Accurate-Mass TOF LC-MS system. A reversed-phase Zorbax Eclipse Plus C18 (RRHD) column (2.1×100 mm, and 1.8 µm particle size) was used at 30° C. in an Agilent 1290 HPLC Separation Module connected to a Agilent 6550 iFunnel Q-TOF LC-MS system equipped with a an Agilent Jet Stream II dual sprayer ESI source. Mobile phases consisted of water-formic acid (99.9%:0.1%) (solvent A) and 100% acetonitrile (solvent B). The following solvent composition program was used: isocratic 0.5 min of 20% of solvent B, gradient for 19.5 min until 95% solvent B, isocratic 10 min with 95% solvent B, then an equilibration time of 5 min (post time). The flow rate was kept constant at 0.3 mL/min, the injection volume was 10 µl (with needle wash), and the samples were maintained at 4° C. inside the autosampler. The LC-MS instrument was operated in positive ion electrospray mode with an acquisition range of 115-1700 amu with a scan rate of 3 spectra/sec. The source was kept at 225° C. with a gas flow of 17 l/min, and a sheath gas temperature of 380° C. and sheath gas flow of 12 l/min. The VCap was set at 3500, the nozzle voltage at 500 V, the fragmentor at 150, Skimmer1 to 0, and octopole RF peak to 750. Data acquisition was performed using Agilent MassHunter LC-MS Data Acquisition Software (version B.05.01, build 5.01.5125.2). Data analysis was performed using Agilent MassHunter Qualitative Analysis Software (version B.06.00, build 6.0.633.0).

Example 1. Comparison of Biosurfactants Produced by *R. bogoriensis* and *R. taiwanensis*

*R. bogoriensis*, the first *Rhodotorula* species described as a sophorolipid producer [25], has continued to be a well-studied organism for biosurfactant production under different carbon and nitrogen sources [26, 27]. In the course of characterizing biosurfactants produced by *R. bogoriensis*, a systematic screen of other *Rhodotorula/Rhodosporidium* isolates for "novel" biosurfactant production was begun, i.e. for biosurfactant compounds that were markedly different from those produced by *R. bogoriensis*. In the course of screening multiple strains for reduced surface tension in the growth medium, *R. taiwanensis* was identified as a potential candidate for new biosurfactant production.

To confirm this, R. bogoriensis and R. taiwanensis strains were grown side-by-side for eight days in a minimal glucose medium supplemented with yeast extract, and measured every two days for dramatic drops in surface tension. In addition, samples were subjected to accurate mass LC-MS analysis to confirm the presence of a biosurfactant in the medium if a drop in surface tension was observed. As shown in FIG. 1A, an immediate drop of surface tension was noted in the medium of R. bogoriensis at day two, which stayed low for the duration of the time-course (ending at 33.8 mN/m). It is noteworthy that microbes that produce biosurfactants typically lower the surface tension of the growth medium from ~70 mN/m down to 25-35 mN/m [2]. LC-MS analysis revealed the presence of biosurfactants in the medium which were denoted by the triangle above the total ion chromatograms in FIG. 1B; these amphiphilic compounds elute later in the chromatographic gradient due to their fatty acid chains binding to the C18 column (thereby needing a higher % of organic solvent to elute), and are well separated from the more polar components in the growth medium that elute early in the LC-MS run.

High-resolution mass spectrometry measured the accurate mass of these *Rhodotorula bogoriensis* compounds. An accurate mass measurement ("measured ion mass"), when compared to the calculated mass of an ion based on its elemental formula ("exact ion mass"), provides input for the mass accuracy calculation $\Delta m_i = (m_i - m_a)/m_a \times 10^6$ in parts per million (ppm) where $m_i$ is the measured ion mass and $m_a$ is the exact ion mass. Mass accuracy subsequently determines the theoretical number of elemental formula that could match a particular ion species (reviewed in [28]). It is noteworthy that the mass accuracy for compounds measured was <1 ppm (FIG. 1C), and matched only one elemental formula with the elements C, H, N, and O. These ion masses and formulae corresponded with the published masses of four sophorolipid species previously described for R. bogoriensis [26, 27]: deacetylated (C22:0 SL), monoacetylated (C22:0-6" Ac SL, C22:0-6' Ac SL), and diacetylated (C22:0-6', 6" Ac SL).

Figure 1D:
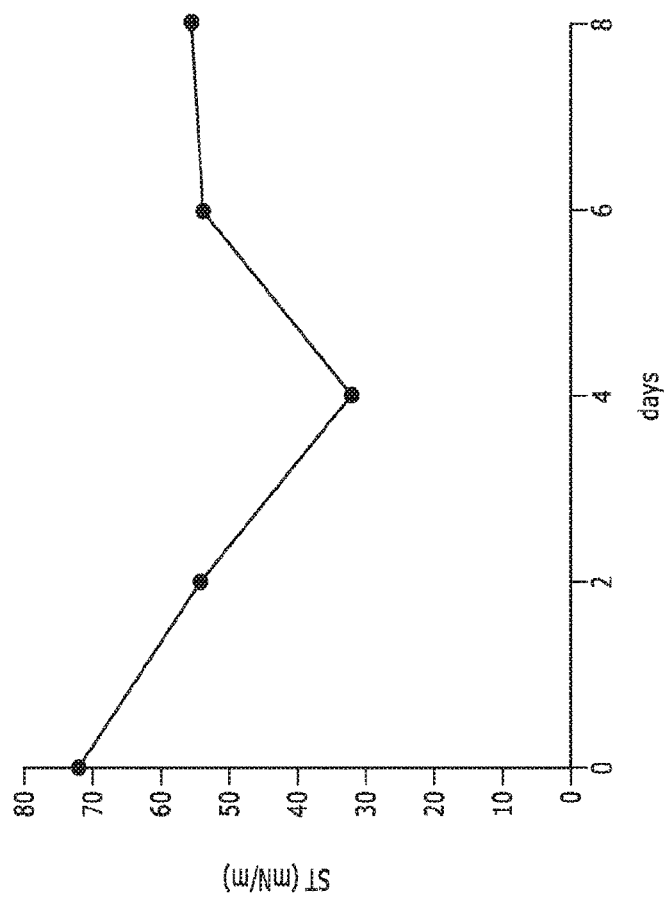
FIG. 1D shows a graph of exemplary growth medium surface tension (ST, in mN/m) measured over the time period shown for *R. taiwanensis*, which produced novel biosurfactant compounds that transiently lowered the surface tension of the culture medium, which corresponded with their appearance, and subsequent disappearance, in the LC-MS total ion chromatograms, which show results for day 0 (d0), day 2 (d2), day 4 (d4), day 6 (d6), and day 8 (d8) (FIG. 1E, indicated by the triangle). It was noted that these biosurfactants had different masses compared to *R. bogoriensis* sophorolipids, and eluted later in the LC-MS run (indicating they were more hydrophobic).
Figure 1E:
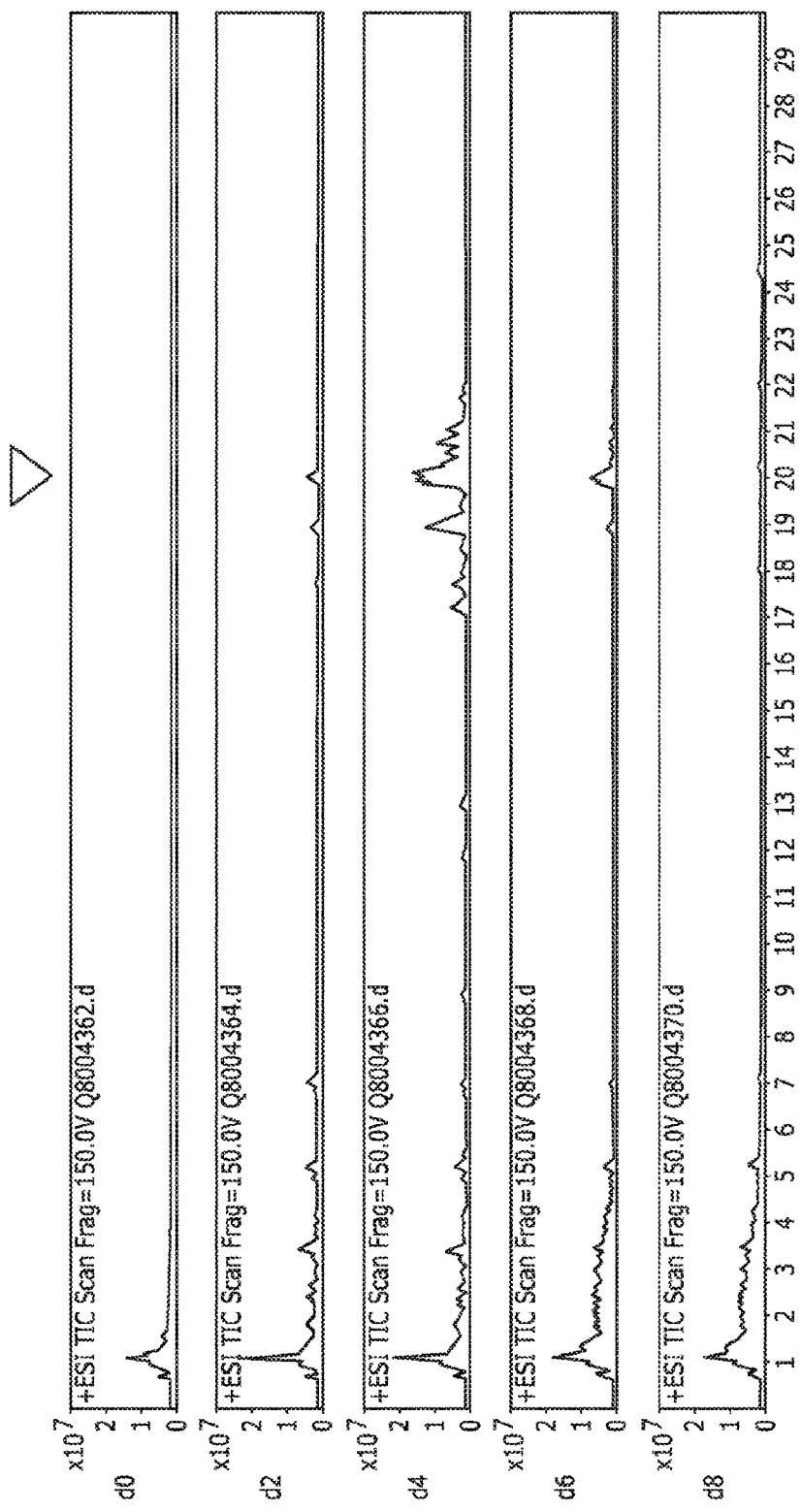
FIG. 1 shows biosurfactant production of *Rhodotorula bogoriensis* (control) compared to *Rhodotorula taiwanensis*.
FIG. 1C shows a table showing the accurate mass of the four main sophorolipid species was measured and confirmed.

By comparison, the surface tension profile of R. taiwanensis was markedly different; the surface tension dropped steadily down to ~32 mN/m over 4 days (log phase), then rose dramatically by day 6 (stationary phase), suggesting that the surface-active compounds were only transiently present in the culture (FIG. 1D). LC-MS analysis confirmed this finding, demonstrating that biosurfactants in the growth medium peaked in concentration at day 4, and then quickly decreased by day 6 (denoted by the grey triangle above the total ion chromatograms in FIG. 1E). We also noted that the surface-active compounds produced by R. taiwanensis were more hydrophobic than the sophorolipids produced by R. bogoriensis as observed by the longer retention time on the C18 column. The masses of the biosurfactants produced by R. taiwanensis compounds were also notably different than those reported for the sophorolipids produced by R. bogoriensis, and did not match any published masses for known biosurfactants.

Example 2. Exemplary Biodegradable Biosurfactant Produced by R. taiwanensis

Based on the appearance—and subsequent disappearance—of the biosurfactants in the culture medium (FIG. 1E), it was hypothesized that these compounds were biodegradable, i.e. degraded directly by R. taiwanensis, and did not breakdown due to an inherent instability of the compounds in an aqueous environment. To test this idea, a culture of R. taiwanensis was prepared as previously described. During maximum biosurfactant production (day 4), the culture was split as illustrated in FIG. 2. Half of the culture was allowed to continue shaking at 25° C. including cells; the other half of the culture was briefly centrifuged to remove cells, and the spent medium alone was transferred to a new flask and continued to shake at 25° C. A small volume of SLM was removed at days 5, 6, and 7 for LCMS analysis and side-by-side comparison for biosurfactant concentration. For the culture that was allowed to continue with cells, a similar pattern was observed as before; biosurfactant concentration was reduced to 34% by day 5, and 14% by days 6 and 7 (FIG. 2, left chromatograms). By comparison, the culture that had cells removed maintained a steady concentration of biosurfactant in the SLM (FIG. 2, right chromatograms). These findings suggest that the biosurfactant produced by R. taiwanensis is indeed biodegradable.

Figure 3:
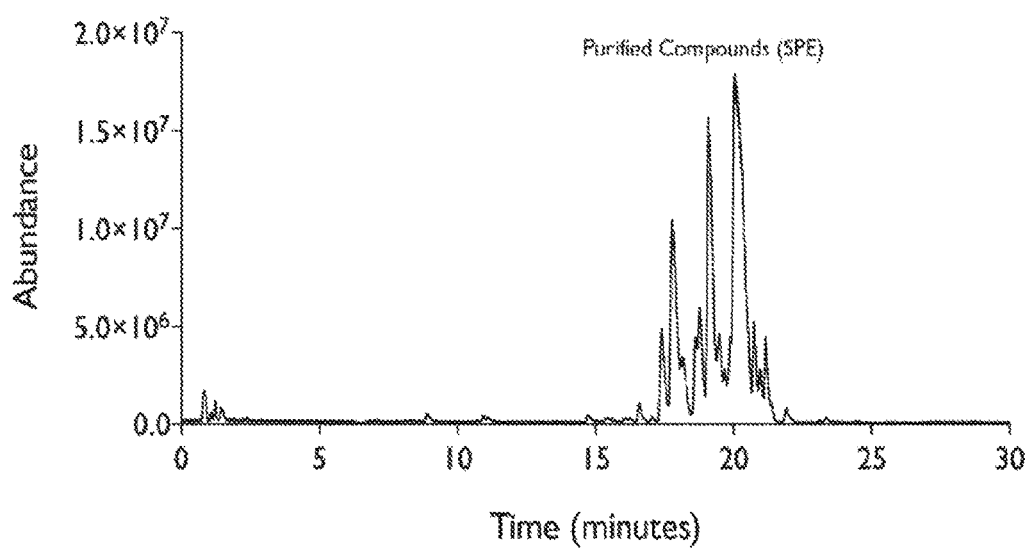
FIGS. 3-4 show biosurfactants produced by *R. taiwanensis* are polyol fatty acid esters.

Example 3A. Solid Phase Purification of Biosurfactant Compounds from Culture Medium In order to better characterize the composition and structure of these compounds, the biosurfactants from the culture medium were purified using solid phase extraction (SPE). SPE is a sample preparation method that passes a liquid sample over a "bed" of solid particles that are normally packed into a column. Depending on the type of particles used, compounds of interest will bind to the column while other interferences/contaminants pass through the column and are removed; compounds of interest can then be eluted from the solid phase particles using relevant solvents. Given the hydrophobic nature of the compounds, a C18 SPE column (reversed-phase) was used that is well known to bind hydrophobic compounds; the column was then gently washed and compounds were eluted from the column using an increasing amount of organic solvent (methanol). Polar and partially-polar compounds were eluted from the column using 20%, 40%, 60% methanol (data not shown). The compounds of interest begin eluting from the column at 80% methanol, and were fully removed using 100% methanol as examined by LC-MS analysis (FIG. 3).

Example 3B. Recovery of Tunable Biosurfactants by Solvent Sublation

Biodegradable surfactant can be recovered from aqueous solutions using solvent sublation. As used herein, solvent sublation, gas stripping, and aqueous two-phase system (ATPS) separation are interchangable. The separation of biodegradable biosurfactants produced by R. taiwanensis by sublation alleviates environmental concerns of any undesirable chemicals being released into the environment.

The approach as described herein can be used to purify tunable biosurfactants from aqueous spent liquid medium (SLM). Rhodotorula strains will be cultured in nutrient-rich broth (at which time the biosurfactants will be secreted into the medium). Yeast cells are removed through filtration or centrifugation, thereby leaving the SLM. The SLM is transferred into a gas stripping/sublation vessel where nitrogen gas will be bubbled up from the bottom of the vessel, driving surfactant compounds to the surface. Alternatively, this process can also be continuous in a simple bioreactor which normally bubbles in air from the bottom of the vessel to keep the culture aerobic. The surfactant foam is skimmed off directly from the surface, or be driven into an overlay of an organic solvent immiscible with water, preferably ethyl acetate. The organic solvent will then be evaporated, leaving highly-enriched biosurfactant material containing at least 95% by weight of the biosurfactant with respect to the total weight of the material.

Example 4. GC-MS Analysis of SPE-Purified Biosurfactant Compounds

Figure 4:
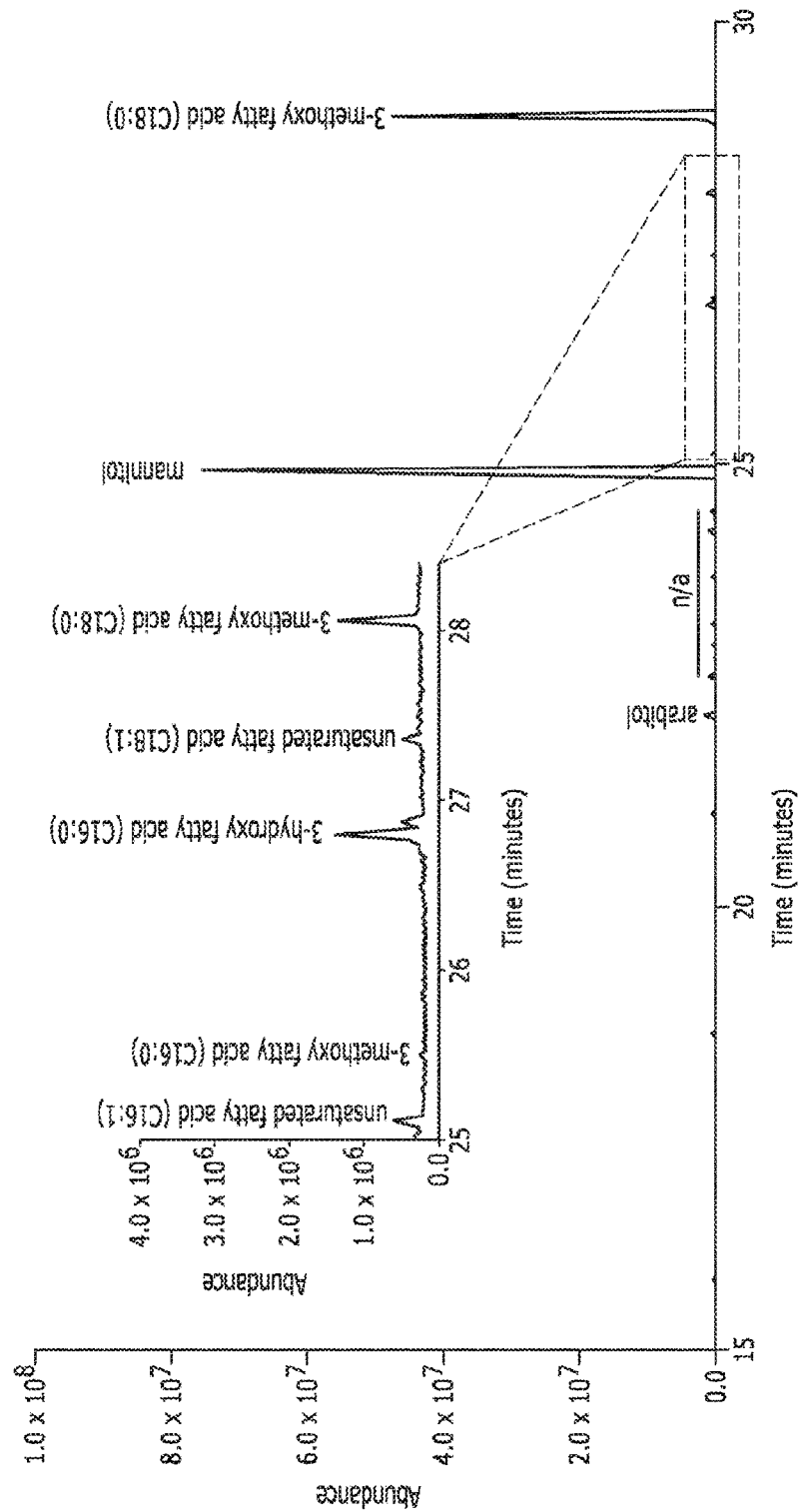

It has been reported that yeast species can produce a wide variety of extracellular glycolipids such as sophorolipids, ustilagic acid, and mannosylerythritol lipids (reviewed in [29]; therefore, it was hypothesized that the compounds produced by *R. taiwanensis* were also a type of fatty acid glycoside. To test this idea, the solvent was evaporated from the 100% methanol eluate, and the dried material was digested, derivatized (silylated), and analyzed by gas chromatography—mass spectrometry (GC-MS). This method was used to determine the composition of glycolipids by separating the carbohydrate and fatty acid moieties through acid hydrolysis of the ester linkage(s) [2]. Subsequent silylation increased the volatility of the sugar moiety by replacing the hydrogen of the —OH groups with trimethylsilyl [30]. Derivatized sugars and fatty acid methyl esters (or fatty acids) could then be analyzed side-by-side in the same GC-MS run. Analysis revealed that *R. taiwanensis* produced glycolipids composed of the sugar alcohols mannitol and arabitol (TMS derivatives), as well six main fatty acid constituents: 3-hydroxy stearic acid (C18:0), 3-hydroxypalmitic acid (C16:0), 3-methoxystearic acid (C18:0), 3-methoxypalmitic acid (C16:0), octadecenoic acid (C18:1, double bond in 2 position), and hexadecenoic acid (C16:1, double bond in 2 position). The relative abundances of these constituents are shown in FIG. 4, with mannitol and 3-hydroxy stearic acid (C18:0) being more abundant in the mixture (note: the mass spectra and retention times of these compounds were confirmed through a comparison with authentic standards). The relative abundance of the sugar alcohols to the fatty acids also showed that the they are in a 1:1 ratio, suggesting biosurfactants produced by *R. taiwanensis* are a mixture of polyol fatty acid esters; these compounds are similar in composition to extracellular glycolipids reported by Tulloch and Spencer in 1964 by *Rhodotorula graminis* and *Rhodotorula glutinis*, although no structural or speciation analysis was possible at the time [31].

Figure 6:
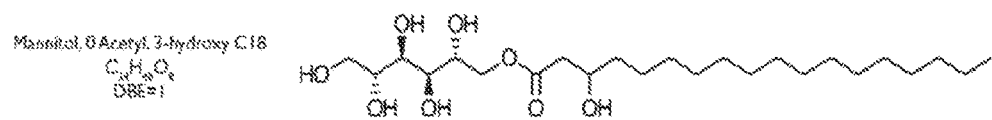

Example 5. Molecular Formulas and Structures of Detected Mannitol Biosurfactant Compounds Therefore, based on the GC-MS composition data, theoretical molecular formulae and structures were built of these compounds based on their constituent components. As the SLM of *R. taiwanensis* cultures (n=3) had already been analyzed by high-resolution liquid chromatography-electrospray ionization-mass spectrometry (LC-ESI-MS), a targeted analysis of the accurate mass data using MassHunter Software was conducted with the calculated molecular formula. It is noteworthy that MassHunter uses a search algorithm that finds compounds via accurate mass compared to theoretical mass (of the formula), isotope abundance, and isotope spacing. Any one of three potential adducts of the compounds ($[M+H]^+$, $[M+NH_4]^+$, $[M+Na]^+$) were also searched for, taking into account that adduct formation can be highly variable depending on the structure of the compound, the ion milieu of the spent liquid medium, and the mobile phase modifiers. As shown in FIG. 5 (first row), mannitol connected to a 3-hydroxy C18 fatty acid was readily identified by LC-MS given their abundance, with an accurate mass of <0.26 ppm (confirming that there is no other molecular formula that fits the measured ion mass). The structure of this compound is shown in FIG. 6, and fits the calculated double bond equivalent (DBE) value—a "degree of unsaturation" calculator often used by structural chemists—to predict the number of double bonds in a proposed structure from a molecular formula; the mannitol 3-hydroxy C18 is calculated to contain a single double bond based on its formula, and does (FIG. 6).

Figure 7:
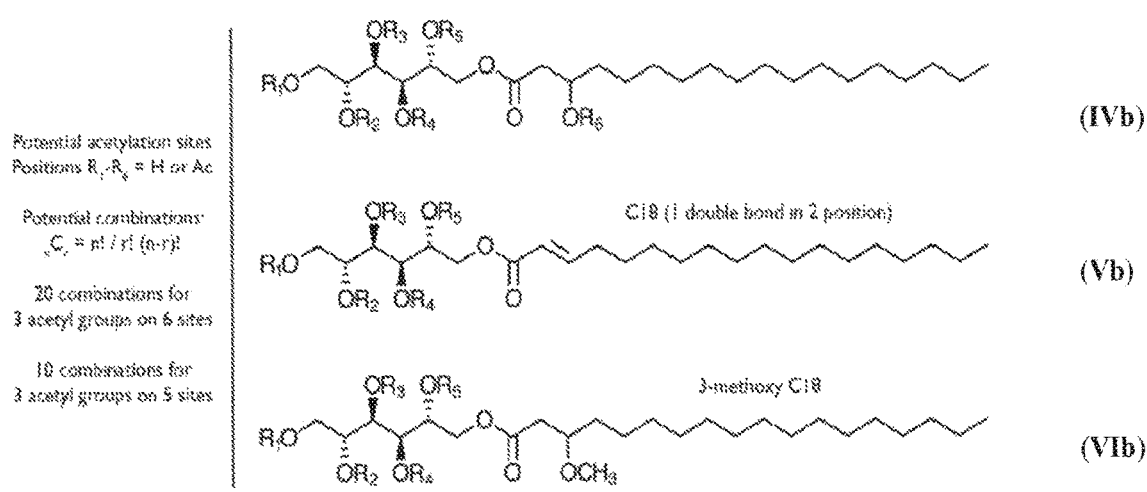

The LC-MS data also showed a series of acetylated mannitol 3-hydroxy C18 compounds (FIG. 5), which were not detected by GC-MS analysis (due to acid digestion of the compounds which would remove the acetyl groups). Acetylation is readily detected by high-resolution mass spectrometry when an acetyl group ($CH_2CO$) replaces the hydrogen on a hydroxyl group (OH), resulting in the addition of 42.0106 amu to the mass of the compound. Acetylation has been reported for a variety of other yeast extracellular glycolipids, including sophorolipids, ustilagic acid, and mannosylerythritol lipids (MELs) [29]. Interestingly, these characterized glycolipids are only acetylated at two potential sites. By contrast, polyol fatty acid esters produced by *R. taiwanensis* have an increased number of potential acetylation sites based on their structure. For example, mannitol 3-hydroxy C18 has six potential acetylation sites (FIG. 7). Interestingly, only compounds that contained 0-4 acetyl groups were detected, with mannitol containing 3 acetyl groups being the most abundant in the SLM (compounds are listed in FIG. 5). Furthermore, only mannitol (3 acetyl groups) with 3-methoxy C18 and C18 (one double bond) fatty acids were detected by LC-MS; structures are shown in FIG. 7. Using the factorial equation $_nC_r=n!/r!(n-r)!$, with "n" representing the potential number of acetylation sites and "r" representing the number of acetyl groups, the total number of 3 acetyl combinations on the three different polyol C18 fatty acid esters were determined (FIG. 7), e.g. 20 different acetylation combinations exist for the mannitol 3-hydroxy C18 backbone. These combinations would have the exact same mass, but slightly different retention times. Multiple retention times of the same mass were detected for this compound species, supporting the notion that multiple acetylation combinations exist in the mixture. However, it cannot be definitely stated where those acetyl groups are positioned on the mannitol 3-hydroxy C18 compound.

Figure 9:
Figure 13:
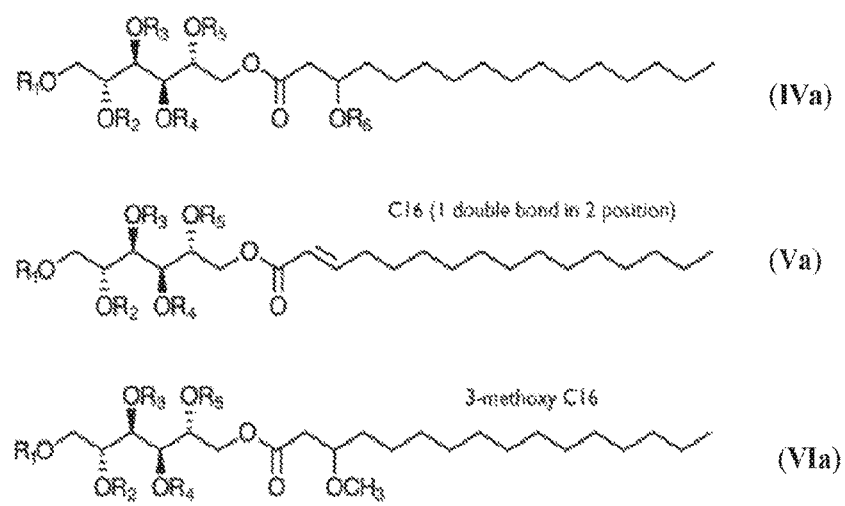
Figure 15:
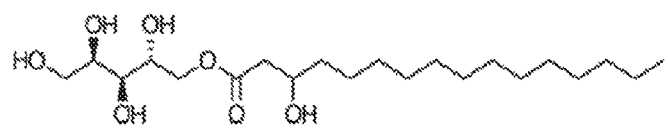

Example 6. Molecular Formulas and Structures of Detected Arabitol Biosurfactant Compounds Consistent with the GC-MS data, an arabitol acetylation series of 3-hydroxy C18 compounds was also detected (FIG. 8), with the structure of the base compound shown in FIG. 9. Similar to mannitol, the 3 acetyl groups was the most abundant version; only arabitol (3 acetyl groups) with 3-methoxy C18 and C18 (one double bond) fatty acids were detected by LC-MS. To further illustrate the complexity of this biosurfactant mixture, a mannitol acetylation series of 3-hydroxy C16 compounds was also detected (FIG. 11) and an arabitol acetylation series of 3-hydroxy C16 compounds was also detected (FIG. 14). In both cases, the "3 acetyl" version of the biosurfactant was the most prevalent in the series. Overall, the complexity of this biosurfactant mixture was highly intriguing, specifically the potential combinations of acetyl groups on the same "base" molecule.

Example 7. Detection of Hyper-Acetylated Mannitol and Arabitol Fatty Acids

Figure 17:
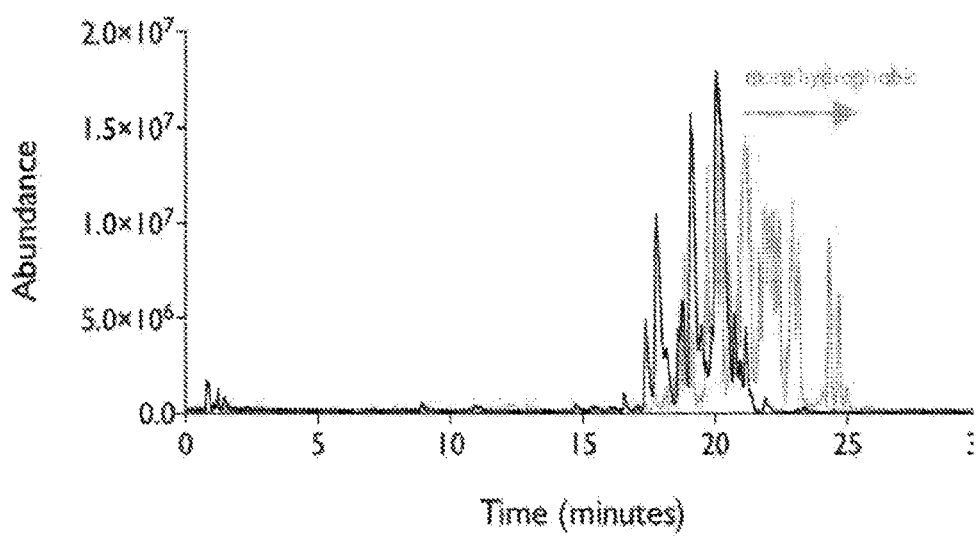
FIGS. 17-18 show that biosurfactants produced by *Rhodosporidium babjevae* are polyol fatty acid esters with a similar composition profile to *R. taiwanensis*.
Figure 18:
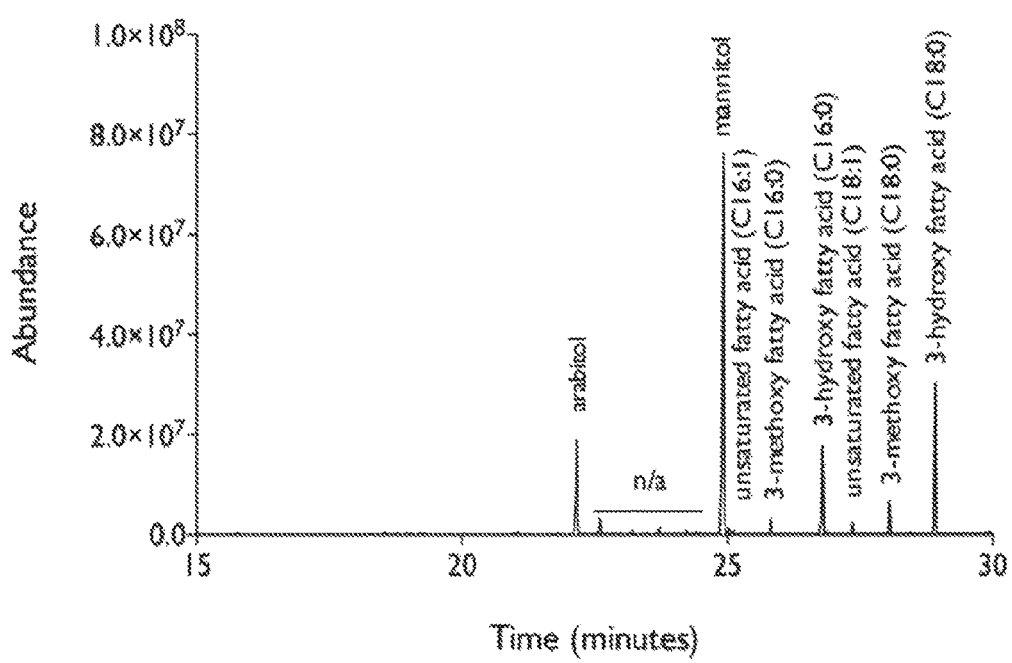

In the process of characterizing the polyol fatty acid esters produced by *R. taiwanensis*, screening of *Rhodotorula* and Rhodosporidium strains for "novel" biosurfactant production was continued, i.e. for compounds that were not sophorolipids similar to those produced by R. bogoriensis, but those that had unique chromatography patterns and masses by LC-MS. Interestingly a unique series of compounds produced by Rhodosporidium babjevae was detected, which had unique masses, and were also more hydrophobic than the polyol fatty acid esters characterized for R. taiwanensis. This increase in hydrophobicity was detected in the chromatographic profile of the purified compounds as they eluted later in the LC run (at a higher organic phase concentration) which is illustrated in FIG. 17; the elution profile of R. taiwanensis is shown in black, while the elution profile for R. babjevae is shown in light gray. Surprisingly, when acid digestion, silylation, and GC-MS analysis was performed on this mixture, the composition of the compounds was the same as R. taiwanensis, although the relative ratio of the individual components was slightly different (FIG. 18). Note that the GC-MS data for both strains is normalized to mannitol (TMS).

Initially, this finding was confounding given the unique masses of the compounds measured by LC-MS, and the noticeable shift in retention time on the C18 column. How could the same base components account for strikingly different masses when compared to the compound mass lists for R. taiwanensis? Even though this strain largely produced biosurfactants with 3 acetyl groups, it was hypothesized that R. babjevae could be producing "hyperacetylated" versions of the same compounds, thereby accounting for the shift in chromatography towards more hydrophobic species, as well as the increase in overall mass of the compounds. Therefore, the theoretical acetylation list was extended for the compounds already detected for R. taiwanensis, and readily detected compounds with >4 acetyl groups. The mass lists for R. babjevae are shown in FIG. 19 and FIG. 20; note that "5 acetyl" mannitol and arabitol fatty acids are the most common glycolipids variants, and the only ones detected for the 3-methoxy C16/C18 and C16/C18 (one double bond) fatty acids.

Example 8. Comparison of Acetylation Profiles of Biosurfactants Produced in R. taiwanensis and R. babjevae In order to better represent the acetylation pattern differences between R. taiwanensis and R. babjevae, the acetylation profiles of the biosurfactants produced in three independent biological replicate cultures for each organism were compared. Spent liquid medium was harvested during peak production of the biosurfactants (prior to biodegradation), and run by LC-MS. The LC-MS data files were then searched in MassHunter using a custom polyol fatty acid database that was constructed from R. taiwanensis and R. babjevae data files. The database represented the molecular formula of the polyol fatty acid previously described along with all of the potential acetylation congeners of the base compounds. The mixture was deconvolved by matching the individual compounds using MassHunter software, and measuring the relative abundance of each compound through total area (after peak integration). The compounds were then parsed into the number of acetyl groups they contained, and the relative areas were added together to create an acetylation distribution of all of the detectable compounds produced by R. taiwanensis versus R. babjevae. The acetylation distribution is shown in FIG. 21A, with a marked Gaussian distribution profile for both strains: R. taiwanensis peaking with 3-acetyl polyol fatty acid species, and R. babjevae peaking with 5-acetyl polyol fatty acid species.

Example 9. Surface Tension of Cultures of R. taiwanensis Versus R. babjevae

To determine if this acetylation profile impacted the surface-active properties of the cultures, the surface tension of the same three biological replicates for R. taiwanensis versus R. babjevae was measured. It should be noted that the total abundance of biosurfactants produced in each of the cultures was relatively equal as determined by LC-MS analysis. Interestingly, there was a significant difference in surface tension between R. taiwanensis (dark gray) and R. babjevae (light gray) culture medium: 35 and 52 mN/m, respectively, with a p-value less than 0.001 (FIG. 21B). These data were consistent with hypo-acetylated species having a lower surface tension (i.e. more hydroxyl groups to interact with water, biosurfactants more hydrophilic) and hyper-acetylated species having a higher surface tension (i.e. the hydroxyl groups were "capped" with the acetyl moiety making the biosurfactants more hydrophobic). These findings support the notion that acetylation of hydroxyl groups on the same polyol fatty acid esters impacted the hydrophilic-lipophilic (aHLB) balance of these compounds.

Example 10. Chemical Synthesis of a 'Base Compound' for a 'Tunable' Surfactant Via Activation Employing the DIC/HOBT System It is expected that 'tunable' surfactants can be synthesized using a synthetic chemical approach by starting with synthesizing a 'base compound' that can be subsequently chemically modified to alter its surfactant properties on the aHLB scale. An exemplary 'base compound' is mannitol 3-hydroxy C18.

Figure 22:
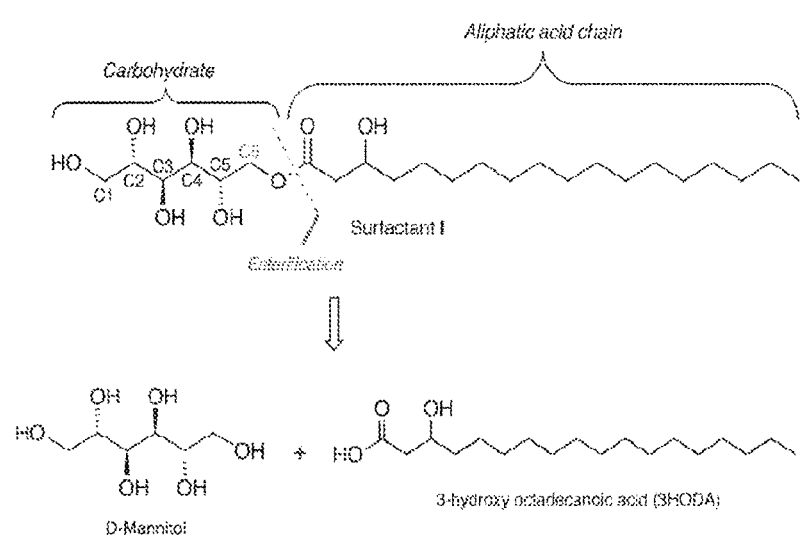
FIG. 22 shows a diagram of the structure of an exemplary model surfactant I and its retrosynthetic analysis. Breakage of the ester bond between the aliphatic chain and the carbohydrate (arrow) results in two products, D-mannitol and 3-hydroxy octadecanoic acid (3HODA).

The surfactants described herein possess the general formula that is represented by surfactant I (FIG. 22). Thus, it can be appreciated that they are composed of two parts: a linear, carbohydrate unit exemplified by D-mannitol and a long, aliphatic chain that has been linked to the terminal hydroxyl group of the mannitol core (i.e. at its C6-position). Retrosynthetic analysis of surfactant I demands the breakage of the ester bond between the aliphatic chain and the carbohydrate. This leads to two products: the first one is mannitol, and the second is the C18-caboxylic acid that may exhibit substitutions along its carbon chain in the form of hydroxyl groups resulting in a chiral building block.

After the retrosynthetic analysis, it can be foreseen that surfactant I can be assembled by initially activating the carboxylic acid via a number of methods, followed by the coupling of this "activated" species with the D-mannitol residue. Two reactivity factors that one must be careful with are 1) the presence of the 3-hydroxyl moiety in the acid, that may interfere with the coupling reaction by forming products (i.e. formation of acid dimers) arising from its intermolecular attack on another activated acid and 2) the reactivity of the hydroxyl groups in D-mannitol. With regards to the second potential issue, it is expected that the primary C6-hydroxyl group in the molecule will possess the most nucleophilic center under neutral conditions while the remaining secondary hydroxyl centers would be too bulky to have any impact in the overall course of the reaction.

Figure 23:
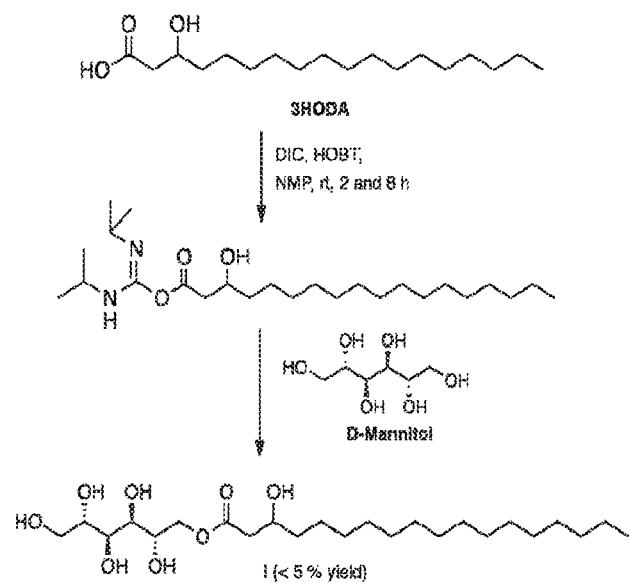
FIG. 23 shows a scheme of exemplary synthesis of surfactant I via activation employing the DIC/HOBT system. 3-hydroxy octadecanoic acid (3HODA) is activated using a mixture of diisopropylcarbodiimide (DIC) and 1-hydroxybenzotriazole (HOBT) in N-methylpyrrolidine (NMP), at room temperature (rt) for 2 hours or 8 hours (top arrow), followed by addition dropwise to a solution of D-mannitol in NMP (bottom arrow).

Armed with these insights, the coupling reaction was initially carried out by activating the 3-hydroxy octadecanoic acid (3HODA) using a mixture of diisopropylcarbodiimide (DIC) and 1-hydroxybenzotriazole (HOBT) in N-methylpyrrolidine (NMP), allow its initial activation for a space of 2 hours (in a second instance activation was allowed to proceed for 8 hours) and then added dropwise to a solution of the D-mannitol in NMP. These conditions resulted in low yields of surfactant I (<5% by LCMS) (FIG. 23).

Figure 24A:
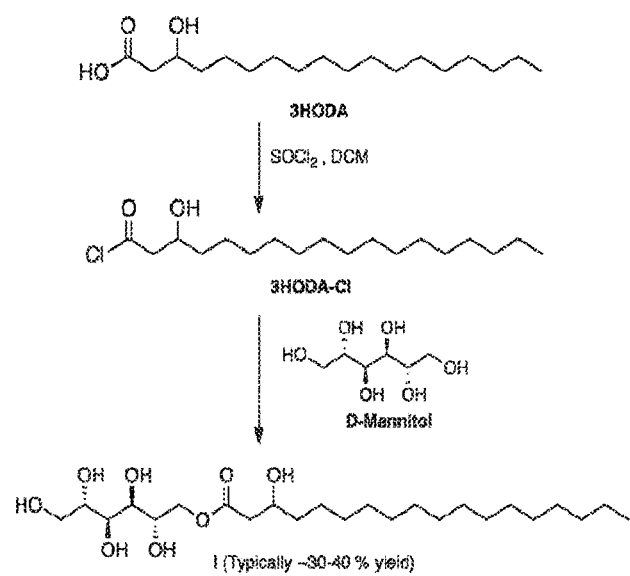
FIG. 24A shows a scheme of exemplary synthesis of surfactant I employing the acyl chloride approach. 3-Hydroxyoctadecanoic acid (3HODA) is taken up in dichloromethane (DCM) and thionyl chloride ($SOCl_2$) is added (top arrow), followed by addition dropwise to a solution of D-mannitol in NMP (bottom arrow).
Figure 24B:
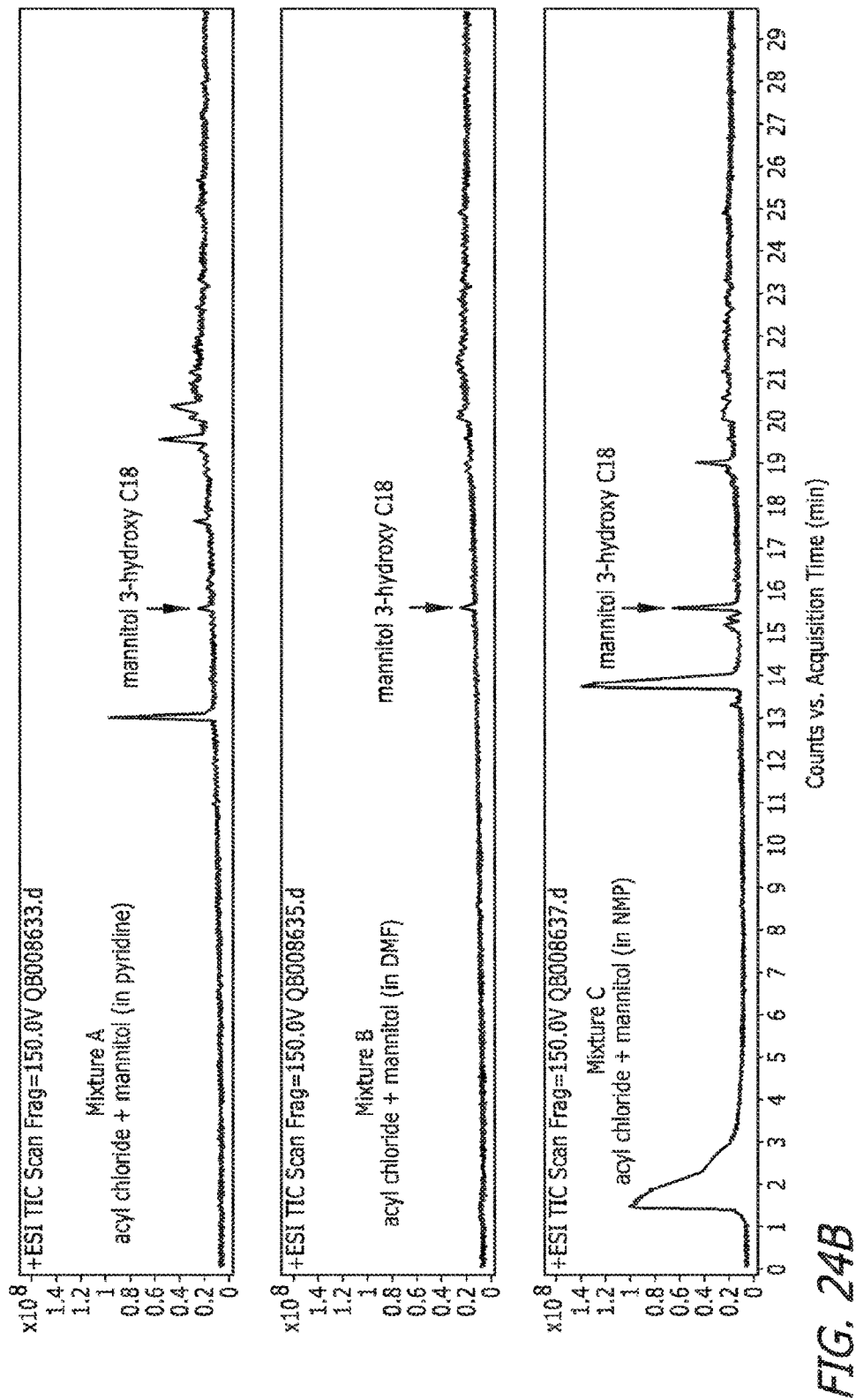
FIG. 24B shows LC traces under three different conditions as displayed in top panel (Mixture A), middle panel (Mixture B) and bottom panel (Mixture C) respectively.

Example 11A. Chemical Synthesis of a 'Base Compound' for a 'Tunable' Surfactant Employing the Acyl Chloride Approach An alternative protocol was also used involving the generation of an intermediate acyl chloride (i.e. 3HODA-Cl in FIG. 24). One of the main reasons for turning to this approach was the feasibility of analyzing the intermediate chloride by various analytical means including NMR (using mainly the $^{13}$C channel). However, one potential obstacle that could be encountered when using this method is the possibility of converting the 3-hydroxyl moiety into a chloride one as thionyl chloride is known to facilitate this type of conversions. Therefore, the number of equivalents of thionyl chloride were maintained below that of the acid, with the overall expectation that the acid functionality would be more reactive than the hydroxyl group under these conditions. Thus, treatment of the acid with thionyl chloride (0.95 equivalents) in dichloromethane (DCM) resulted in the clean, high yielding conversion (~80%) of 3HODA into 3HODA-Cl (FIG. 24A). The acyl chloride is clearly detected by $^{13}$C NMR ($\delta$=170 ppm) and can be distinguished from the carboxylic acid starting material ($\delta$=173 ppm). Furthermore, its formation can be assessed by GC-MS analysis where its presence can be witnessed by the appearance of a sharp signal in the GC chromatograph at 21 min under our GC conditions. Addition of this acyl chloride to a suspension of D-mannitol in pyridine and stirring of the mixture at ambient temperature overnight produced surfactant I in better yields (~30-40% yield). A more detailed description of this method is given below.

3-Hydroxyoctadecanoic acid (30 mg, 0.1 mmol) was taken up in dichloromethane (DCM, 1 mL) in a 4 mL scintillation vial equipped with a stir bar. To this suspension, thionyl chloride (SOCl$_2$, 7.4 µL, 0.095 mmol, 0.95 equivalents) was added in one single portion and the vial equipped with an adapter for its attachment to a condenser (T=7° C.) and the mixture refluxed at 70° C. for 3 hours. The time of 3 hours was determined after several rounds of activation into the acyl chloride were done and analyzed after 1, 3, 5 and 24 hours. It was found that 3 hours seemed to be the time where most of the acyl chloride formed and its hydrolysis was minimal. Thus, the heating was stopped and the thionyl chloride (if any) along with the DCM were removed in vacuo at 70° C. to give a pale yellow oil (39 mg). The oil was dissolved in DCM (0.5 mL) and added dropwise over 2 minutes to a suspension, in a 20 mL scintillation vial, of D-mannitol (27 mg, 0.15 mmol, 1.5 equivalents to acid) in pyridine (3 mL). Upon addition of all of the acyl chloride, smoke was observed in the vial. The resulting mixture was stirred at room temperature overnight. A note about the mannitol is that it needs to be heated gently with a heat gun to force it as much as possible in the pyridine. It was observed that if the mannitol is not fully dissolved (for example in DCM), the reaction does not work. After the overnight stirring, the suspension (white precipitate) is filtered through a disk and evaporated under high vacuum at 40° C. to give a white solid. Analysis of the white solid by LCMS shows that the product has been formed (~30-40% yield, based on 3 experimental runs).

It is expected that other bio-surfactants bearing similar features to surfactant I can be assembled in this manner. In addition to mannitol 3-hydroxy C18, it is expected that other base compounds including but not limited to arabitol esters of 3-hydroxy C18, and mannitol and arabitol esters of 3-methoxy fatty acids, and fatty acids with a single double bond, and with other carbon chain lengths such as C16 can be prepared following similar methods as described above.

Example 11B. Modified Chemical Synthesis of a 'Base Compound' for a 'Tunable' Surfactant Employing the Acyl Chloride Approach Acyl chloride (3HODA-Cl) was generated by reacting the 3-hydroxy-octadecanoic acid (53 mg, 0.18 mmol) with thionyl chloride (22 µL) in methylene chloride (DCM, 1 mL) inside a 4-mL glass vial equipped with a small stir bar. The mixture was heated to reflux for 2 hours. After the DCM was all evaporated off, the mixture was taken up in DCM again (900 µL). The generated acyl chloride suspension was equally partitioned (3×300 mL) volumes and added separately to a suspension of mannitol (40 mg) in pyridine (200 µL) (Mixture A), in DMF (200 µL) (Mixture B) and in NMP (200 µL) (Mixture C) in 3 separate 4-mL glass vials equipped with a stir bar. The resulting mixtures were stirred at ambient temperature overnight.

The following day, the mixtures were analyzed by LC-MS. The LC traces (FIG. 24B) show that the DMF reaction mixture (mixture B) produces the most pure product although in low concentration. The protocol as described herein depicts an overall synthetic procedure with the only difference among the thress processes associated with solvents employed pyridine in Mixture A, DMF in Mixture B and NMP in Mixture C which corresponds to top, middle and bottom panels of FIG. 24B.

Example 12. Biosynthetic Production of a 'Base Compound' for a 'Tunable' Surfactant It is expected that a biodegradable surfactant such as surfactant I can be produced biosynthetically as an alternative to production by synthetic chemistry. For example, this approach can involve generating a yeast mutant wherein the acetyltransferase responsible for acetylating the base surfactant, such as mannitol 3-hydroxy C18, is deleted, so the yeast produces only the non-acetylated biosurfactants. The genome of *R. taiwanensis* has been sequenced and therefore candidate *R. taiwanensis* acetyltransferases can be identified by comparison of homology of DNA, mRNA, or protein sequences with those of other known acetyltransferases and transacetylases in databases such as NCBI and others known to persons skilled in the art. Analysis of homology can be performed using available sequence analysis algorithm programs including but not limited to CLUSTAL, ALIGN, GAP, BESTFIT, BLAST, FASTA, and TFASTA among others known to a skilled person. Genes with sequence identity greater than 80% can be considered homologous. Homology of yeast genes can be analyzed with respect to known acetyltransferase enzymes. Budding yeast encode multiple histone acetyltransferases (HATs)/lysine acetyltransferases (KATs) which use acetyl-CoA as a substrate to transfer acetyl groups to histones and non-histone proteins [10, 11], or transacetylases similar to the acetyltransferase from *Candida bombicola*, which mediates the acetylation of de novo synthesized sophorolipid biosurfactants [12]. Interestingly, deletion of this enzyme gene results in the production of only unacetylated sophorolipids, which impacts the physical-chemical properties of these compounds [12] (note: sophorolipids are acetylated at two potential positions, versus six for mannitol 3-hydroxy C18).

Deletion of candidate acetyltransferase genes and production of unacetylated surfactants from *R. taiwanensis* can be performed following the methods described in Saerens et al. (2011) [12], as follows: A *R. taiwanensis* acetyltransferase enzyme-encoding gene is identified by homology analysis as described above. Using primers designed based on *R. taiwanensis* acetyltransferase gene sequence information (using PrimerDesign software), the complete acetyltransferase enzyme gene (AT) is cloned into pGEM-T plasmid (Promega) containing a hygromycin and ampicillin resistance genes to provide pGATtot plasmid. *E. coli* DH5alpha are used for plasmid maintenance, grown in Luria Bertani broth and selected in Luria Bertani media, each containing appropriate antibiotic for selection. A suitable deletion construct is created from this plasmid by mutation of the AT gene. A frameshift mutation is induced into the AT gene by digesting plasmid pGATtot overnight with a single cutter restriction endonuclease (New England Biolabs), based on sequence analysis, according to ref: Sambrook and Russell, 2001, Molecular Cloning, A Laboratory Manual, resulting in linearization of the plasmid. The linearized plasmid is purified by QIAQuick purification kit (Qiagen) and subjected to mung bean exonuclease digestion (New England Biolabs) to remove the 5' overhangs. Following purification, the plasmid is self-circularized by incubation with T4 DNA ligase and buffer (Fermentas GmBH). The resulting plasmid pGATtot mutAT containing a mutated AT gene is used for transformation of *E. coli* DH5alpha according to Sambrook and Russell, 2001. Plasmids are prepared (Mini-Prep, Qiagen) and deletion of the single-cutter enzyme restriction site are checked by double digestion with the single-cutter enzyme and one other enzyme with a recognition site within the gene sequence (based on sequence analysis) and agarose gel electrophoresis analysis. A linear knock-out cassette is created from plasmid pGATtot mutAT using primers designed based on sequence analysis to amplify a fragment containing the mutated frameshifted AT gene and the antibiotic marker and the PCR fragment is purified (QIAQuick, Qiagen) and the purified amplicon is used for transformation of *R. taiwanensis* by electroporation. For that, cultures of *R. taiwanensis* are grown in appropriate buffer as described in Examples above, and following electroporation methods described by Saerens et al. (2011). Briefly, cells are harvested by centrifugation, washed, and resuspended in sorbitol (1M), centrifuged, and resuspended in lithium acetate (0.1M) in presence of 2.5 mM DTT and left to rest at room temperature for 10-15 minutes. Cells are then harvested and washed before resuspending in 1M sorbitol. From this suspension, 50 uL is carried over into a sterile microcentrifuge tube, approximately 700 ng of the linearized purified knock-out cassette is added and the mixture incubated on ice for 2 minutes before transfer to a 2 mm electroporation cuvette. A pulse of 1.5 kV is given during 5 ms and 1 mL of ice cold and sterile growth medium is added. The cells are then incubated for 1 h at 30 degrees C. and then harvested by centrifugation. Cells are then resuspended in sorbitol (1M) and aliquots grown on selective medium containing appropriate growth buffer containing hygromycin antibiotic (Sigma-Aldrich) for selection of positive yeast transformants. Plates are incubated at 30 degrees C. until transformant colonies appear. Transformants are selected and analyzed for presence of the deletion cassette by PCR and gel electrophoresis analysis, and DNA sequencing, using primers designed to bind to sequences internal to and/or flanking the inserted deletion cassette and amplify a portion of the polynucleotide inserted into the genome. Positive *R. taiwanensis* colonies are then grown in medium and the resulting unacetylated surfactants produced are purified by solid-phase methods as described herein and their composition confirmed using LC-MS methods as described herein. It is expected that an unacetylated surfactant is produced in an acetyltransferase deletion mutant of *R. taiwanensis* using this method.

Example 13. Synthetic Chemistry Production of 'Tunable' Surfactant with Variable Acetylation, Sulfation, and/or Phosphorylation The next step on the development of other members of this new class of surfactants involves the acetylation of the hydroxyl groups present in the mannitol as well as in the aliphatic chain. It is expected that one can tune the overall hydrophobicity and hydrophilicity of the surfactant by controlling the degree of acetylation, sulfation, and/or phosphorylation on the molecule.

Acetylation can be carried out by treating surfactant I with acetic anhydride in pyridine or a combination of DCM with a base such as triethylamine to scavenge the generated acid (i.e. acetic acid). Of course, no controlled form of acetylation exists that can discriminate where the acetyl group can go in surfactant I. *A priori*, one would expect that the primary hydroxyl group (label C1 in I in FIG. 22) should be the first place where acetylation would occur under neutral conditions and this can certainly be the case (FIG. 25). However, the specific acetylation of for example C3 over C2 is an endeavor that brings the necessity of protective group manipulations resulting in longer synthetic schemes. Thus, a separate approach to the attainment of these higher order, acetylated versions of surfactant I might entail the treatment of I with specific equivalents of acetic anhydride to obtain a statistical mixture of products that can then be separated by semi-preparative LC-MS means. Thus, addition of acetyl groups to the surfactant would produce analogs with a more lipophilic profile than the parent compound (FIG. 25) filling in the lower end of the spectrum of the hydrophobicity/lipophilicity spectrum chart. It is expected that filling in the part of the spectrum that includes more hydrophobic molecules can also be achieved. For example, a way that the hydrophilicity of surfactant I can be increased is by introducing groups like a sulfate or phosphate that produce anionic centers in the molecule and thus increase its overall hydrophilicity (FIG. 25). For example, surfactant I can be treated with chlorosulfonic acid ($ClSO_3H$) or phosphoroyl trichloride ($POCl_3$) to provide the sulfated and the phosphorylated analogs respectively. The degree of sulfation/phosphorylation in the surfactant will determine the overall hydrophilicity of the surfactant.

Furthermore, it is expected that a 'base compound' such as surfactant I can be tuned to have a shifted aHLB by introducing combinations of groups of acetylation, sulfation, and phosphorylation, for example at any of C1-C6. This is expected to be achieved by employing combinations of successive chemical modifications as described above.

Example 14. Biosynthetic Production of 'Tunable' Surfactant with Variable Acetylation As an alternative to chemical acetylation of the biodegradable surfactant I, it is expected that acetylation of the base molecule can be achieved by employing an enzymatic process through the use of cloned, expressed acetyltransferases enzymes.

For example, following identification of the acetyltransferase(s) responsible for catalyzing the production of the acetylated polyol fatty acid esters in *Rhodotorula* or *Rhodosporidium* strains described herein as described in Example 12 above, the acetyltransferase enzyme(s) are cloned into an expression vector and expressed in a host cell, following methods known to persons skilled in the art, such as those described by A. Amid and N. Hassan, Recombinant Enzyme: Cloning and Expression. In Recombinant Enzymes—From Basic Science to Commercialization, A. Amid (ed.), 2015. Subsequently, the cloned, expressed acetyltransferase(s) can be incorporated into a bioreactor to catalyze production of acetylated biosurfactant, as follows.

Total RNA is isolated from *Rhodotorula taiwanensis* (RNeasy kit, Qiagen) and a cDNA library is produced by reverse transcription (High-Capacity cDNA reverse transcription kit, Applied Biosystems).

Yeast cell-based expression of recombinant *R. taiwanensis* acetyltransferase enzyme can be performed using the *K. lactis* protein expression kit, *K. lactis* competent cells, and pKLAC2 expression vector (New England Biolabs, NEB), according to the manufacturer's directions, as follows. PCR-based amplification of the acetyltransferase cDNA is performed using appropriately designed primer pairs (e.g. using PrimerDesign or other programs known to those skilled in the art) based on sequence information from the identified *R. taiwanensis* acetyltransferase gene. An encoded tag can be incorporated into the primer design (e.g. encoding a HA-tag or His-tag, fused to the N- or C-terminus of the enzyme) to facilitate immobilization of the cloned, expressed acetyltransferanse enzyme(s) in a bioreactor. Further, the primers are designed to encode appropriate restriction endonuclease recognition sites at the 5' (e.g. XhoI) and 3' (e.g. NotI) ends of the amplicon to facilitate cloning into the pKLAC2 vector. To achieve protein secretion, the acetyltransferase gene is cloned downstream of the *K. lactis* α-mating factor secretion domain sequence encoded in the plasmid. PCR amplification of the acetyltransferase cDNA is followed by agarose gel purification of the amplicon (Qiagen kit). The amplicon and the pKLAC2 vector are digested with appropriate restriction enzymes (e.g. NotI and XhoI) followed by ligation (using T4 DNA ligase) of the purified amplicon into the multiple cloning site of the vector. Competent DH5alpha *E. coli* are transformed (e.g., heat shock method) with the ligation product. Transformed bacterial cultures are grown in LB broth and DNA is prepared (Mini-prep, Qiagen). Identification of positive transformants is performed using analytical DNA restriction digests and gel electrophoresis and/or DNA sequencing. pKLAC2 containing the cloned acetyltransferase gene must be linearized to allow it to insert into the *K. lactis* genome at the LAC4 locus. This is accomplished by digesting the construct with either SacII (supplied with the NEB kit) or BstXI to generate an "expression cassette" consisting of >6.2 kb of DNA containing $P_{LAC4\text{-}PBI}$, the cloned gene and the amdS cassette, and a 2.8 kb fragment containing the remaining pKLAC2 vector DNA. The cloned gene must be free of SacII sites (or BstXI sites if digesting with BstXI) to allow for generation of the proper expression fragment. Introduction of the linearized expression cassette into *K. lactis* cells is achieved by chemical transformation using the *K. lactis* GG799 Competent Cells and NEB Yeast Transformation Reagent supplied with the kit, following the manufacturer's directions (NEB). Transformants in which the expression cassette has correctly integrated into the *K. lactis* genome are identified by PCR using supplied Integration Primers 1 and 2 (NEB) to amplify a 2.4 kb product identifiable upon gel electrophoresis analysis. Positive *K. lactis* transformants are grown in culture and the expressed recombinant tagged acetyltransferase enzyme is isolated from growth media following the manufacturer's directions (NEB).

The expressed recombinant acetyltransferase enzyme is then incorporated into an enzymatic bioreactor, such as an immobilized enzyme bioreactor via immobilization of the enzyme using a tag such as a His-tag bound to a solid phase. This can be accomplished using commercially available kits such as EziG (EnginZyme), following the manufacturer's directions. Briefly, controlled porosity particles comprising chelated $Fe^{3+}$ iron facilitate binding of His-tagged proteins, such as the recombinantly expressed acetyltransferase enzyme. The immobilized enzyme, biodegradable surfactant and other necessary reagents (e.g. buffers containing acetyl-CoA donor for acetylation) are added to the bioreactor apparatus and incubated for a sufficient time and under conditions to permit enzymatic acetylation of the biosurfactant. Following incubation in the bioreactor and completion of enzymatic phosphorylation processes, acetylated 'tuned' biosurfactant is expected to be produced, with a modified aHLB. These acetylated biosurfactants are then isolated from the bioreactor and purified, for example, using solid-phase extraction methods outlined above. Confirmation of the acetylation of the biosurfactant is performed by LC-MS or other methods described herein.

In summary, provided herein are biodegradable surfactants, and related compositions, methods and systems are described herein. In particular, the biodegradable surfactants described herein comprise an amphiphilic heteroatom containing hydrocarbon comprising an hydrophilic head portion optionally comprising at least one counterion (Z) and an hydrophobic tail portion. The biodegradable surfactant described herein has an aHLB value in accordance with equation (1): $aHLB=20*G_h/(G_h-G_t)$ (1) wherein $G_h$ is the Group Number of the head portion of the biodegradable surfactant, and $G_t$ is the Group Number of the tail portion of the biodegradable surfactant. Biodegradable surfactant in the sense of the disclosure can be tuned by selectively modifying at least one tuning moiety of the biodegradable surfactants to result in tuned biodegradable surfactants having an increase or decrease in their adjusted hydrophilic-lipophilic balance (aHLB).

Example 15. Determination of HLB Value and Group Numbers

As further shown in FIG. 25, Surfactant I of Formula (III) can also be derivatized to a monophophorylated-Surfactant (I) and further to a perphosphorylated-Surfactant (I) to raise the aHLB.

It is noted that phosphoryl groups, along with a corresponding counterion, are not included in Table 1 or previously calculated by Davies et al (Davies J T (1957), supra) [4]. Therefore, a person of skill could make an analytical measurement of coalescence rate as described by Davies et al to determine the HLB value (using the phosphorylated surfactant of interest).

This HLB value could be plugged into equation (2)

$$HLB=\Sigma(\text{hydrophilic group numbers})+\Sigma(\text{lipophilic group numbers})+7 \quad (2)$$

Once the HLB value is measured, and plugged into equation (2), then the equation can be solved for the hydrophilic group number of a phosphoryl group with it's corresponding counterion. This process can be performed for all unknown hydrophilic group numbers.

The Group Number so calculated can be used to determine aHLB value according to procedures such as the ones exemplified in Example 16.

Example 16. Calculation of aHLB Value for Exemplary Amphiphilic Heteroatom Containing Hydrocarbon Based on Group Number of Moieties of the Hydrocarbon An engineered *Rhodotorula* strain, deleted for its sugar acetyltransferase, is expected to be able to produce in bulk the Surfactant I represented as Formula (III) and also shown in FIG. 25. This compound can be collected and purified in bulk (kilogram amounts), and would establish the core compound utilized for later "tunability" studies.

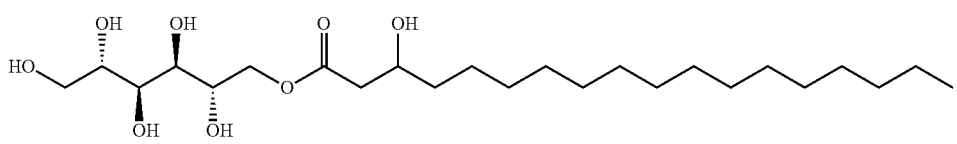

Surfactant I

Accordingly an aHLB value of Surfactant I of Formula (III) can be calculated based on the Group Number of Table 1.

The head portion of Surfactant I of Formula (III) has a Group Number $G_h$ of 10 (6*1.9+2.4-8*0.475) resulting from 6 hydroxyl groups (1.9), 8 CH/CH2/CH3 groups (-0.475), and one ester group (2.4).

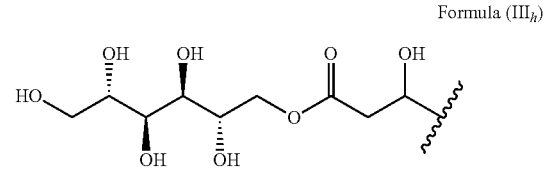 [SMILES: *C(O)CC(=O)OC[C@H](O)[C@H](O)[C@@H](O)[C@@H](O)CO]

Formula (III$_h$)

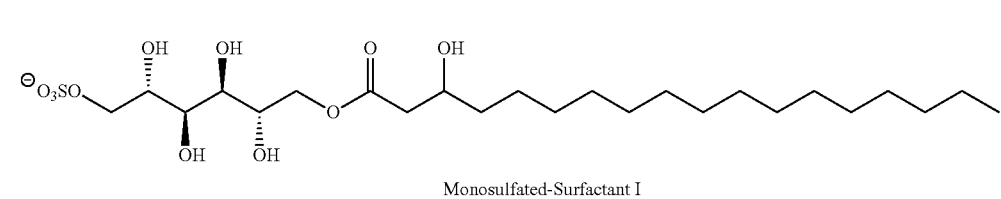

Formula (III$_t$)

The tail portion for Surfactant I as represented by Formula (III$_t$) has a Group Number $G_t$ of -7.125 (-0.475*15) which results from 15 methylene group or methyl groups each having a group value of -0.475.

Therefore, according to equation (1) herein described, the aHLB for Surfactant I is 11.68 (20*10/(10+7.125)).

Formula (III$_h$-Ac)

Figure 21:
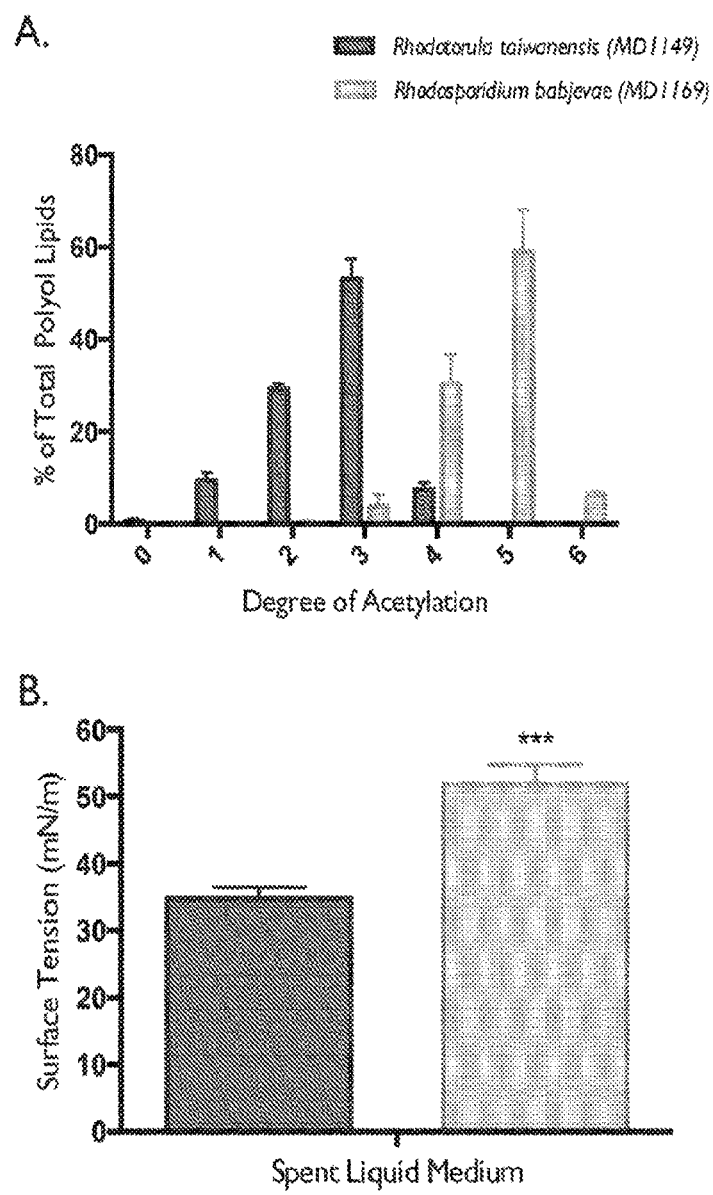
FIG. 21 shows that exemplary biosurfactants produced by *R. taiwanensis* and *R. babjevae* have distinct acetylation profiles that impact their surface-active properties. Spent liquid medium was harvested during peak production of biosurfactants in three replicate experiments (for each organism), and analyzed by LC-MS. The LC-MS data files were then mined in MassHunter software using a custom polyol fatty acid database. The relative abundance of each compound was measured through total area (after peak integration), and the compounds were then parsed into the number of acetyl groups they contained. The individual areas for each acetyl group species were then added together to create an acetylation profile of all of the detectable compounds produced by *R. taiwanensis* (dark gray) versus *R. babjevae* (light gray) (FIG. 21A). The surface tension of the spent liquid medium for each of the three biological replicates was also measured, averaged together, and compared between *R. taiwanensis* (dark gray) versus *R. babjevae* (light gray) (FIG. 21B). Note that the total abundance of biosurfactants produced in each of the cultures was relatively equal. A p-value less than 0.001 is indicated by the three asterisks.

Although the specific Group Numbers for Surfactant I with one acetyl modification represented by Formula (III$_h$—Ac) has not been experimentally measured and the Group Numbers of Table 1 cannot be used without experimental verification in view of the mention of a chemical environment for hydroxyl and ester groups in the table, it is expected that once measured the Group Number of the hydroxyl groups would be higher than the acetyl group in view of the results indicated in FIGS. 17 and 21 and related portions of the specification.

Example 17. Exemplary Tuning of Tunable Moiety of an Amphiphilic Heteroatom Containing Hydrocarbon As further shown in FIG. 25, the aHLB of Surfactant I of Formula (III) can be raised via derivatization to a monosulfated-Surfactant (I) of Formula (III-1S) and further to a persulfated-Surfactant of Formula (III-6S) using sodium as a counterion, thus tuning the compound to a higher aHLB of Surfactant (I).

Formula (III-1S)

Monosulfated-Surfactant I

A also shown in FIG. 25, once this compound is collected and purified from the growth medium, it can then be tuned to a specific aHLB value that is relevant to the industrial process needed. For example, this bulk compound could be systematically acetylated using simple chemistry to lower the aHLB based on the indication of the data illustrated, for example, in FIGS. 17 and 21 and related portions of the specification.

After tuning to monosulfated-Surfactant I of Formula (III-1S), the replacement of one tuning moieties (hydroxyl) with sodium sulfate, change to resulting aHLB to 16.69.

Further introduction of sulfate groups to a total of six of them for persulfated-Surfactant I of Formula (III-6S) further increase the resulting aHLB to 19.18, due to the dramatic increase of the hydrophilicity from that of sulfate (38.7) from hydroxyl (1.9).

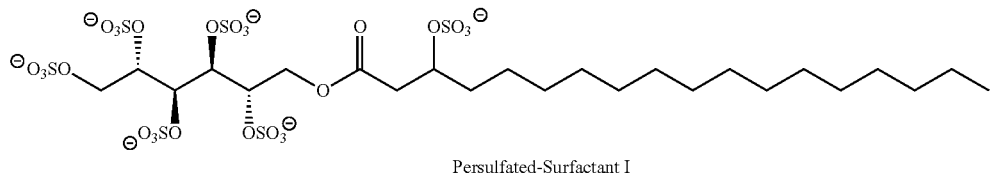

Persulfated-Surfactant I

As the tail portion of the Formula (III), Formula (III-1S), Formula (III-6S) are the same, their corresponding Group Number Gt are also the same, being −7.125. Therefore, the tuning of the aHLB are a result of modification of tunable moiety OH to sodium sulfate group.

As illustrated by the replacement of one or six hydroxyl of Surfactant I, the aHLB changes from 11.69 to 16.69 and 19.18 for biodegradable surfactants of Formula (III), Formula (III-1S) and Formula (III-6S) respectively.

Example 18. Physical Properties of Exemplary Biodegradable Surfactants

In biosurfactant herein described, the nature of the counterion is expected to have, at least to some extent, a direct effect on the overall physical properties of the bulk material prior to its partial solubilization in a solution including an aqueous medium or a mixture of water and at least one organic solvent. Such effect is in particular expected upon modification of biodegradable surfactant with polar groups (such as the phosphate or sulfate groups) placed onto the hydroxyl and amino groups on a tunable biodegradable surfactant including carbohydrates. Thus for the preparation of a surfactant with a phosphate group, the counterion in this case will come from the base (KOH or NaOH) employed to carry out the final unmasking of the phosphate group. Based on the group table discussion above, we would expect differences between the K and/or Na final preparations.

Accordingly, with regards to the physical properties of the initially prepared surfactant, the differences between counterions of similar properties such as the Group I metal ions (e.g. $Na^+$, $K^+$, $Cs^+$) are expected to be relatively small as these represent a small perturbation of the overall surfactant. However when these cationic species with those involving organic amine-based species (e.g. triethylammonium-, imidazolium or pyridinium-based salts arising from the use of triethylamine, imidazole and pyridine respectively), the properties of the surfactant salt relative to the Group I metal-based salt preparation will differ to some extent for example in their degree of hygroscopicity or physical appearance (e.g. crystalline solid vs. amorphous solid, or liquid). By the same token, the nature of the counterion in the cases involving the amino-based carbohydrate unit, a person of skill in the art would understand the differences to be notable when dealing with very different anionic species (e.g. $BF_4^-$ vs. $SO_4^{2-}$) as counterions. This can be worked out through direct measurements of coalescence with different counterions described herein.

In biodegradable surfactants herein describe, upon solubilization of the biosurfactant, the nature of the counterion utilized for the preparation of the biosurfactant is expected to affect the degree of hydrophobicity and hydrophilicity of the finalized surfactant in a composition as will be understood by a skilled person. As described herein, the group number includes the presence of the counterion in the aqueous solution/coalescence measurement. Therefore, this could be determined following the method described herein.

Regarding the physical properties imparted by the counterion in solution and how the counterionic species will affect the overall solubility behavior of the surfactant in aqueous solutions, Table 1 illustrates the subtle difference in lipophilicity when a carboxylate group is associated with a $K^+$ or $Na^+$ counterion, giving rise to Group Number values of 21.1 and 19.1 respectively and having a difference of 2.0 in the value of Group Numbers.

Thus, a person of skill in the art would know that the value difference between other more notably different cationic species will result in greater difference in the Group Number values, for example, greater than the 2 point value noted above for $Na^+$ and $K^+$ associated species. A person of skill in the art would understand that the more different in the nature of cationic species, the more different would be the values of the corresponding Group Numbers.

Example 19. Exemplary Biologically Produced Amphiphilic Heteroatom Containing Hydrocarbon and Related Biosynthetic Pathway An exemplary biologically produced amphiphilic heteroatom containing hydrocarbon is provided by polyol esters of fatty acids (PEFA). The biosynthetic pathways for production of polyol esters of fatty acids (PEFA) is currently being elucidated, and is not fully characterized.

As proposed by Garay et al 2017, this biosynthetic pathway likely includes fatty acid synthase enzymes, an enzyme responsible for hydroxylation on position 3 of the fatty acyl moiety, enzymes responsible for D-mannitol formation, and transporter proteins, among others. Prophetically, these enzymes (once identified) could be expressed together in *Saccharomyces cerevisiae* (yeast) using the pGREG series of shuttle vectors as described by Fossati et al 2015 for recombinant morphinan alkaloid production. [32] Recombinant protein expression of biosynthetic enzymes in *Escherichia coli* is also possible given the large availability of expression vectors with variable replicons, promoters, selection markers, and affinity tags, and *E. coli* strains (outlined in Rosano et al). [33]

Expression of biosynthetic pathways using a baculovirus-insect cell is also of interest given the success of these systems in producing recombinant mammalian glycoproteins with authentic oligosaccharide side chains (Jarvis, 2003). [34] Biosurfactant enzymes would be cloned into baculovirus vectors and used to create transgenic insect cell lines that express biosurfactant biosynthetic enzymes, which in turn could produce amphiphilic heteroatoms containing hydrocarbons. Mammalian protein production of the enzymes responsible for biosurfactant production could also occur in mammalian cell lines (e.g. CHO, HEK 293, PER.C6, and CAP/CAP-T), with these enzymes being mixed together in vitro to produce PEFA compounds of interest. Therefore, small molecule (chemical) biosurfactant can be produced recombinantly, i.e. outside it's native microbial strain.

Example 20. Causing Expression of Amphiphilic Heteroatom Containing Hydrocarbon The biosurfactant compounds are naturally secreted into the growth medium while the yeast replicate. Rhodotorula MD1149 was grown in yeast mold broth (YM, Difco #271120) overnight at 25° C. and diluted to 0.05 $OD_{600}$/mL in Hommel's minimal salts (HMS, per liter—3 g $(NH_4)_2$ $SO_4$, 0.5 g NaCl, 0.7 g $MgSO_4$, 0.4 g $Ca(NO_3)_2$, 0.4 g $K_2HPO_4$, 2.5 g $KH_2PO_4$) supplemented with 0.6 g/L yeast extract (Difco #210929) and 50 g/L glucose. Garay et al. 2017 also reported that Medium A, a medium with high C:N ratio (68:1) is effective in inducing lipid (polyol esters of fatty acid) accumulation in oleaginous yeasts. [35]

Isolation of the biosurfactant produced by Rhodotula can be provided using the techniques describe in example 3B for bulk isolation of the biosurfactants from solution.

Example 21. Engineering of a Cell to Biologically Produce a Biodegradable Surfactant In order to biologically produce the biodegradable surfactant from *Rhodotorula* to be used in tunability studies (shown below and designated Surfactant I in FIG. 25), a person of skill can follow the method provided hereafter. This method would be used to create a CRISPR genetic system, or traditional homologous recombination system, in *Rhodotorula* strains. This method and system can be used to delete one or more genes from *Rhodotorula* strains as will be understood by a skilled person.

Accordingly, the yeast genome could be engineered to produce the Surfactant I compound in large quantities and purified. This compound could then be further modified through chemical means to adjust the aHLB for industrial processes.

Function: Orotidine-5'-phosphate decarboxylase (OD-Case)

Protein Sequence (SEQ ID NO: 4):
"MPSVTKRTYADRAAKHPIPVAQQLLAVCDRKRTNLCVSVDVTSKASLLR

IADAAGPYCCCIKTHIDIVEDFDRDLVEQLQALAEKHDFLIWEDRKFADI

GTREGDLMTEEKFGLTRRLVYSSGIYKIASWAHITNAHLVPGEGILTGLA

SVGEPLGRGLLLLAEMSAKGNLATGEYTAKNVEAARRYPNFVMGFVAMKR

VDEREETAGGVTAGEGPDFVIMTPGIGLDSKGDGMGQQYRTPDEVIRESG

CDIIIVGRGIYGGGDGNPSEEIVKQCQRYQAAGWESYERRLKE".

In The URA3 gene of *Rhodoturula* MD1149 (or similar Rhodotorula strain) can be mutated through natural selection when grown in the presence of 5-FOA (5-Fluoroorotic acid). If there is a functioning URA3 gene, the ODCase enzyme converts 5-FOA into the toxic compound 5-fluorouracil (a suicide inhibitor) thereby causing cell death.

Therefore, Rhodotorula that grows in the presence of 5-FOA has lost the functional activity of the ODCase enzyme (it has a mutated URA3 gene). This approach is "non-targeted", and selects for ura3⁻ mutants that naturally arise during yeast cell division.

A person of skill in the art could also follow a "targeted" method to mutate or delete the URA3 gene. These targeted methods would be a variation of those described by Zhang et al 2016 in Appl Microbiol Biotechnol and Zhang et al 2016 Biotechnology and Bioengineering. Briefly, 1 kb of sequence, upstream and downstream of URA3, would be PCR amplified from the *Rhodotorula*. [13] [14]

The nourseothricin resistance cassette would also be PCR amplified; nourseothricin is a compound that blocks protein biosynthesis in various yeast species and fungi, and resistance to nourseothricin is conferred by the natI gene originally isolated from *S. noursei*. Subsequently, the three DNA

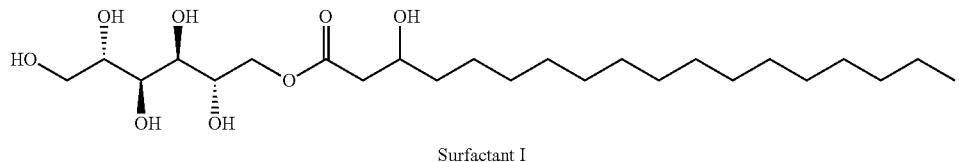 [SMILES: CCCCCCCCCCCCCCCC(O)CC(=O)OC[C@H](O)[C@H](O)[C@@H](O)[C@@H](O)CO]

Surfactant I

The first step in creating a CRISPR genetic system for *Rhodotorula/Rhodosporidium* strains is the generation of a haploid strain that has a mutated URA3 gene (known herein as "haploid ura3⁻"). It is noted that a haploid strain is preferable for subsequent genetic manipulations, although a diploid strain with mutated copies of both URA3 genes is possible. A person skilled in the art would know that URA3 is used as a selectable marker in a variety of yeast systems. URA3 encodes for the ODCase enzyme; loss of ODCase activity leads to a lack of cell growth unless uracil or uridine is added to the media. The presence of the URA3 gene (e.g. on a CRISPR plasmid) restores ODCase activity, facilitating growth on media not supplemented with uracil or uridine, thereby selecting for yeast carrying a plasmid encoding the URA3 gene.

The sequence of URA3 gene in Rhodotorula is as follows: MD1149 genome
URA3 ortholog in MD1149:
Gene: BMF94_5250 fragments would be ligated to pGI2 as described by Zhang et al. [13] [14] This plasmid would be used in a targeted approach to replace the URA3 gene with a selectable marker resistance cassette in the yeast genome.

A person of skill in the art would know that *Pucciniomycotina* red yeasts, such as *Rhodotorula*, are recalcitrant to transformation with plasmids as described by Abbott et al 2013 Appl Microbiol Biotechnol, [36] and would use the *Agrobacterium tumefaciens*-mediated transformation method to introduce the pGI2-URA3 knockout plasmid as described by Liu et al. 2013 [37] and Zhang et al. 2016. [13] [14] Briefly, the pGI2-derived binary plasmids would first be electroporated into *Agrobacterium tumefaciens*. *A. tumefaciens* would be subcultured in 50 mL from an overnight seed culture until OD reached around 0.5. The culture would be first washed with ice cold 1 mM 4-(2-hydroxyethyl)-1-piperazineethanesulfonic acid (HEPES), pH 7.0, and then washed with 1 mM HEPES, pH 7.0, 10% glycerol, before finally being resuspended in 0.5 mL of ice cold 1 mM HEPES, pH 7.0, 10% glycerol. 1 uL of URA3 knock out plasmid DNA (50 ng-1 ug) would then be electroporated using a Gene Pulser Xcell (Bio-Rad) with 2.5 kV electrical pulse (field strength of 12.5 kV/cm) and recovered in 1 mL MG/L medium at 30 C for 2 h and then plated onto kanamycin LB plates. Colonies containing the binary plasmid would be visible after 2 days growth at 30 C.

As a variation of Zhang et al, *A. tumefaciens* strains harboring the binary plasmid would then be cultured in 1 mL MG/L medium with kanamycin until the OD reached approximately 1.0. [13] [14] The cells would then pelleted and resuspended in 1 mL induction medium for 7 h in 30 C. *Rhodotorula* MD1149 would then be cultured in YPD medium to mid-exponential phase, and the cells diluted to OD approximately 0.5 and mixed with induced *A. tumefaciens* cells in equal volume to a total volume of 1 mL. The mixture would then be vacuum filtered using a 0.45 micron filter membrane. The filter would then be placed on an induction medium plate, and incubated at room temperature for 2 days. The cells on the membrane would then resuspended with YPD medium and plated onto a YPD plate supplemented with nourseothricin and cefotaxime, where the latter would kill the *A. tumefaciens* cells. *Rhodotorula* colonies that grew after 2 days would be restreaked on YPD plates containing nourseothricin to isolate individual clones. These individual clones would also be grown in the presence of 5-FOA to confirm the loss of URA3 in the yeast genome; PCR amplification of the URA3 locus would be used to confirm the insertion of the resistance cassette and loss of URA3.

A person skilled in the art would then screen several of the *Rhodotorula* isolates, deleted for URA3, to analyze production of biosurfactant compounds produced by the KO strains as compared to the wild-type strain. This analysis would be performed by liquid chromatography-mass spectrometry as described in the section "High Resolution Liquid Chromatography-Electrospray Ionization-Mass Spectrometry (LC-ESI-MS)". This analysis would confirm that biosurfactant production is not altered by the URA3 deletion, and that CRISPR manipulations of the genome could then proceed as to produce Surfactant I in FIG. 25.

In order to generate a Rhodotorula strain that produces Surfactant I, as opposed to the complex acetylation series that is produced in nature, the sugar acetyltransferase(s) would need to be deleted from the *Rhodotorula* genome. A person skilled in the art would use a *Rhodotorula* strain, with a mutated or deleted URA3 gene, and a yeast expression CRISPR plasmid encoding the relevant guide RNA and CRISPR-associated endonuclease (Cas protein).

In an exemplary embodiment, the CRISPR plasmid pCRCT could be employed to make the CRISPR deletion in the *Rhodotorula* genome similar to what has been described by Kong et al. 2018. [38] This plasmid encodes iCas9, tracrRNA, and crRNAs as described by Bao et al. in ACS Synth Biol. 2014. [39] and is known as the Homology-Integrated CRISPR-Cas (HI-CRISPR) System. Briefly, the 20-nt guide RNA sequences together with NGG PAM sequence would be identified on both strands of the MD1149 sugar acetyltransferase genes BMF94_2857 BMF94_0387. CRISPR plasmids targeting each of the two genes would be generated using the pCRCT CRISPR plasmid. Plasmid would be transformed into *Rhodotorula* MD1149 (ura3−) using the previously described *Agrobacterium tumefaciens* method, or electroporating *Rhodotorula* competent cells as described by Kong et al. 2018. [38] Positive recombinant isolates would be confirmed by PCR for loss of the sugar acetyltransferase gene(s). Loss of these genes would result in a dramatic shift in the biosurfactant profile produced by this *Rhodotorula* strain (biosurfactant compounds would no longer be acetylated). This shift in biosurfactant composition would easily be detected by LC-MS analyses by someone skilled in the art. As the mannitol 3-hydroxy C18 base compound is the primary compound produced by Rhodotorula MD1149 (Surfactant I), this Rhodotorula strain would become the production strain for industrial scale-up of the non-acetylated tunable biosurfactant compound Surfactant I illustrated in FIG. 25. This base compound could then be systematically modified to change it's aHLB as previously described.

Example 22. Method to Engineer a Cell to Knock Out Fragments of an Enzyme Involved in the Biosynthesis of an Amphiphilic Heteroatom Containing Hydrocarbon A MFE-2 coding fragment of about 1000 bp and about 1000 bp upstream and downstream of the MFE-2 gene can be amplified with primers. The amplified fragment can then be cloned into a vector such as pGEM®-T vector systems. The created vector is then digested with restriction enzymes which can cut the coding sequence of MFE-2, thus deleting the MFE-2 sequence.

An exemplary procedure to perform the knock out in *Rhodotula* strains is the procedure to inactivate a gene coding for acetyltransferase using a CRISPR system of Example 21 as will be understood by a skilled person, wherein the MFE-2 homolog in the Rhodotorula genome is BMF94_0710. The protein sequence is below:

(SEQ ID NO: 5)
MTSTLRYDDQVVVVTGAGGGLGRAYSLFYASRGAHVVVNDLSRENADRVV

AEINKDKGAEAIANYDSATEGAKLVQQALDKWGRVDVLINNAGILRDKSF

KSMTDNEWDLVQQVHVKGAYSCTKAVWPVMRKQKYGRIVNTASAAGIYGN

FGQANYSAAKMGLIGFAKTLAREGAKYGIIANAIAPVAASQMTETIMPPE

MLANLSPERIVALVALLTHPSTKASGQVFEAGAGWYGQLRWERTKGHVFK

TDSSFTPAAVRQQWTKINDYTDADHPAAITETDYLGFLEKAKSMPENEQG

QDTRFDGRTVLITGAGAGLGRAYALVFARHGANVVVNDMNADNARNVVEE

IQKAGGKATAVVASTLEGDKLVKAALDAYGALHTIICNAGILRDKSFAPM

TEQEWDAVYDTHLKGTYAVCKAAWPVFQKQRYGRIVTTSSAVGVHGNFGQ

SNYSTAKSAIIGLTRTLAIEGKKYGILANVLVPNAGTAMTATVWPEEYVK

AFSPDYVAPVVGYLGSEACETTMGLYEVSAGWCASIRWQRTYGYAFPVNK

DVQPEDLASKWDIVTRFDDKATYPNSTAESLEAIVSNFANEGQDDSTDYT

DPEDSDLVAKAKKEAQASGEYEYTERDVALYNIGVGATEKDLDLIFEQDE

HFQALPLFGVIPQFPVSSGLPLDWLPNFSPMMLLHGEQYLKLHAPIPTSG

KLVTEAKLAEVLDKGKAAAVTAVTVTKDASNGQVICENHSTTFIRGSGGF

GGRKTGKDRGAATAVNKPPSRKPDAIVEEKTLPQQAAIYRLSGDLNPLHV

DPNFAKVGGFDQPILHGLCSFGISGKHIFRKFGPYSDIKVRFAGVLFPGE

TLVTEMWKEGDKVIFVTKCKERGTVVLSSAAATLAQ

In summary, biodegradable surfactants, and related compositions, methods and systems are described herein. In particular, biodegradable surfactants are described, in which an amphiphilic heteroatom containing hydrocarbon optionally comprising at least one counterion (Z), and related compositions, methods and systems. A biodegradable surfactant described herein has an aHLB value in accordance with equation (1): aHLB=$20*G_h/(G_h-G_t)$ (1) wherein $G_h$ is the Group Number of a hydrophilic head portion of the biodegradable surfactant optionally comprising the at least one counterion (Z), and $G_t$ is the Group Number of a hydrophobic tail portion of the biodegradable surfactant. A biodegradable surfactant in the sense of the disclosure can be tuned to a set hydrophilic-lipophilic balance (aHLB) by selectively modifying at least one tuning moiety of the biodegradable surfactants to provide tuned biodegradable surfactants having an increase or decrease in their adjusted or tuned hydrophilic-lipophilic balance (aHLB).

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional tunable surfactants, and related compositions, methods and systems, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file IL-13125-PCT-Sequence-Listing_ST25 filed concurrently herewith is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Lyman, M., et al., *Rhodotorula taiwanensis MD1149 produces hypoacetylated PEFA compounds with increased surface activity compared to Rhodotorula babjevae MD1169*. PLoS ONE (13) 1: e0190373. https://doi.org/10.1371/journal.pone.0190373, 2018: p. 1-17.
2. Satpute, S. K., et al., *Methods for investigating biosurfactants and bioemulsifiers: a review*. Crit Rev Biotechnol, 2010. 30(2): p. 127-44.
3. Uzoigwe, C., et al., *Bioemulsifiers are not biosurfactants and require different screening approaches*. Front Microbiol, 2015. 6: p. 245.
4. Davies, J., *A quantitative kinetic theory of emulsion type, I. Physical chemistry of the emulsifying agent*. Proc. 2nd Intern. Congr. Surface Activity, Butterworths Scientific Publication, London, 1957: p. 426-438.
5. Guo, X., Z. Rong, and X. Ying, *Calculation of hydrophile-lipophile balance for polyethoxylated surfactants by group contribution method*. Journal of Colloid and Interface Science, 2006. 298(1): p. 441-450.
6. Pasquali, R. C., M. P. Taurozzi, and C. Bregni, *Some considerations about the hydrophilic-lipophilic balance system*. International journal of pharmaceutics, 2008. 356 (1-2): p. 44-51.
7. Varvaresou, A. and K. Iakovou, *Biosurfactants in cosmetics and biopharmaceuticals*. Lett Appl Microbiol, 2015. 61(3): p. 214-23.

8. Kosaric, N. V.-S., F., *Biosurfactants: Production and Utilization—Processes, Technologies, and Economics.* 2015, Boca Raton, Fla.: Taylor & Francis Group.
9. Reis, R. S. P., G. J.; Pereira, A. G.; Freire, D. M. G., *Biosurfactants: Production and Applications*, in *Biodegradation—Life of Science*, R. C. a. F. Rosenkranz, Editor. 2013, InTech.
10. Galdieri, L., et al., *Protein acetylation and acetyl coenzyme a metabolism in budding yeast.* Eukaryot Cell, 2014. 13(12): p. 1472-83.
11. Kurdistani, S. K. and M. Grunstein, *Histone acetylation and deacetylation in yeast.* Nat Rev Mol Cell Biol, 2003. 4(4): p. 276-84.
12. Saerens, K. M., L. Saey, and W. Soetaert, *One-step production of unacetylated sophorolipids by an acetyltransferase negative Candida bombicola.* Biotechnol Bioeng, 2011. 108(12): p. 2923-31.
13. Zhang, S., et al., *Engineering Rhodosporidium toruloides for increased lipid production.* Biotechnology and bioengineering, 2016. 113(5): p. 1056-1066.
14. Zhang, S., et al., *Metabolic engineering of the oleaginous yeast Rhodosporidium toruloides IFO0880 for lipid overproduction during high-density fermentation.* Applied Microbiology and Biotechnology, 2016. 100(21): p. 9393-9405.
15. Van Bogaert, I. N., et al., *Knocking out the MFE-2 gene of Candida bombicola leads to improved medium-chain sophorolipid production.* FEMS yeast research, 2009. 9(4): p. 610-617.
16. Bandaranayake, A. D. and S. C. Almo, *Recent advances in mammalian protein production.* FEBS letters, 2014. 588(2): p. 253-260.
17. Chang, L., et al., *Separation of four flavonol glycosides from Solanum rostratum Dunal using aqueous two-phase flotation followed by preparative high-performance liquid chromatography.* Journal of separation science, 2017. 40(3): p. 804-812.
18. Ibrahim, N. M. and B. B. Wheals, *Determination of alkylphenol ethoxylate non-ionic surfactants in trade effluents by sublation and high-performance liquid chromatography.* Analyst, 1996. 121(2): p. 239-242.
19. Bi, P.-y., H.-r. Dong, and J. Dong, *The recent progress of solvent sublation.* Journal of Chromatography A, 2010. 1217(16): p. 2716-2725.
20. Scarlett, M., et al., *Determination of dissolved nonylphenol ethoxylate surfactants in waste waters by gas stripping and isocratic high performance liquid chromatography.* Water Research, 1994. 28(10): p. 2109-2116.
21. Show, P. L., et al., *Recovery of lipase derived from Burkholderia cenocepacia ST8 using sustainable aqueous two-phase flotation composed of recycling hydrophilic organic solvent and inorganic salt.* Separation and Purification Technology, 2013. 110: p. 112-118.
22. Show, P. L., et al., *Direct recovery of lipase derived from Burkholderia cepacia in recycling aqueous two-phase flotation.* Separation and purification technology, 2011. 80(3): p. 577-584.
23. Wilhelmy, L., Ueber die Abhängigkeit der Capillaritäts-Constanten des Alkohols von Substanz und Gestalt des benetzten festen Körpers [*On the dependence of capillarity constants of alcohols from the substance and shape of the wetted solid bodies*]. Ann. Phys., 1863. 195: p. 177-217.
24. Santander, J., et al., *Mechanisms of intrinsic resistance to antimicrobial peptides of Edwardsiella ictaluri and its influence on fish gut inflammation and virulence.* Microbiology, 2013. 159(Pt 7): p. 1471-86.
25. Tulloch, A. and J. Spencer, *A new hydroxy fatty acid sophoroside from Candida bogoriensis.* Can. J. Chem, 1968. 46(3): p. 345-348.
26. Nunez, A., et al., *LC/MS analysis and lipase modification of the sophorolipids produced by Rhodotorula bogoriensis.* Biotechnol Lett, 2004. 26(13): p. 1087-93.
27. Ribeiro, I. A., et al., *Design of selective production of sophorolipids by Rhodotorula bogoriensis through nutritional requirements.* J Mol Recognit, 2012. 25(11): p. 630-40.
28. Brenton, A. G. and A. R. Godfrey, *Accurate mass measurement: terminology and treatment of data.* J Am Soc Mass Spectrom, 2010. 21(11): p. 1821-35.
29. Kulakovskaya, E. K., T, *Extracellular Glycolipids of Yeasts.* 2014, Waltham, Mass.: Academic Press (Elsevier).
30. Bentley, R., et al., *Gas chromatography of sugars and other polyhydroxy compounds.* Biochem Biophys Res Commun, 1963. 11: p. 14-8.
31. Tulloch, A. and J. Spencer, *Extracellular Glycolipids of Rhodotorula Species.* Canadian Journal of Chemistry, 1964. 42: p. 830-835.
32. Fossati, E., et al., *Synthesis of morphinan alkaloids in Saccharomyces cerevisiae.* PLoS One, 2015. 10(4): p. e0124459.
33. Rosano, G. L. and E. A. Ceccarelli, *Recombinant protein expression in Escherichia coli: advances and challenges.* Frontiers in microbiology, 2014. 5: p. 172.
34. Jarvis, D. L., *Developing baculovirus-insect cell expression systems for humanized recombinant glycoprotein production.* Virology, 2003. 310(1): p. 1-7.
35. Garay, L. A., et al., *Discovery of synthesis and secretion of polyol esters of fatty acids by four basidiomycetous yeast species in the order Sporidiobolales.* Journal of industrial microbiology & biotechnology, 2017. 44(6): p. 923-936.
36. Abbott, E. P., et al., *Overcoming recalcitrant transformation and gene manipulation in Pucciniomycotina yeasts.* Applied microbiology and biotechnology, 2013. 97(1): p. 283-295.
37. Liu, Y., et al., *Characterization of glyceraldehyde-3-phosphate dehydrogenase gene RtGPD1 and development of genetic transformation method by dominant selection in oleaginous yeast Rhodosporidium toruloides.* Applied microbiology and biotechnology, 2013. 97(2): p. 719-729.
38. Kong, M., et al., *Functional identification of glutamate cysteine ligase and glutathione synthetase in the marine yeast Rhodosporidium diobovatum.* The Science of Nature, 2018. 105(4): p. 1-9.
39. Bao, Z., et al., *Homology-integrated CRISPR-Cas (HI-CRISPR) system for one-step multigene disruption in Saccharomyces cerevisiae.* ACS synthetic biology, 2014. 4(5): p. 585-594.

The invention claimed is:

1. A method of modifying a tunable biodegradable surfactant having a first aHLB value to obtain a tuned biodegradable surfactant having a second aHLB value, the method comprising:

providing the tunable biodegradable surfactant having the first aHLB value, the tunable biodegradable surfactant comprising an amphiphilic heteroatom containing hydrocarbon and optionally at least one counterion (Z), the amphiphilic heteroatom containing hydrocarbon comprising a hydrophilic head portion of containing a maximum number of a hydrophilic functional group with a positive Group Number on the hydrocarbon the hydrophilic function group comprising at least one tunable moiety, and a hydrophobic tail portion containing the maximum number of a hydrophobic group of atoms with a negative Group Number on the hydrocarbon and forming a contiguous terminal section of the biodegradable surfactant; and modifying the at least one tunable moiety of the tunable biodegradable surfactant to obtain the tuned biodegradable surfactant comprising at least one tuned moiety and having the second aHLB value and optionally the at least one counterion (Z), wherein the amphiphilic heteroatom containing hydrocarbon has Formula (X):

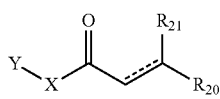

Formula (X)

in which
 ----- represents a single or double bond when R21 is H, and a single bond when R21 is other than H;
X is selected from one of O, NH, or NCH3;

Y is selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl groups, optionally substituted with 1-6 tuning moieties independently selected from sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy;

R20 is a C11-C21 linear or branched alkyl, alkenyl, or alkynyl group; and

R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and the at least one counterion (Z) is selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluorborate, hexafluorophospate, p-toluenesulfonate, benzenesulfonate, nitrate, trifluoroacetate, fluoride, chloride, bromide, and iodide or any combinations thereof;

wherein the at least one counterion (Z) is selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluorborate, hexafluorophospate, p-toluenesulfonate, benzenesulfonate, nitrate, trifluoroacetate, fluoride, chloride, bromide, and iodide or any combinations thereof;

and wherein $$aHLB = 20 * G_h/(G_h - G_t) \quad (1)$$

in which
$G_h$ is the Group Number of the head portion of the amphiphilic heteroatom containing hydrocarbon, $G_t$ is the Group Number of the tail portion of amphiphilic heteroatom containing hydrocarbon.

2. The method of claim 1, further comprising:
providing a look-up table containing a list of Group Numbers each corresponding to a reference moiety,
calculating a head-portion Group Number of the at least one tuned moiety,
identifying the at least one tuned moiety having the head-portion Group Number from the look-up table, and
converting the at least one tunable moiety of the tunable biodegradable surfactant into the at least one tuned moiety.

3. The method of claim 1, wherein the first aHLB value is in a range of 5-10 and the second aHLB value is in a range of 15-20.

4. The method of claim 1, wherein when the first aHLB is in the range of 5-10, the at least one tuned moiety is independently selected from acetyloxy, or C1-C2 alkoxy.

5. The method of claim 1, wherein when the first aHLB value is in the range of 15-20, the at least one tuned moiety is independently selected from sulfate, sulfonate, phosphate, phosphonate having at least one counter ion selected from the group consisting of proton, ammonium, C-C4 tetraalkyl ammonium, sodium (I), potassium (I), cesium (I), magnesium (II), calcium (II), zinc (II) or any combinations thereof.

6. The method of claim 1, wherein the tunable biodegradable surfactant has Formula (XX):

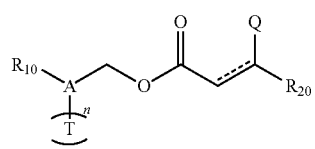

Formula (XX)

in which
- - - - - : represents a single or double bond when Q is H, and a single bond when Q is other than H;
n is 1-6;
A is a node moiety selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl group,
T each is a tuning moiety each independently selected from OH, or $NH_2$;
Q is selected from H, OH, or $NH_2$;
R10 is H, or C1-C2 alkyl group;
R20 is a C11-C21 linear or branched alkyl, alkenyl, or alkynyl group;
the R22 and each of R12 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy; and
and the tuned biodegradable surfactant has Formula (XXII),

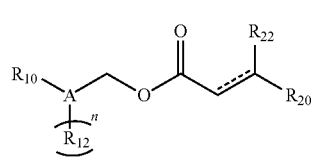

Formula (XXII)

in which
- - - - - : represents a single or double bond when R22 is H, and a single bond when R22 is other than H;
n is 1-6;
A is a node moiety selected from C2-C8 linear or branched alkyl, C4-C8 cycloalkyl, C2-C8 linear or branched heteroalkyl, C4-C8 heterocycloalkyl, C4-C8 heteroalkyl heterocycloalkyl, C4-C8 aryl alkyl, C4-C8 alkyl aryl, C4-C8 heteroaryl alkyl, and C4-C8 alkyl heteroaryl group,
each is a tuning moiety each independently selected from OH, or $NH_2$;
Q is selected from H, OH, or $NH_2$;
R10 is H, or C1-C2 alkyl warn;
R20 is a C11-C21 linear or branched alkyl, alkenyl, or alkynyl group;
the R22 and each of R12 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy;
and wherein the at least one counterion (Z) is selected from the group selected from the group consisting of proton, ammonium, C-C4 tetraalkyl ammonium, sodium (I), potassium (I), cesium (I), magnesium (II), calcium (II), zinc (II), inorganic sulfate ($SO_4^{2-}$), inorganic phosphate ($PO_4^{3-}$), tetrafluorborate, hexafluorophospate, p-toluenesulfonate, benzenesulfonate, nitrate, trifluoroacetate, fluoride, chloride, bromide, and iodide or any combinations thereof.

7. The method of claim 1, wherein the tunable biodegradable surfactant has Formula (XXI),

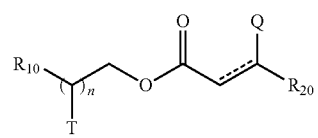

Formula (XXI)

In which
- - - - - : represents a single or double bond when Q is H, and a single bond when Q is other than H;
n is 1-6,
T each is a tuning moiety each independently selected from OH, or $NH_2$;
Q is a selected from H, OH, or $NH_2$;
R10 is H, or C1-C2 alkyl group; and
R20 is a C11-C21 linear or branched alkyl, alkenyl, or alkynyl group and the R21 and each of R11 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy,
and the tuned biodegradable surfactant has Formula (XXIII),

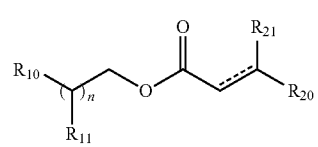

Formula (XXIII)

in which
- - - - - represents a single or double bond when R21 is H, and a single bond when R21 is other than H;
n is 1-6,
each is a tuning moiety each independently selected from OH, or NH$_2$;
Q is a selected from H, OH, or NH$_2$;
R10 is H, or C1-C2 alkyl group; and R20 is a C11-C21 linear or branched alkyl, alkenyl, or alkynyl group and the R21 and each of R11 groups are independently selected from H, sulfate, sulfonate, phosphate, phosphonate, carboxylate, C1-C2 alkyl amine, C1-C2 dialkyl amine, C1-C2 trialkyl ammonium, pyridinium, acetyloxy, C1-C2 alkoxy.

8. The method of claim 1, wherein the tuned biodegradable surfactant is selected from the group consisting of

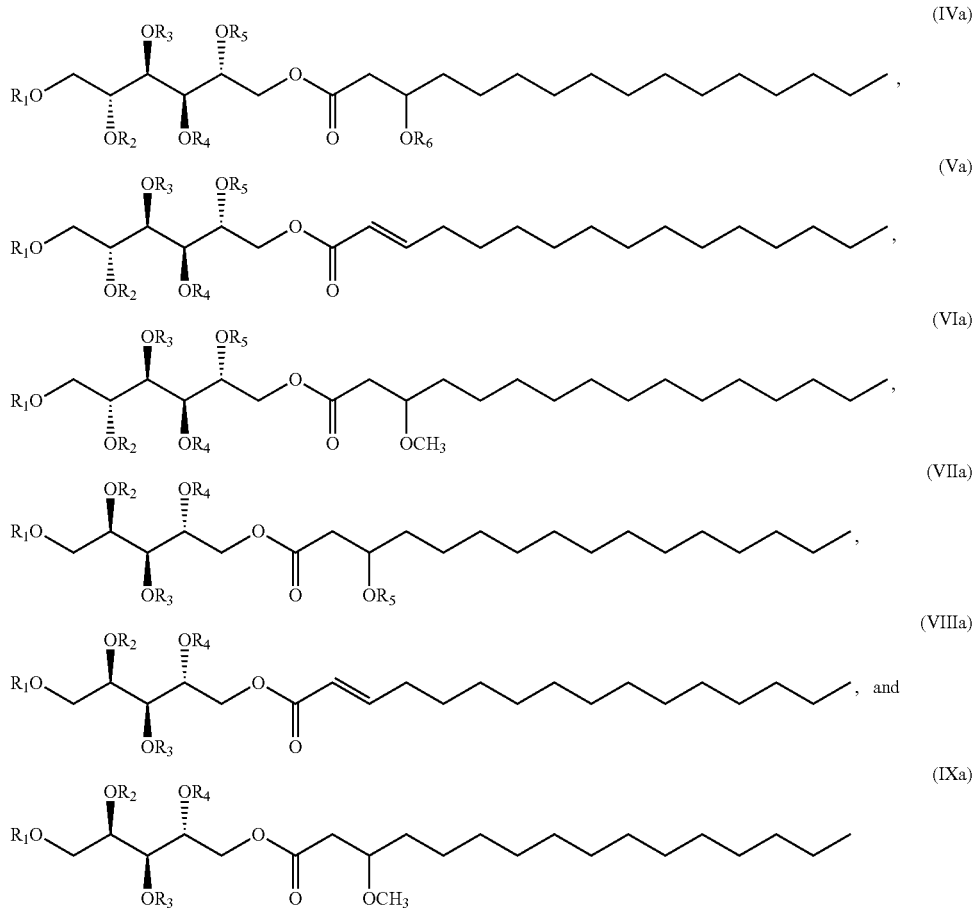

wherein OR1 to OR6 are independently selected from sulfate, phosphate, hydroxyl, acetyloxy, or C1-C2 alkoxy.

9. The method of claim 1, wherein the tuned biodegradable surfactant is selected from the group consisting of

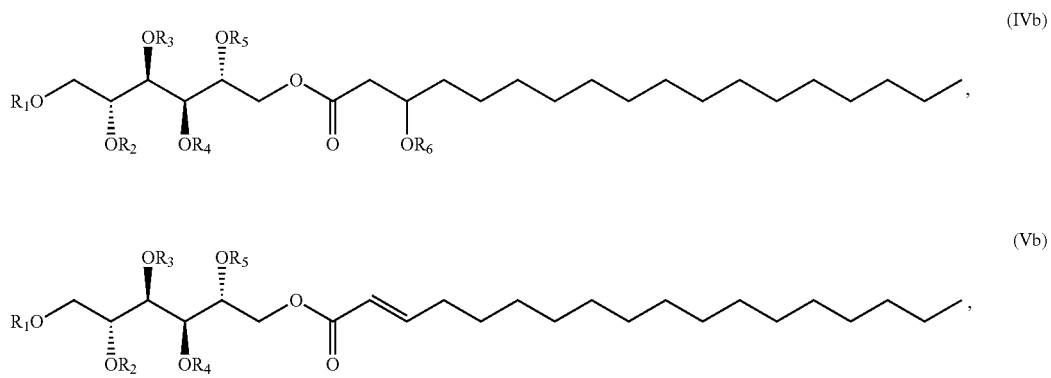

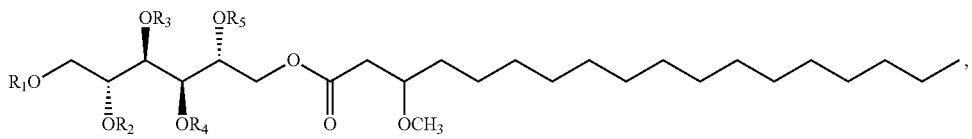
(VIb)

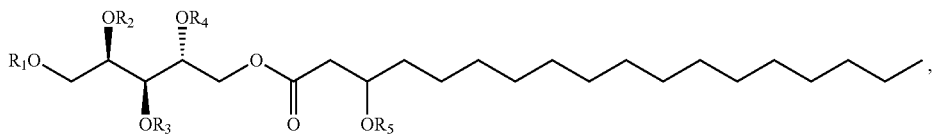
(VIIb)

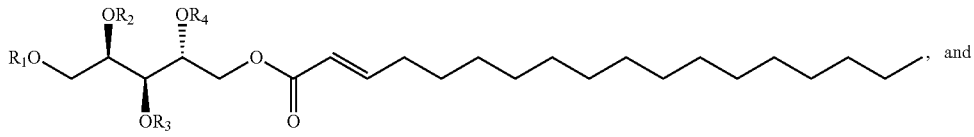
(VIIIb), and

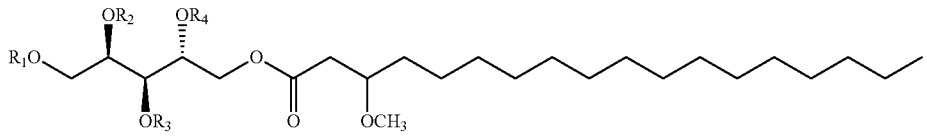
(IXb)

wherein OR1 to OR6 are independently selected from sulfate, phosphate, hydroxyl, acetyloxy, or C1-C2 alkoxy.

10. The method of claim 1, wherein the tuned biodegradable surfant is represented by Formula (XI)

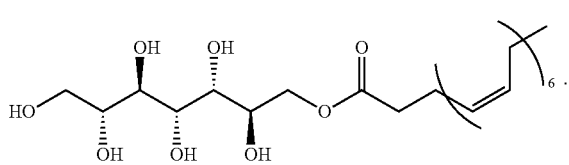
Formula (XI)

11. The method of claim 1, wherein the tuned biodegradable surfant is represented by Formula (XII)

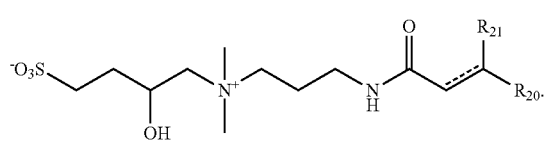
Formula (XII)

wherein
----- represents a single or double bond when R21 is H, and a single bond when R21 is other than H;
R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and
R20 is a C11-C21 linear or branched alkyl, alkenyl, or alkynyl groups.

12. The method of claim 1, wherein the tuned biodegradable surfant is represented by Formula (XIII)

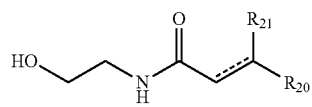
Formula (XIII)

wherein
----- represents a single or double bond when R21 is H, and a single bond when R21 is other than H;
R21 is selected from sulfate, sulfonate, phosphate, phosphonate, carboxylate, amine, C1-C2 alkyl amine, C1-C2 dialkyl amine, C1-C2 trialkylammonium, pyridinium, hydroxyl, acetyloxy, C1-C2 alkoxy; and
R20 is a C11-C21 linear or branched alkyl, alkenyl, or alkynyl group.

13. The method of claim 1, wherein the tuned biodegradable surfant is represented by Formula (XIV)

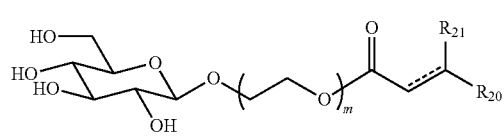
Formula (XIV)

wherein
m=1-6;
----- represents a single or double bond when R21 is H, and a single bond when R21 is other than H;
R21 is selected from sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and
R20 is a C11-C21 linear or branched alkyl, alkenyl, or alkynyl group.

14. The method of claim 1, wherein the tuned biodegradable surfant is represented by Formula (XV)

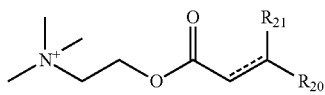

Formula (XV)

wherein

----- : represents a single or double bond when R21 is H, and a single bond when R21 is other than H;

R21 is selected from H, sulfate, sulfonate, phosphate, phosphonate, carboxylate, amine, C1-C2 alkyl amine, C1-C2 dialkyl amine, C1-C2 trialkyl ammonium, pyridinium, hydroxyl, acetyloxy, C1-C2 alkoxy; and R20 is a C11-C21 linear or branched alkyl, alkenyl, or alkynyl group.

15. The method of claim 1, wherein the tuned biodegradable surfant is represented by Formula (III-1S)

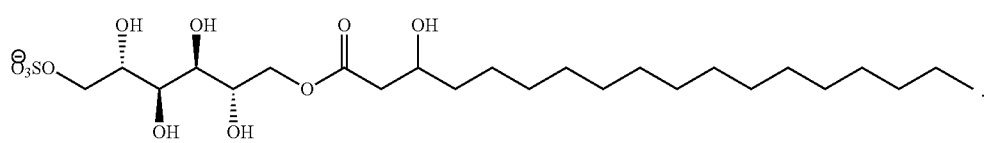

Formula (III-1S)

16. The method of claim 1, wherein the tuned biodegradable surfant is represented by Formula (III-6S)

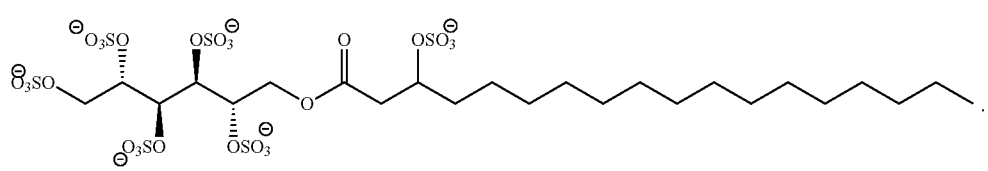

Formula (III-6S)

* * * * *

SEQUENCE LISTING

<160> NUMBER OF SEQ ID NOS: 5

<210> SEQ ID NO 1
<211> LENGTH: 259
<212> TYPE: PRT
<213> ORGANISM: Candida bombicola

```
<220> FEATURE:
<221> NAME/KEY: MISC_FEATURE
<222> LOCATION: (1)..(259)
<223> OTHER INFORMATION: Acetyltransferase

<400> SEQUENCE: 1

Met Val Val Asn Ser Ser Lys Asp Pro Gln Asn Lys Gly Met Thr Pro
1               5                   10                  15

Arg Lys Glu Ile Asp Gln Glu Met Val Ser Trp Ala Lys Lys Asn Leu
            20                  25                  30

Lys Asn Thr Pro Gly Asn Glu Asn Tyr Glu Lys Met Val Ser Gly Val
        35                  40                  45

Pro Tyr Asn Pro Tyr Asp Pro Asp Leu Met Phe Arg Ala Leu Ala Thr
50                  55                  60

Ser Glu Lys Val Arg Glu Phe Asn Thr Ile Ala Ser Glu Ser Arg Thr
65                  70                  75                  80

Phe Glu Ser Asn His Ala Ala Tyr Ile Lys Lys Val Glu Ile Leu Lys
                85                  90                  95

Asp Thr Phe Gly Gln Thr Lys Asp Ile Val Trp Leu Thr Ala Pro Phe
            100                 105                 110

Ser Val Asp Phe Gly Phe Asn Ile Ser Val Gly Glu His Phe Tyr Ala
        115                 120                 125

Asn Phe Asn Val Cys Phe Leu Asp Ser Ala Pro Ile Ile Phe Gly Asp
130                 135                 140

Glu Val Ile Val Gly Pro Asn Thr Thr Phe Val Thr Ala Thr His Pro
145                 150                 155                 160

Ile Ser Pro Glu Lys Arg Ala Arg Arg Ile Val Tyr Ala Leu Pro Ile
                165                 170                 175

Lys Val Gly Asn Asn Val Trp Ile Gly Ala Asn Val Thr Val Leu Pro
            180                 185                 190

Gly Val Thr Ile Gly Asp Gly Ser Thr Ile Ala Ala Gly Ala Val Val
        195                 200                 205

Arg Glu Asp Val Pro Pro Arg Thr Val Val Gly Val Pro Ala Arg
210                 215                 220

Ile Leu Lys His Ile Pro Glu Glu Asp Pro Glu Ala Glu Gly Glu
225                 230                 235                 240

Glu Leu Glu Phe Leu Leu Pro Val Glu Met Asn Val Asn Thr Ala Asn
                245                 250                 255

Gln Lys Val

<210> SEQ ID NO 2
<211> LENGTH: 244
<212> TYPE: PRT
<213> ORGANISM: Rhodotorula taiwanensis
<220> FEATURE:
<221> NAME/KEY: MISC_FEATURE
<222> LOCATION: (1)..(244)
<223> OTHER INFORMATION: BMF94_2857 hypothetical protein

<400> SEQUENCE: 2

Met Pro Glu Phe Val Arg Ala Ser Ala Asp Glu Leu Glu Ala Phe Lys
1               5                   10                  15

Ala Leu Ser Glu Arg Glu Lys Met Val Lys Gly Leu Ala Tyr Leu Ala
            20                  25                  30

Met Asp Asp Gln Glu Leu Ala Arg Asp Arg Leu Lys Ala Arg Thr Leu
        35                  40                  45

Cys Gln His His Pro Phe Ile Glu Trp Arg Asp Asp Leu Pro Ile Ser
```

```
            50                  55                  60
Glu Phe Tyr Gly Pro Asp Ser Arg Leu Gln Asn Leu Ala Glu Leu Phe
 65                  70                  75                  80

Gln Val Ser Leu Glu Arg Val Arg Ser Ile Gly Ile Glu Pro Pro Leu
                 85                  90                  95

Tyr Val Asp Tyr Gly Tyr Asn Ile Glu Phe Arg Gly Asp Phe Tyr Ala
                100                 105                 110

Asn Phe Gly Ala Val Phe Leu Asp Cys Ala Lys Ile Ser Phe Gly Ala
                115                 120                 125

Arg Thr Leu Leu Gly Pro Gly Val His Val Tyr Cys Ala Thr His Ala
            130                 135                 140

Val Glu Val Asp Glu Arg Val Ala Gly Tyr Glu Arg Ala Tyr Pro Val
145                 150                 155                 160

Glu Leu Gly Asp Asp Leu Trp Val Gly Gly Ala Lys Ile Ile Gly
                165                 170                 175

Pro Cys Lys Ile Gly Asn Asn Cys Thr Ile Ala Ala Asn Ala Val Val
                180                 185                 190

Lys Gly Asp Phe Pro Asp Asn Val Val Ile Gly Gly Ile Pro Ala Arg
            195                 200                 205

Ile Leu Lys His Leu Asp Pro Pro Gln Gly Pro Ile Asp Pro Glu Asp
        210                 215                 220

Arg Arg Leu Val Val Pro Leu Pro Ser Ala Lys Ser Ala Ala Lys Asn
225                 230                 235                 240

Asp Ile Thr Met

<210> SEQ ID NO 3
<211> LENGTH: 242
<212> TYPE: PRT
<213> ORGANISM: Rhodotorula taiwanensis
<220> FEATURE:
<221> NAME/KEY: MISC_FEATURE
<222> LOCATION: (1)..(242)
<223> OTHER INFORMATION: BMF94_0387 hypothetical protein

<400> SEQUENCE: 3

Met Ala Glu Gln Thr Glu Thr Pro Thr Trp Asn Gly Ile Asp Leu Val
 1               5                  10                  15

Glu Asn Arg Arg Arg Met Glu Arg Gly Glu Leu Tyr Thr Ala Phe Val
                 20                  25                  30

Pro Glu Leu Thr Lys Glu Arg Arg Val Ala Ser Gln Ala Cys Ala Lys
             35                  40                  45

Tyr Asn Arg Val Ala Thr Glu Val Thr Arg Arg Glu Gln Val Glu Leu
 50                  55                  60

Phe Lys Lys Ile Val Thr Thr Leu Pro Asp Leu Pro Pro Ala Lys Glu
 65                  70                  75                  80

Asp Pro Asp Glu Asp Glu Ala Gln Leu Thr Ala Phe Pro Trp Ala Glu
                 85                  90                  95

Pro Pro Phe Lys Val Asp Tyr Cys Gly Arg Ile Phe Ile Gly Glu Asn
                100                 105                 110

Ser Phe Met Asn Phe Asn Phe Ile Val Leu Asn Thr Cys Glu Val Arg
            115                 120                 125

Ile Gly Ser Arg Cys Leu Phe Gly Pro Asn Val Ser Leu Phe Ala Gly
        130                 135                 140

Thr His His Pro Leu Asp Pro Ala Ile Arg Asn Gly Thr Ala Gly Pro Glu
145                 150                 155                 160
```

```
Asn Gly Gly Pro Ile Thr Ile Gly Asp Asp Cys Trp Phe Gly Gly Asn
                165                 170                 175

Val Thr Val Leu Pro His Val Thr Ile Gly Arg Gly Val Thr Val Gly
            180                 185                 190

Ala Gly Ser Val Val Thr Lys Ser Val Pro Ala Phe Ala Val Val Val
        195                 200                 205

Gly Asn Pro Ala Arg Ile Val Arg Lys Ile Glu Ser Glu Trp Ala Asn
    210                 215                 220

Glu His Phe Ala Ala His Pro Glu Glu Gln Trp Glu Val Pro Thr Thr
225                 230                 235                 240

Lys Thr

<210> SEQ ID NO 4
<211> LENGTH: 292
<212> TYPE: PRT
<213> ORGANISM: Rhodoturula taiwanensis
<220> FEATURE:
<221> NAME/KEY: MISC_FEATURE
<222> LOCATION: (1)..(292)
<223> OTHER INFORMATION: Orotidine-5'-phosphate decarboxylase (ODCase)

<400> SEQUENCE: 4

Met Pro Ser Val Thr Lys Arg Thr Tyr Ala Asp Arg Ala Ala Lys His
1               5                   10                  15

Pro Ile Pro Val Ala Gln Gln Leu Leu Ala Val Cys Asp Arg Lys Arg
            20                  25                  30

Thr Asn Leu Cys Val Ser Val Asp Val Thr Ser Lys Ala Ser Leu Leu
        35                  40                  45

Arg Ile Ala Asp Ala Ala Gly Pro Tyr Cys Cys Cys Ile Lys Thr His
    50                  55                  60

Ile Asp Ile Val Glu Asp Phe Asp Arg Asp Leu Val Glu Gln Leu Gln
65                  70                  75                  80

Ala Leu Ala Glu Lys His Asp Phe Leu Ile Trp Glu Asp Arg Lys Phe
                85                  90                  95

Ala Asp Ile Gly Thr Arg Glu Gly Asp Leu Met Thr Glu Glu Lys Phe
            100                 105                 110

Gly Leu Thr Arg Arg Leu Val Tyr Ser Ser Gly Ile Tyr Lys Ile Ala
        115                 120                 125

Ser Trp Ala His Ile Thr Asn Ala His Leu Val Pro Gly Glu Gly Ile
    130                 135                 140

Leu Thr Gly Leu Ala Ser Val Gly Glu Pro Leu Gly Arg Gly Leu Leu
145                 150                 155                 160

Leu Leu Ala Glu Met Ser Ala Lys Gly Asn Leu Ala Thr Gly Glu Tyr
                165                 170                 175

Thr Ala Lys Asn Val Glu Ala Ala Arg Arg Tyr Pro Asn Phe Val Met
            180                 185                 190

Gly Phe Val Ala Met Lys Arg Val Asp Glu Arg Glu Thr Ala Gly
        195                 200                 205

Gly Val Thr Ala Gly Glu Gly Pro Asp Phe Val Ile Met Thr Pro Gly
    210                 215                 220

Ile Gly Leu Asp Ser Lys Gly Asp Gly Met Gly Gln Gln Tyr Arg Thr
225                 230                 235                 240

Pro Asp Glu Val Ile Arg Glu Ser Gly Cys Asp Ile Ile Val Gly
                245                 250                 255

Arg Gly Ile Tyr Gly Gly Gly Asp Gly Asn Pro Ser Glu Glu Ile Val
            260                 265                 270
```

```
Lys Gln Cys Gln Arg Tyr Gln Ala Ala Gly Trp Glu Ser Tyr Glu Arg
            275                 280                 285

Arg Leu Lys Glu
    290

<210> SEQ ID NO 5
<211> LENGTH: 886
<212> TYPE: PRT
<213> ORGANISM: Rhodoturula taiwanensis
<220> FEATURE:
<221> NAME/KEY: MISC_FEATURE
<222> LOCATION: (1)..(886)
<223> OTHER INFORMATION: MFE-2 homolog BMF94_0710

<400> SEQUENCE: 5

Met Thr Ser Thr Leu Arg Tyr Asp Asp Gln Val Val Val Thr Gly
1               5                   10                  15

Ala Gly Gly Gly Leu Gly Arg Ala Tyr Ser Leu Phe Tyr Ala Ser Arg
            20                  25                  30

Gly Ala His Val Val Asn Asp Leu Ser Arg Glu Asn Ala Asp Arg
            35                  40                  45

Val Val Ala Glu Ile Asn Lys Asp Lys Gly Ala Glu Ala Ile Ala Asn
50                  55                  60

Tyr Asp Ser Ala Thr Glu Gly Ala Lys Leu Val Gln Gln Ala Leu Asp
65                  70                  75                  80

Lys Trp Gly Arg Val Asp Val Leu Ile Asn Asn Ala Gly Ile Leu Arg
                85                  90                  95

Asp Lys Ser Phe Lys Ser Met Thr Asp Asn Glu Trp Asp Leu Val Gln
            100                 105                 110

Gln Val His Val Lys Gly Ala Tyr Ser Cys Thr Lys Ala Val Trp Pro
        115                 120                 125

Val Met Arg Lys Gln Lys Tyr Gly Arg Ile Val Asn Thr Ala Ser Ala
    130                 135                 140

Ala Gly Ile Tyr Gly Asn Phe Gly Gln Ala Asn Tyr Ser Ala Ala Lys
145                 150                 155                 160

Met Gly Leu Ile Gly Phe Ala Lys Thr Leu Ala Arg Glu Gly Ala Lys
                165                 170                 175

Tyr Gly Ile Ile Ala Asn Ala Ile Ala Pro Val Ala Ala Ser Gln Met
            180                 185                 190

Thr Glu Thr Ile Met Pro Pro Glu Met Leu Ala Asn Leu Ser Pro Glu
        195                 200                 205

Arg Ile Val Ala Leu Val Ala Leu Leu Thr His Pro Ser Thr Lys Ala
    210                 215                 220

Ser Gly Gln Val Phe Glu Ala Gly Ala Gly Trp Tyr Gly Gln Leu Arg
225                 230                 235                 240

Trp Glu Arg Thr Lys Gly His Val Phe Lys Thr Asp Ser Ser Phe Thr
                245                 250                 255

Pro Ala Ala Val Arg Gln Gln Trp Thr Lys Ile Asn Asp Tyr Thr Asp
            260                 265                 270

Ala Asp His Pro Ala Ala Ile Thr Glu Thr Asp Tyr Leu Gly Phe Leu
        275                 280                 285

Glu Lys Ala Lys Ser Met Pro Glu Asn Glu Gln Gly Gln Asp Thr Arg
    290                 295                 300

Phe Asp Gly Arg Thr Val Leu Ile Thr Gly Ala Gly Ala Gly Leu Gly
305                 310                 315                 320
```

-continued

Arg Ala Tyr Ala Leu Val Phe Ala Arg His Gly Ala Asn Val Val Val
                325                 330                 335

Asn Asp Met Asn Ala Asp Asn Ala Arg Asn Val Val Glu Glu Ile Gln
            340                 345                 350

Lys Ala Gly Gly Lys Ala Thr Ala Val Val Ala Ser Thr Leu Glu Gly
        355                 360                 365

Asp Lys Leu Val Lys Ala Ala Leu Asp Ala Tyr Gly Ala Leu His Thr
    370                 375                 380

Ile Ile Cys Asn Ala Gly Ile Leu Arg Asp Lys Ser Phe Ala Pro Met
385                 390                 395                 400

Thr Glu Gln Glu Trp Asp Ala Val Tyr Asp Thr His Leu Lys Gly Thr
                405                 410                 415

Tyr Ala Val Cys Lys Ala Ala Trp Pro Val Phe Gln Lys Gln Arg Tyr
            420                 425                 430

Gly Arg Ile Val Thr Thr Ser Ser Ala Val Gly Val His Gly Asn Phe
        435                 440                 445

Gly Gln Ser Asn Tyr Ser Thr Ala Lys Ser Ala Ile Ile Gly Leu Thr
    450                 455                 460

Arg Thr Leu Ala Ile Glu Gly Lys Lys Tyr Gly Ile Leu Ala Asn Val
465                 470                 475                 480

Leu Val Pro Asn Ala Gly Thr Ala Met Thr Ala Thr Val Trp Pro Glu
                485                 490                 495

Glu Tyr Val Lys Ala Phe Ser Pro Asp Tyr Val Ala Pro Val Val Gly
            500                 505                 510

Tyr Leu Gly Ser Glu Ala Cys Glu Thr Thr Met Gly Leu Tyr Glu Val
        515                 520                 525

Ser Ala Gly Trp Cys Ala Ser Ile Arg Trp Gln Arg Thr Tyr Gly Tyr
    530                 535                 540

Ala Phe Pro Val Asn Lys Asp Val Gln Pro Glu Asp Leu Ala Ser Lys
545                 550                 555                 560

Trp Asp Ile Val Thr Arg Phe Asp Asp Lys Ala Thr Tyr Pro Asn Ser
                565                 570                 575

Thr Ala Glu Ser Leu Glu Ala Ile Val Ser Asn Phe Ala Asn Glu Gly
            580                 585                 590

Gln Asp Asp Ser Thr Asp Tyr Thr Asp Pro Glu Asp Ser Asp Leu Val
        595                 600                 605

Ala Lys Ala Lys Lys Glu Ala Gln Ala Ser Gly Glu Tyr Glu Tyr Thr
    610                 615                 620

Glu Arg Asp Val Ala Leu Tyr Asn Ile Gly Val Gly Ala Thr Glu Lys
625                 630                 635                 640

Asp Leu Asp Leu Ile Phe Glu Gln Asp Glu His Phe Gln Ala Leu Pro
                645                 650                 655

Leu Phe Gly Val Ile Pro Gln Phe Pro Val Ser Ser Gly Leu Pro Leu
            660                 665                 670

Asp Trp Leu Pro Asn Phe Ser Pro Met Met Leu Leu His Gly Glu Gln
        675                 680                 685

Tyr Leu Lys Leu His Ala Pro Ile Pro Thr Ser Gly Lys Leu Val Thr
    690                 695                 700

Glu Ala Lys Leu Ala Glu Val Leu Asp Lys Gly Lys Ala Ala Ala Val
705                 710                 715                 720

Thr Ala Val Thr Val Thr Lys Asp Ala Ser Asn Gly Gln Val Ile Cys
                725                 730                 735

Glu Asn His Ser Thr Thr Phe Ile Arg Gly Ser Gly Gly Phe Gly Gly

-continued

| | | 740 | | | | 745 | | | | 750 | | |
|---|---|---|---|---|---|---|---|---|---|---|---|---|
| Arg | Lys | Thr | Gly | Lys | Asp | Arg | Gly | Ala | Ala | Thr | Ala | Val | Asn | Lys | Pro |
| | | 755 | | | | 760 | | | | 765 | | |
| Pro | Ser | Arg | Lys | Pro | Asp | Ala | Ile | Val | Glu | Glu | Lys | Thr | Leu | Pro | Gln |
| | | 770 | | | | 775 | | | | 780 | | |
| Gln | Ala | Ala | Ile | Tyr | Arg | Leu | Ser | Gly | Asp | Leu | Asn | Pro | Leu | His | Val |
| 785 | | | | 790 | | | | 795 | | | | 800 |
| Asp | Pro | Asn | Phe | Ala | Lys | Val | Gly | Gly | Phe | Asp | Gln | Pro | Ile | Leu | His |
| | | | 805 | | | | 810 | | | | 815 |
| Gly | Leu | Cys | Ser | Phe | Gly | Ile | Ser | Gly | Lys | His | Ile | Phe | Arg | Lys | Phe |
| | | 820 | | | | 825 | | | | 830 | | |
| Gly | Pro | Tyr | Ser | Asp | Ile | Lys | Val | Arg | Phe | Ala | Gly | Val | Leu | Phe | Pro |
| | | 835 | | | | 840 | | | | 845 | | |
| Gly | Glu | Thr | Leu | Val | Thr | Glu | Met | Trp | Lys | Glu | Gly | Asp | Lys | Val | Ile |
| | 850 | | | | 855 | | | | 860 | | | |
| Phe | Val | Thr | Lys | Cys | Lys | Glu | Arg | Gly | Thr | Val | Val | Leu | Ser | Ser | Ala |
| 865 | | | | 870 | | | | 875 | | | | 880 |
| Ala | Ala | Thr | Leu | Ala | Gln | | | | | | | |
| | | | 885 | | | | | | | | | |